(12) United States Patent
Borovinskih et al.

(10) Patent No.: US 10,248,883 B2
(45) Date of Patent: Apr. 2, 2019

(54) PHOTOGRAPH-BASED ASSESSMENT OF DENTAL TREATMENTS AND PROCEDURES

(71) Applicant: Align Technology, Inc., San Jose, CA (US)

(72) Inventors: Artem Borovinskih, San Jose, CA (US); Mitra Derakhshan, Herndon, VA (US); Carina Koppers, Amsterdam (NL); Eric Meyer, Calabasas, CA (US); Ekaterina Tolstaya, Moscow (RU); Yury Brailov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 596 days.

(21) Appl. No.: 14/831,548

(22) Filed: Aug. 20, 2015

(65) Prior Publication Data

US 2017/0049311 A1    Feb. 23, 2017

(51) Int. Cl.
*G06K 9/62* (2006.01)
*H04N 7/18* (2006.01)
(Continued)

(52) U.S. Cl.
CPC ............ *G06K 9/6202* (2013.01); *A61C 7/002* (2013.01); *G06T 5/20* (2013.01); *G06T 7/0014* (2013.01);
(Continued)

(58) Field of Classification Search
CPC combination set(s) only.
See application file for complete search history.

(56) References Cited

U.S. PATENT DOCUMENTS 2,171,695 A    9/1939    Harper
2,467,432 A    4/1949    Kesling
(Continued)

FOREIGN PATENT DOCUMENTS

AU    517102 B    11/1977
AU    3031677 A    11/1977
(Continued)

OTHER PUBLICATIONS

US 8,553,966 B1, 10/2013, Alpern et al. (withdrawn)
(Continued)

*Primary Examiner* — Dave Czekaj
*Assistant Examiner* — Tyler W. Sullivan
(74) *Attorney, Agent, or Firm* — Shay Glenn LLP

(57) ABSTRACT

The current document is directed to methods and systems for monitoring a dental patient's progress during a course of treatment. A three-dimensional model of the expected positions of the patient's teeth can be projected, in time, from a three-dimensional model of the patient's teeth prepared prior to beginning the treatment. A digital camera is used to take one or more two-dimensional photographs of the patient's teeth, which are input to a monitoring system. The monitoring system determines virtual-camera parameters for each two-dimensional input image with respect to the time-projected three-dimensional model, uses the determined virtual-camera parameters to generate two-dimensional images from the three-dimensional model, and then compares each input photograph to the corresponding generated two-dimensional image in order to determine how closely the three-dimensional arrangement of the patient's teeth corresponds to the time-projected three-dimensional arrangement.

19 Claims, 36 Drawing Sheets

(51) Int. Cl.
  *G06T 5/20* (2006.01)
  *A61C 7/00* (2006.01)
  *G06T 7/00* (2017.01)
  *G06T 7/32* (2017.01)
  *G06T 7/136* (2017.01)

(52) U.S. Cl.
  CPC .............. *G06T 7/136* (2017.01); *G06T 7/32* (2017.01); *H04N 7/183* (2013.01); *A61C 2007/004* (2013.01); *G06T 2207/30036* (2013.01)

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,255,138 A | 3/1981 | Frohn |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,629,424 A | 12/1986 | Lauks et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,204,670 A | 4/1993 | Stinton |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,499,633 A | 3/1996 | Fenton |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,725,376 A | 3/1998 | Poirier |
| 5,725,378 A | 3/1998 | Wang |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |

(56) References Cited

U.S. PATENT DOCUMENTS

| | | |
|---|---|---|
| 5,774,425 A | 6/1998 | Ivanov et al. |
| 5,790,242 A | 8/1998 | Stern et al. |
| 5,799,100 A | 8/1998 | Clarke et al. |
| 5,800,174 A | 9/1998 | Andersson |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,980,246 A | 11/1999 | Ramsay et al. |
| 5,989,023 A | 11/1999 | Summer et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,099,303 A | 8/2000 | Gibbs et al. |
| 6,099,314 A | 8/2000 | Kopelman et al. |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,212,435 B1 | 4/2001 | Lattner et al. |
| 6,217,334 B1 | 4/2001 | Hultgren |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,299,438 B1 | 10/2001 | Sahagian et al. |
| 6,309,215 B1 | 10/2001 | Phan et al. |
| 6,315,553 B1 | 11/2001 | Sachdeva et al. |
| 6,328,745 B1 | 12/2001 | Ascherman |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,402,510 B1 | 6/2002 | Williams |
| 6,402,707 B1 | 6/2002 | Ernst |
| 6,405,729 B1 | 6/2002 | Thornton |
| 6,413,086 B1 | 7/2002 | Womack |
| 6,436,058 B1 | 8/2002 | Krahner et al. |
| 6,450,167 B1 | 9/2002 | David et al. |
| 6,450,807 B1 | 9/2002 | Chishti et al. |
| 6,482,298 B1 | 11/2002 | Bhatnagar |
| 6,499,995 B1 | 12/2002 | Schwartz |
| 6,515,593 B1 | 2/2003 | Stark et al. |
| 6,516,805 B1 | 2/2003 | Thornton |
| 6,520,772 B2 | 2/2003 | Williams |
| 6,524,101 B1 | 2/2003 | Phan et al. |
| 6,540,707 B1 | 4/2003 | Stark et al. |
| 6,572,372 B1 | 6/2003 | Phan et al. |
| 6,573,998 B2 | 6/2003 | Cohen Sabban |
| 6,594,539 B1 | 7/2003 | Geng |
| 6,597,934 B1 | 7/2003 | de Jong et al. |
| 6,602,070 B2 | 8/2003 | Miller et al. |
| 6,611,783 B2 | 8/2003 | Kelly et al. |
| 6,613,001 B1 | 9/2003 | Dworkin |
| 6,616,579 B1 | 9/2003 | Reinbold et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,640,128 B2 | 10/2003 | Vilsmeier et al. |
| 6,697,164 B1 | 2/2004 | Babayoff et al. |
| 6,702,765 B2 | 3/2004 | Robbins et al. |
| 6,702,804 B1 | 3/2004 | Ritter et al. |
| 6,705,863 B2 | 3/2004 | Phan et al. |
| 6,830,450 B2 | 12/2004 | Knopp et al. |
| 6,832,912 B2 | 12/2004 | Mao |
| 6,885,464 B1 | 4/2005 | Pfeiffer et al. |
| 6,890,285 B2 | 5/2005 | Rahman et al. |
| 7,036,514 B2 | 5/2006 | Heck |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,138,640 B1 | 11/2006 | Delgado et al. |
| 7,142,312 B2 | 11/2006 | Quadling et al. |
| 7,166,063 B2 | 1/2007 | Rahman et al. |
| 7,184,150 B2 | 2/2007 | Quadling et al. |
| 7,192,273 B2 | 3/2007 | McSurdy |
| 7,220,124 B2 | 5/2007 | Taub et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B2 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,724,378 B2 | 5/2010 | Babayoff |
| D618,619 S | 6/2010 | Walter |
| 7,731,508 B2 | 6/2010 | Borst |
| 7,735,217 B2 | 6/2010 | Borst |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy |
| 7,874,849 B2 | 1/2011 | Sticker et al. |
| 7,878,801 B2 | 2/2011 | Abolfathi et al. |
| 7,907,280 B2 | 3/2011 | Johs et al. |
| 7,929,151 B2 | 4/2011 | Liang et al. |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 8,017,891 B2 | 9/2011 | Nevin |
| 8,026,916 B2 * | 9/2011 | Wen .......... A61C 7/00 345/419 |
| 8,027,709 B2 | 9/2011 | Arnone et al. |
| 8,054,556 B2 | 11/2011 | Chen et al. |

(56) References Cited

U.S. PATENT DOCUMENTS

| | | |
|---|---|---|
| 8,070,490 B1 | 12/2011 | Roetzer et al. |
| 8,077,949 B2 | 12/2011 | Liang et al. |
| 8,083,556 B2 | 12/2011 | Stadler et al. |
| D652,799 S | 1/2012 | Mueller |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,870,566 B2 | 10/2014 | Bergersen |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rösch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,242,118 B2 | 1/2016 | Brawn |
| 9,261,358 B2 | 2/2016 | Atiya et al. |
| 9,336,336 B2 * | 5/2016 | Deichmann ......... A61C 13/0004 |
| 9,351,810 B2 | 5/2016 | Moon |
| 9,375,300 B2 | 6/2016 | Matov et al. |
| 9,408,743 B1 | 8/2016 | Wagner |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,500,635 B2 | 11/2016 | Islam |
| 9,506,808 B2 | 11/2016 | Jeon et al. |
| 9,545,331 B2 | 1/2017 | Ingemarsson-Matzen |
| 9,584,771 B2 | 2/2017 | Mandelis et al. |
| 9,675,430 B2 | 6/2017 | Verker et al. |
| 9,693,839 B2 | 7/2017 | Atiya et al. |
| 9,744,006 B2 | 8/2017 | Ross |
| 9,861,451 B1 | 1/2018 | Davis |
| 9,936,186 B2 * | 4/2018 | Jesenko ................. G06T 19/20 |
| 10,159,541 B2 | 12/2018 | Bindayel |
| 2001/0038705 A1 | 11/2001 | Rubbert et al. |
| 2002/0010568 A1 | 1/2002 | Rubbert |
| 2002/0015934 A1 * | 2/2002 | Rubbert ................. A61C 7/00 433/29 |
| 2003/0009252 A1 | 1/2003 | Pavlovskaia et al. |
| 2003/0035061 A1 | 2/2003 | Iwaki et al. |
| 2003/0139834 A1 | 7/2003 | Nikolskiy et al. |
| 2003/0190575 A1 | 10/2003 | Hilliard |
| 2003/0207224 A1 | 11/2003 | Lotte |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0058295 A1 | 3/2004 | Bergersen |
| 2004/0094165 A1 | 5/2004 | Cook |
| 2004/0158194 A1 | 8/2004 | Wolff et al. |
| 2004/0167646 A1 | 8/2004 | Jelonek et al. |
| 2005/0023356 A1 | 2/2005 | Wiklof et al. |
| 2005/0031196 A1 * | 2/2005 | Moghaddam ...... G06K 9/00288 382/154 |
| 2005/0037312 A1 | 2/2005 | Uchida |
| 2005/0048433 A1 | 3/2005 | Hilliard |
| 2005/0100333 A1 | 5/2005 | Kerschbaumer et al. |
| 2005/0181333 A1 | 8/2005 | Karazivan et al. |
| 2005/0186524 A1 | 8/2005 | Abolfathi et al. |
| 2005/0244781 A1 | 11/2005 | Abels et al. |
| 2006/0084024 A1 | 4/2006 | Farrell |
| 2006/0099546 A1 | 5/2006 | Bergersen |
| 2006/0154198 A1 | 7/2006 | Durbin et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2007/0046865 A1 | 3/2007 | Umeda et al. |
| 2007/0053048 A1 | 3/2007 | Kumar et al. |
| 2007/0087300 A1 | 4/2007 | Willison et al. |
| 2007/0106138 A1 | 5/2007 | Beiski et al. |
| 2007/0184402 A1 | 8/2007 | Boutoussov et al. |
| 2007/0231765 A1 | 10/2007 | Phan et al. |
| 2007/0238065 A1 | 10/2007 | Sherwood et al. |
| 2008/0045053 A1 | 2/2008 | Stadler et al. |
| 2008/0057461 A1 | 3/2008 | Cheng et al. |
| 2008/0090208 A1 | 4/2008 | Rubbert |
| 2008/0115791 A1 | 5/2008 | Heine |
| 2008/0176448 A1 | 7/2008 | Muller et al. |
| 2008/0242144 A1 | 10/2008 | Dietz |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0298017 A1 | 12/2009 | Boerjes et al. |
| 2009/0305540 A1 | 12/2009 | Stadler et al. |
| 2010/0019170 A1 | 1/2010 | Hart et al. |
| 2010/0045902 A1 | 2/2010 | Ikeda et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0231577 A1 | 9/2010 | Kim et al. |
| 2010/0312484 A1 | 12/2010 | DuHamel et al. |
| 2011/0012901 A1 | 1/2011 | Kaplanyan |
| 2011/0045428 A1 * | 2/2011 | Boltunov ............... A61C 7/002 433/24 |
| 2011/0081625 A1 | 4/2011 | Fuh |
| 2011/0102549 A1 * | 5/2011 | Takahashi ............. A61C 1/084 348/46 |
| 2011/0102566 A1 | 5/2011 | Zakian et al. |
| 2011/0143673 A1 | 6/2011 | Landesman et al. |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0081786 A1 | 4/2012 | Mizuyama et al. |
| 2012/0086681 A1 | 4/2012 | Kim et al. |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |

(56) References Cited

U.S. PATENT DOCUMENTS

| | | |
|---|---|---|
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0163627 A1 | 6/2013 | Seurin et al. |
| 2013/0201488 A1 | 8/2013 | Ishihara |
| 2013/0218531 A1* | 8/2013 | Deichmann ............ A61C 9/004 703/1 |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0280671 A1 | 10/2013 | Brawn et al. |
| 2013/0286174 A1* | 10/2013 | Urakabe ............ A61B 1/00009 348/66 |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0337412 A1 | 12/2013 | Kwon |
| 2014/0081091 A1 | 3/2014 | Abolfathi et al. |
| 2014/0122027 A1 | 5/2014 | Andreiko et al. |
| 2014/0272774 A1 | 9/2014 | Dillon et al. |
| 2014/0294273 A1* | 10/2014 | Jaisson ................ A61B 5/7425 382/131 |
| 2014/0313299 A1 | 10/2014 | Gebhardt et al. |
| 2014/0329194 A1 | 11/2014 | Sachdeva et al. |
| 2014/0363778 A1 | 12/2014 | Parker |
| 2015/0002649 A1 | 1/2015 | Nowak et al. |
| 2015/0079531 A1 | 3/2015 | Heine |
| 2015/0140502 A1 | 5/2015 | Brawn et al. |
| 2015/0164335 A1 | 6/2015 | Van Der Poel et al. |
| 2015/0173856 A1 | 6/2015 | Iowe et al. |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0325044 A1* | 11/2015 | Lebovitz ................ G06T 15/04 345/420 |
| 2015/0338209 A1 | 11/2015 | Knüttel |
| 2016/0000332 A1 | 1/2016 | Atiya et al. |
| 2016/0003610 A1 | 1/2016 | Lampert et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0296303 A1 | 10/2016 | Parker |
| 2016/0328843 A1 | 11/2016 | Graham et al. |
| 2017/0007366 A1 | 1/2017 | Kopelman et al. |
| 2017/0007367 A1 | 1/2017 | Li et al. |
| 2017/0156821 A1 | 6/2017 | Kopelman et al. |
| 2017/0215739 A1 | 8/2017 | Miyasato |
| 2017/0265970 A1 | 9/2017 | Verker |
| 2017/0325690 A1* | 11/2017 | Salah ...................... G06T 7/251 |
| 2017/0340411 A1 | 11/2017 | Akselrod |
| 2018/0000563 A1 | 1/2018 | Shanjani et al. |
| 2018/0000565 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0125610 A1 | 5/2018 | Carrier et al. |

FOREIGN PATENT DOCUMENTS

| | | |
|---|---|---|
| AU | 5598894 A | 6/1994 |
| CA | 1121955 A1 | 4/1982 |
| DE | 2749802 A1 | 5/1978 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2930334 A1 | 10/2009 |
| GB | 1550777 A | 8/1979 |
| JP | 53-058191 A | 5/1978 |
| JP | 4028359 A | 1/1992 |
| JP | 08-508174 A | 9/1996 |
| JP | 2007260158 A | 10/2007 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009205330 A | 9/2009 |
| JP | 2011087733 A | 5/2011 |
| JP | 2013007645 A | 1/2013 |
| JP | 201735173 A | 2/2017 |
| KR | 10-1266966 B1 | 5/2013 |
| KR | 10-2016-041632 A | 4/2016 |
| KR | 10-2016-0071127 A | 6/2016 |
| WO | WO91/004713 A1 | 4/1991 |
| WO | WO94/010935 A1 | 5/1994 |
| WO | WO98/032394 A1 | 7/1998 |
| WO | WO2002/017776 A2 | 3/2002 |
| WO | WO2002/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/133548 A1 | 12/2006 |
| WO | 2009085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2013/058879 A2 | 4/2013 |
| WO | WO2014/068107 A1 | 5/2014 |
| WO | WO2014/091865 A1 | 6/2014 |
| WO | WO2015/015289 A2 | 2/2015 |
| WO | 2015063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |

(56) References Cited

FOREIGN PATENT DOCUMENTS

WO WO2016/116874 A1 7/2016
WO WO2017/006176 A1 1/2017

OTHER PUBLICATIONS

Grest, Daniel, "Marker-Free Human Motion capture in Dynamic Cluttered Environments for a Single View-Point, PhD thesis," Jan. 1, 2007; pp. 1-171.
Doruk et al.; The role of the headgear timer in extraoral co-operation; European Journal of Orthodontics; 26; pp. 289-291; Jun. 1, 2004.
Friedrich et al; Measuring system for in vivo recording of force systems in orthodontic treatment-concept and analysis of accuracy; J. Biomech.; 32(1); pp. 81-85; (Abstract Only) Jan. 1999.
Invisalign; You were made to move. There's never been a better time to straighten your teeth with the most advanced clear aligner in the world; Product webpage; 2 pages; retrieved from the Internet (www.invisalign.com/) on Dec. 28, 2017.
Kumar et al.; Rapid maxillary expansion: A unique treatment modality in dentistry; J. Clin. Diagn. Res.; 5(4); pp. 906-911; Aug. 2011.
Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.
Sahm; Presentation of a wear timer for the clarification of scientific questions in orthodontic orthopedics; Fortschritte der Kieferorthopadie; 51 (4); pp. 243-247; (Translation Included) Jul. 1990.
Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Thera Mon; "Microsensor"; 2 pages; retrieved from the internet (www.english.thera-mon.com/the-product/transponder/index.html); on Sep. 19, 2016.
Wikipedia; Palatal expansion; 3 pages; retrieved from the internet (https://en.wikipedia.org/wiki/Palatal_expansion) on Mar. 5, 2018.
Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Yamada et al.; Simulation of fan-beam type optical computed-tomography imaging of strongly scattering and weakly absorbing media; Applied Optics; 32(25); pp. 4808-4814; Sep. 1, 1993.
Sahm et al.; "Micro-Electronic Monitoring of Functional Appliance Wear"; Eur J Orthod.; 12(3); pp. 297-301; Aug. 1990.
Kuo; U.S. Appl. No. 15/829,504 entitled "Dental appliance features for speech enhancement," filed Dec. 1, 2017.
Atiya et al.; U.S. Appl. No. 15/859,010 entitled "Compact confocal dental scanning apparatus," filed Dec. 29, 2017.
Shanjani et al.; U.S. Appl. No. 15/831,159 entitled "Palatal expanders and methods of expanding a palate," filed Dec. 4, 2017.
Wu et al.; U.S. Appl. No. 15/831,262 entitled "Methods and apparatuses for customizing a rapid palatal expander," filed Dec. 4, 2017.
Grove et al.; U.S. Appl. No. 15/726,243 entitled "Interproximal reduction templates," filed Oct. 5, 2017.
AADR. American Association for Dental Research; Summary of Activities; Los Angeles, CA; p. 195; Mar. 20-23,(year of pub. sufficiently earlier than effective US filing date and any foreign priority date) 1980.
Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.
Alexander et al.; The DigiGraph Work Station Part 2 Clinical Management; J. Clin. Orthod.; pp. 402-407; (Author Manuscript); Jul. 1990.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Allesee Orthodontic Appliance: Important Tip About Wearing the Red White & Blue Active Clear Retainer System; Allesee Orthodontic Appliances-Pro Lab; 1 page; (year of pub. sufficiently earlier than effective US filing date and any foreign priority date); 1998.
Allesee Orthodontic Appliances: DuraClearTM; Product information; 1 page; (year of pub. sufficiently earlier than effective US filing date and any foreign priority date) 1997.
Allesee Orthodontic Appliances; The Choice Is Clear: Red, White & Blue . . . The Simple, Affordable, No-Braces Treatment; (product information for doctors); retrieved from the internet (http://ormco.com/aoa/appliancesservices/RWB/doctorhtml); 5 pages on May 19, 2003.
Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment:(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

(56) References Cited

OTHER PUBLICATIONS

Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.

Baumrind; Integrated Three-Dimensional Craniofacial Mapping: Background, Principles, and Perspectives; Seminars in Orthodontics; 7(4); pp. 223-232; Dec. 2001.

Begole et al.; A Computer System for the Analysis of Dental Casts; The Angle Orthodontist; 51(3); pp. 252-258; Jul. 1981.

Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988,.

Bhatia et al.; A Computer-Aided Design for Orthognathic Surgery; British Journal of Oral and Maxillofacial Surgery; 22(4); pp. 237-253; Aug. 1, 1984.

Biggerstaff et al.; Computerized Analysis of Occlusion in the Postcanine Dentition; American Journal of Orthodontics; 61(3); pp. 245-254; Mar. 1972.

Biggerstaff; Computerized Diagnostic Setups and Simulations; Angle Orthodontist; 40(I); pp. 28-36; Jan. 1970.

Biostar Operation & Training Manual. Great Lakes Orthodontics, Ltd. 199 Fire Tower Drive, Tonawanda, New York. 14150-5890, 20 pages; (year of pub. sufficiently earlier than effective US filing date and any foreign priority date) 1990.

Blu et al.; Linear interpolation revitalized; IEEE Transactions on Image Processing; 13(5); pp. 710-719; May 2004.

Bourke, Coordinate System Transformation; 1 page; retrived from the internet (http://astronomy.swin.edu.au/' pbourke/prolection/coords) on Nov. 5, 2004; Jun. 1996.

Boyd et al.; Three Dimensional Diagnosis and Orthodontic Treatment of Complex Malocclusions With the Invisalipn Appliance; Seminars in Orthodontics; 7(4); pp. 274-293; Dec. 2001.

Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.

Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.

Burstone et al.; Precision Adjustment of the Transpalatal Lingual Arch: Computer Arch Form Predetermination; American Journal of Orthodontics; 79(2);pp. 115-133; Feb. 1981.

Burstone; Dr. Charles J. Burstone on The Uses of the Computer in Orthodontic Practice (Part 1); Journal of Clinical Orthodontics; 13(7); pp. 442-453; (interview); Jul. 1979.

Burstone; Dr. Charles J. Burstone on The Uses of the Computer in Orthodontic Practice (Part 2); journal of Clinical Orthodontics; 13(8); pp. 539-551 (interview); Aug. 1979.

Cardinal Industrial Finishes; Powder Coatings; 6 pages; retrieved from the internet (http://www.cardinalpaint.com) on Aug. 25, 2000,.

Carnaghan, An Alternative to Holograms for the Portrayal of Human Teeth; 4th Int'l. Conf. on Holographic Systems, Components and Applications; pp. 228-231; Sep. 15, 1993.

Chaconas et al,; The DigiGraph Work Station, Part 1, Basic Concepts; Journal of Clinical Orthodontics; 24(6); pp. 360-367; (Author Manuscript); Jun. 1990.

Chafetz et al.; Subsidence of the Femoral Prosthesis, A Stereophotogrammetric Evaluation; Clinical Orthopaedics and Related Research; No. 201; pp. 60-67; Dec. 1985.

Chiappone; Constructing the Gnathologic Setup and Positioner; Journal of Clinical Orthodontics; 14(2); pp. 121-133; Feb. 1980.

Chishti et al.; U.S. Appl. No. 60/050,342 entitled "Procedure for moving teeth using a seires of retainers," filed Jun. 20, 1997.

CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.

Cottingham; Gnathologic Clear Plastic Positioner; American Journal of Orthodontics; 55(1); pp. 23-31; Jan. 1969.

Crawford; CAD/CAM in the Dental Office: Does It Work?; Canadian Dental Journal; 57(2); pp. 121-123 Feb. 1991.

Crawford; Computers in Dentistry: Part 1: CAD/CAM: The Computer Moves Chairside, Part 2: F. Duret ' A Man With A Vision, Part 3: The Computer Gives New Vision'Literally, Part 4: Bytes 'N Bites The Computer Moves From The Front Desk To The Operatory; Canadian Dental Journal; 54(9); pp. 661-666 Sep. 1988.

Crooks; CAD/CAM Comes to USC; USC Dentistry; pp. 14-17; (year of pub. sufficiently earlier than effective US filing date and any foreign priority date) Spring 1990.

Cureton; Correcting Malaligned Mandibular Incisors with Removable Retainers; Journal of Clinical Orthodontics; 30(7); pp. 390-395; Jul. 1996.

Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.

Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.

DCS Dental AG; The CAD/CAM 'DCS Titan System' for Production of Crowns/Bridges; DSC Production; pp. 1-7; Jan. 1992.

Defranco et al.; Three-Dimensional Large Displacement Analysis of Orthodontic Appliances; Journal of Biomechanics; 9(12); pp. 793-801; Jan. 1976.

Dental Institute University of Zurich Switzerland; Program for International Symposium on Computer Restorations: State of the Art of the CEREC-Method; 2 pages; May 1991.

Dentrac Corporation; Dentrac document; pp. 4-13; (year of pub. sufficiently earlier than effective US filing date and any foreign priority date) 1992.

Dent-X; Dentsim . . . Dent-x's virtual reality 3-D training simulator . . . A revolution in dental education; 6 pages; retrieved from the Internet (http://www.dent-x.com/DentSim.htm); on Sep. 24, 1998.

Di Muzio et al.; Minimum intensity projection (MinIP); 6 pages; retrieved from the internet (https://radiopaedia.org/articles/minimum-intensity-projection-minip) on Sep. 6, 2018.

Doyle; Digital Dentistry; Computer Graphics World; pp. 50-52 and p. 54; Oct. 2000.

Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.

Duret et al.; CAD/CAM Imaging in Dentistry; Current Opinion in Dentistry; 1 (2); pp. 150-154; Apr. 1991.

Duret et al; CAD-CAM in Dentistry; Journal of the American Dental Association; 117(6); pp. 715-720; Nov. 1988.

Duret; The Dental CAD/CAM, General Description of the Project; Hennson International Product Brochure, 18 pages; Jan. 1986.

Duret; Vers Une Prosthese Informatisee; Tonus; 75(15); pp. 55-57; (English translation attached); 23 pages; Nov. 15, 1985.

Economides; The Microcomputer in the Orthodontic Office; Journal of Clinical Orthodontics; 13(11); pp. 767-772; Nov. 1979.

Ellias et al.; Proteomic analysis of saliva identifies potential biomarkers for orthodontic tooth movement; The Scientific World Journal; vol. 2012; Article ID 647240; dio:10.1100/2012/647240; 7 pages; (year of pub. sufficiently earlier than effective US filing date and any foreign priority date) 2012.

Elsasser; Some Observations on the History and Uses of the Kesling Positioner; American Journal of Orthodontics; 36(5); pp. 368-374; May 1, 1950.

English translation of Japanese Laid-Open Publication No. 63-11148 to inventor T. Ozukuri (Laid-Open on Jan. 18, 1998) pp. 1-7.

Faber et al.; Computerized Interactive Orthodontic Treatment Planning; American Journal of Orthodontics; 73(1); pp. 36-46; Jan. 1978.

(56) References Cited

OTHER PUBLICATIONS

Felton et al.; A Computerized Analysis of the Shape and Stability of Mandibular Arch Form; American Journal of Orthodontics and Dentofacial Orthopedics; 92(6); pp. 478-483; Dec. 1987.

Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.

Friede et al.; Accuracy of Cephalometric Prediction in Orthognathic Surgery; Journal of Oral and Maxillofacial Surgery; 45(9); pp. 754-760; Sep. 1987.

Futterling et al.; Automated Finite Element Modeling of a Human Mandible with Dental Implants; JS WSCG '98-Conference Program; 8 pages; retrieved from the Internet (https://dspace5.zcu.cz/bitstream/11025/15851/1/Strasser_98.pdf); on Aug. 21, 2018.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

Gim-Alldent Deutschland, "Das DUX System: Die Technik," 3 pages; (English Translation Included); (year of pub. sufficiently earlier than effective US filing date and any foreign priority date); 2002.

Gottlieb et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Guess et al.; Computer Treatment Estimates in Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa..); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987,.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

JCO Interviews; Craig Andreiko, DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kleeman et al.; The Speed Positioner; J. Clin. Orthod.; 30(12); pp. 673-680; Dec. 1996.

Kochanek; Interpolating Splines with Local Tension, Continuity and Bias Control; Computer Graphics; 18(3); pp. 33-41; Jan. 1, 1984.

Kunii et al.; Articulation Simulation for an Intelligent Dental Care System; Displays; 15(3); pp. 181-188; Jul. 1994.

Kuroda et al.; Three-Dimensional Dental Cast Analyzing System Using Laser Scanning; American Journal of Orthodontics and Dentofacial Orthopedics; 110(4); pp. 365-369; Oct. 1996.

Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.

Leinfelder et al.; A New Method for Generating Ceramic Restorations: a CAD-CAM System; Journal of the American Dental Association; 118(6); pp. 703-707; Jun. 1989.

Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.

McCann; Inside the ADA; J. Amer. Dent. Assoc, 118:286-294; Mar. 1989.

McNamara et al.; Invisible Retainers; J. Clin Orthod.; pp. 570-578; 11 pages; (Author Manuscript); Aug. 1985.

McNamara et al.; Orthodontic and Orthopedic Treatment in the Mixed Dentition; Needham Press; pp. 347-353; Jan. 1993.

Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.

Moles; Correcting Mild Malalignments—As Easy As One, Two, Three; AOA/Pro Corner; 11(2); 2 pages; (year of pub. sufficiently earlier than effective US filing date and any foreign priority date) 2002.

Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.

Nahoum; The Vacuum Formed Dental Contour Appliance; N. Y. State Dent. J.; 30(9); pp. 385-390; Nov. 1964.

Nash; CEREC CAD/CAM Inlays: Aesthetics and Durability in a Single Appointment; Dentistry Today; 9(8); pp. 20, 22-23 and 54; Oct. 1990.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Ogawa et al.; Mapping, profiling and clustering of pressure pain threshold (PPT) in edentulous oral muscosa; Journal of Dentistry; 32(3); pp. 219-228; Mar. 2004.

(56) References Cited

OTHER PUBLICATIONS

Ogimoto et al.; Pressure-pain threshold determination in the oral mucosa; Journal of Oral Rehabilitation; 29(7); pp. 620-626; Jul. 2002.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages, Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording The Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210, 309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the Internet (http://www.jco-online.com/archive/print_article.asp?Year=1992&Month=06&ArticleNum=); Jun. 1992.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-8; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models'An Introduction; Computer-Aided Design; 29(4); pp. 255-268; 20 pages; (Author Manuscript); Apr. 1997.

(56) References Cited

OTHER PUBLICATIONS

Verstreken et al.; An Image-Guided Planning System for Endosseous Oral Implants; IEEE Transactions on Medical Imaging; 17(5); pp. 842-852; Oct. 1998.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23 (10); pp. 694-700; Oct. 1989.
Watson et al.; Pressures recorded at te denture base-mucosal surface interface in complete denture wearers; Journal of Oral Rehabilitation 14(6); pp. 575-589; Nov. 1987.
Wells; Application of the Positioner Appliance in Orthodontic Treatment; American Journal of Orthodontics; 58(4); pp. 351-366; Oct. 1970.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.
Wolf; Three-dimensional structure determination of semi-transparent objects from holographic data; Optics Communications; 1(4); pp. 153-156; Sep. 1969.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998,.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Cramer; U.S. Appl. No. 15/937,569 entitled "Apparatuses and methods assisting in dental therapies," filed Mar. 27, 2018.
Cramer et al.; U.S. Appl. No. 15/942,341 entitled "Orthodontic appliances including at least partially un-erupted teeth and method of forming them," filed Mar. 30, 2018.
Riley et al.; U.S. Appl. No. 16/003,841 entitled Palatal expander with skeletal anchorage devices, filed Jun. 8, 2018.
Shanjani et al.; U.S. Appl. No. 16/019,037 entitled "Biosensor performance indicator for intraoral appliances," filed Jun. 26, 2018.
Sato et al.; U.S. Appl. No. 16/041,606 entitled "Palatal contour anchorage," filed Jul. 20, 2018.
Xue et al.; U.S. Appl. No. 16/010,087 entitled "Automatic detection of tooth type and eruption status," filed Jun. 15, 2018.
Sato et al.; U.S. Appl. No. 16/048,054 entitled "Optical coherence tomography for orthodontic aligners," filed Jul. 27, 2018.
Miller et al.; U.S. Appl. No. 16/038,088 entitled "Method and apparatuses for interactive ordering of dental aligners," filed Jul. 17, 2018.
Moalem et al.; U.S. Appl. No. 16/046,897 entitled Tooth shading, transparency and glazing, filed Jul. 26, 2018.
Nyukhtikov et al.; U.S. Appl. No. 15/998,883 entitled "Buccal corridor assessment and computation," filed Aug. 15, 2018.

* cited by examiner $$(X,Y,Z) \overset{h}{\underset{h^{-1}}{\rightleftarrows}} (kX, kY, kZ, k)$$

$$\mathbf{w} = \begin{bmatrix} X \\ Y \\ Z \end{bmatrix}$$

$$\mathbf{w}_h = \begin{bmatrix} kX \\ kY \\ kZ \\ k \end{bmatrix}$$

$$\mathbf{P} = \begin{bmatrix} 1 & 0 & 0 & 0 \\ 0 & 1 & 0 & 0 \\ 0 & 0 & 1 & 0 \\ 0 & 0 & \frac{-1}{r} & 1 \end{bmatrix}$$

$$\mathbf{P}^{-1} = \begin{bmatrix} 1 & 0 & 0 & 0 \\ 0 & 1 & 0 & 0 \\ 0 & 0 & 1 & 0 \\ 0 & 0 & \frac{-1}{r} & 1 \end{bmatrix}$$

$$\begin{bmatrix} kx \\ ky \\ kz \\ k \end{bmatrix} = \mathbf{c}_h = \mathbf{P}\mathbf{w}_h = \begin{bmatrix} 1 & 0 & 0 & 0 \\ 0 & 1 & 0 & 0 \\ 0 & 0 & 1 & 0 \\ 0 & 0 & \frac{-1}{r} & 1 \end{bmatrix} \begin{bmatrix} kX \\ kY \\ kZ \\ k \end{bmatrix} = \begin{bmatrix} kX \\ kY \\ kZ \\ \frac{-kZ}{r} + k \end{bmatrix} \underset{\rightarrow}{h^{-1}} \begin{bmatrix} \frac{rX}{r-Z} \\ \frac{rY}{r-Z} \\ \frac{rZ}{r-Z} \end{bmatrix} = \mathbf{c} = \begin{bmatrix} x \\ y \\ z \end{bmatrix}$$

$$\mathbf{w}_h = \mathbf{P}^{-1}\mathbf{c}_h$$

$$\mathbf{c} = \begin{bmatrix} x_0 \\ y_0 \\ 0 \end{bmatrix} \leftrightarrow \begin{bmatrix} X \\ Y \\ 0 \end{bmatrix} = \mathbf{w}$$

FIG. 3C $$T_{w_0} = \begin{bmatrix} 1 & 0 & 0 & -X_0 \\ 0 & 1 & 0 & -Y_0 \\ 0 & 0 & 1 & -Z_0 \\ 0 & 0 & 0 & 1 \end{bmatrix} \text{—370}$$

$$R = R_\alpha R_\theta = \begin{bmatrix} \cos\theta & \sin\theta & 0 & 0 \\ -\sin\theta\sin\alpha & \cos\theta\cos\alpha & \sin\alpha & 0 \\ \sin\theta\sin\alpha & -\cos\theta\sin\alpha & \cos\alpha & 0 \\ 0 & 0 & 0 & 1 \end{bmatrix} \text{—372}$$

$$C = \begin{bmatrix} 1 & 0 & 0 & -r_1 \\ 0 & 1 & 0 & -r_2 \\ 0 & 0 & 1 & -r_3 \\ 0 & 0 & 0 & 1 \end{bmatrix} \text{—374}$$

$c_h = P\,C\,R\,T_{w_0}\,w_h$ —376

$w_h = T_{w_0}^{-1}\,R^{-1}\,C^{-1}\,P^{-1}\,c_h$ —378

$(x, z) = f(X, Y, Z, \text{camera\_parameters})$ —380

$(X, Y, Z) = f^{-1}(x, z, \text{camera\_parameters})$ —381

FIG. 3D

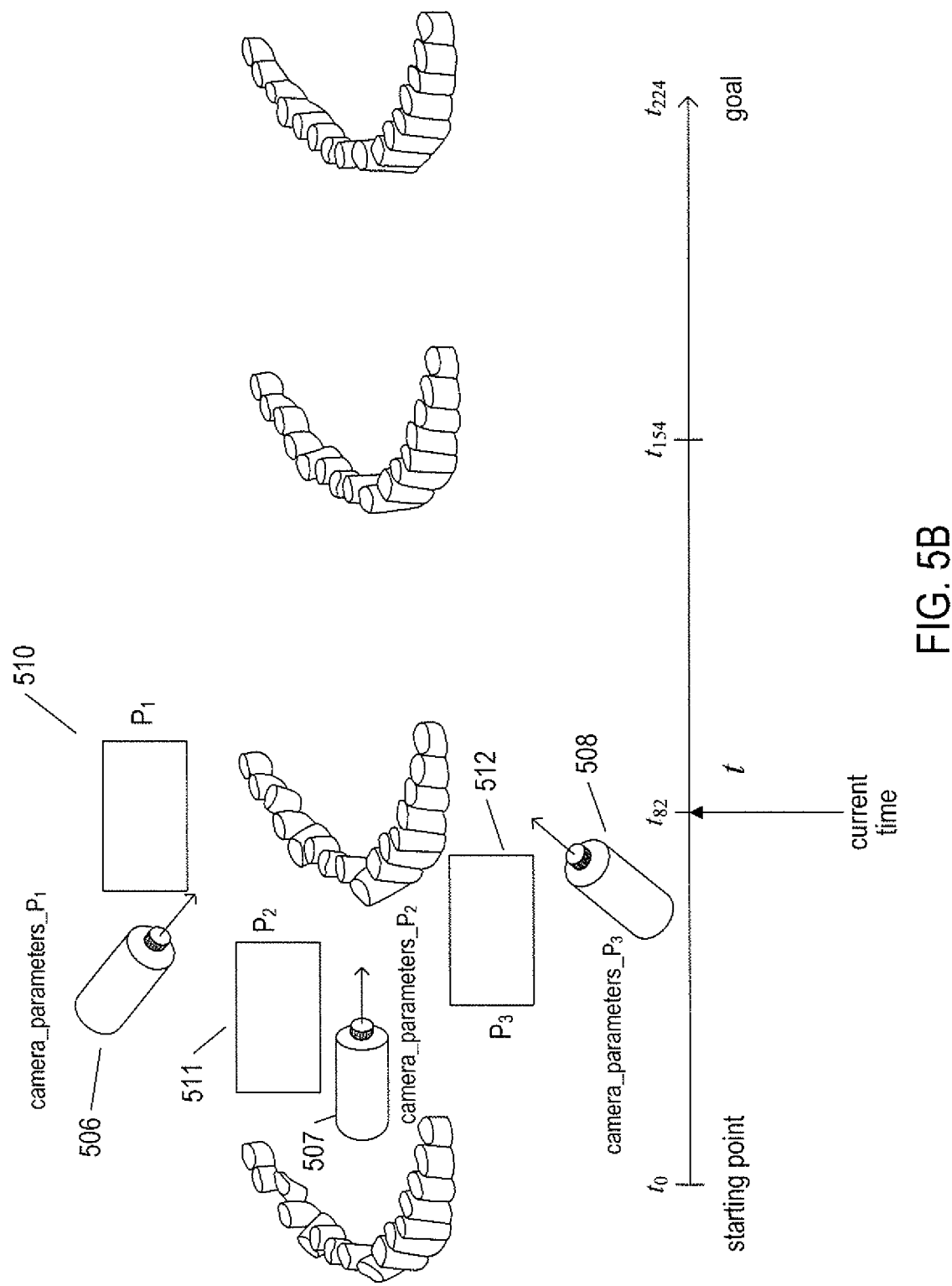

$$p(\mathbf{I}_1(\cdot,\cdot)=i)=p_{1,i}$$

$$p(\mathbf{I}_2(\cdot,\cdot)=i)=p_{2,i}$$

$$p(\mathbf{I}_1(\cdot,\cdot)=i,\mathbf{I}_2(\cdot,\cdot)=j)=p_{1,2,i,j}$$
— 1350

$$H_1 = \sum_i p_{1,i} \log\left(\frac{1}{p_{1,i}}\right) = -\sum_i p_{1,i} \log p_{1,i}$$

$$H_2 = \sum_i p_{2,i} \log\left(\frac{1}{p_{2,i}}\right) = -\sum_i p_{2,i} \log p_{2,i}$$

$$H_{1,2} = -\sum_{i,j} p_{1,2,i,j} \log p_{1,2,i,j}$$
— 1352

$$\mathrm{MI}(\mathbf{I}_1,\mathbf{I}_2) = H_1 + H_2 - H_{1,2}$$ — 1354

$$\mathrm{cost}(\mathbf{I}_1,\mathbf{I}_2) = -\mathrm{MI}(\mathbf{I}_1,\mathbf{I}_2) * G(\mathbf{I}_1,\mathbf{I}_2)$$ — 1356

$$G(\mathbf{I}_1,\mathbf{I}_2) = \sum_{x,y} f\left(\nabla \mathbf{I}_{1(x,y)}, \nabla \mathbf{I}_{2(x,y)}, \mathrm{TM}_{(x,y)}\right)$$ — 1358

$$f(\mathbf{a},\mathbf{b},c) = \begin{cases} \cos(\mathbf{a},\mathbf{b}) * \sqrt{\min(|\mathbf{a}|,|\mathbf{b}|)}, & \text{when } c \in \text{teeth} \\ 0, & \text{when } c \notin \text{teeth} \end{cases}$$ — 1360

FIG. 13C example groups:

[9, 8, 9, 10]
[6, 7, 8, 9]
[5, 6, 7, 8]
[4, 5, 6, 7, 8]
[3, 4, 5, 6, 7]
[2, 3, 4, 5, 6, 7]

$$\mathrm{cost}(x,y) \begin{cases} \frac{\nabla \mathbf{I}_s \cdot \nabla \mathbf{I}_p}{|\nabla \mathbf{I}_s| \cdot |\nabla \mathbf{I}_p|} & \text{when } |\nabla \mathbf{I}_s| \text{ and } |\nabla \mathbf{I}_p| > T \\ 0, & \text{otherwise} \end{cases} \bigg/ 1720$$

$$\text{fitness 1} = \frac{1}{|\text{contour}|} \sum_{x,y \in \text{contour}} \text{cost}(x,y) \quad / 1722$$

$$\text{fitness 2} = \sum_{x,y \in \text{contour}} \max_{t,s,\in \varepsilon_{x,y}} \text{cost}(t,s) \quad / 1724$$

FIG. 17B

PHOTOGRAPH-BASED ASSESSMENT OF DENTAL TREATMENTS AND PROCEDURES

TECHNICAL FIELD

The current document is directed to methods and systems for monitoring patient progress during dental treatments and procedures and, in particular, to a photograph-based monitoring method, and system that carries out the method, that uses two-dimensional photographs taken during a patient examination to determine how well the patient's teeth correspond to a three-dimensional representation of the expected positions of patient's teeth according to the treatment plan.

BACKGROUND

Prior to the development of oral-cavity-imaging-and-modeling systems, dental practitioners employed mechanical-impression methods to create three-dimensional models of teeth and underlying tissue in order to facilitate fabrication of various types of prostheses, including crowns and bridges. The mechanical-impression technologies generally involved biting, by a patient, into a viscous, thixotropic material that retains an accurate impression of the patient's teeth and underlying tissue when the material is lifted off from the patient's teeth. The material may serve as a mold for casting a positive three-dimensional model of the patient's teeth and underlying gum tissue or as a mold for casting a prosthetic device. While mechanical-impression technologies have been used by dental practitioners for many decades, mechanical-impression technologies are associated with a variety of deficiencies, including a relatively large probability that the impression may be inadvertently altered or damaged during removal of the hardened, viscous, thixotropic material from the patient's teeth as well as during transportation of the impression to laboratories where positive three-dimensional models are cast and prostheses are fabricated. In addition, the procedure is time-consuming and unpleasant to many patients.

More recently, semi-automated oral-cavity-imaging-and-modeling systems have been developed to electronically create digital, three-dimensional models of teeth and underlying tissues from images of a patient's oral cavity captured by an electro-optical-mechanical endoscope, or wand, that is guided by a technician within a patient's oral cavity in order to collect a sufficient number of two-dimensional images from which a three-dimensional digital model of the patient's teeth and underlying tissues is computationally generated. The oral-cavity-imaging-and-modeling systems have proven to be faster, more accurate and robust, and more cost effective than mechanical-impression technologies.

In many cases, therefore, dental professionals can prepare accurate, three-dimensional models of a patient's teeth and use the three-dimensional models to analyze the patient's dental status and develop treatment plans for various types of deficiencies and pathologies. Furthermore, the three-dimensional model can be electronically manipulated to prepare projected three-dimensional configurations of the patient's teeth for various time points during the course of a treatment plan. Vendors of dental equipment, dental practitioners, and, ultimately, dental patients seek cost-effective and time-effective methods and systems to use the three-dimensional information in order to monitor a dental patient's progress during a course of treatment.

SUMMARY

The current document is directed to methods and systems for monitoring a dental patient's progress during a course of treatment. At any particular point in time during the course of treatment, a three-dimensional model of the expected positions of the patient's teeth at that point in time can be projected, in time, from a three-dimensional model of the patient's teeth prepared prior to beginning the treatment. During the course of treatment, a digital camera is used to take one or more two-dimensional photographs of the patient's teeth which are input to a monitoring system. The input two-dimensional photographs represent the actual positions of the patient's teeth. The monitoring system determines virtual-camera parameters for each two-dimensional input image with respect to the projected three-dimensional model and uses the determined virtual-camera parameters to generate two-dimensional images from the three-dimensional model. The generated two-dimensional photographs represent the expected or desired positions of the patient's teeth. The monitoring system then compares each input photograph to the corresponding generated two-dimensional image in order to determine how closely the three-dimensional arrangement of the patient's teeth corresponds to the projected three-dimensional arrangement. When the correspondence falls below a threshold level, an indication that the treatment is not proceeding according to plan is returned to a dental practitioner so that the dental practitioner can take corrective actions.

BRIEF DESCRIPTION OF THE DRAWINGS

FIGS. 3A-D illustrate one approach to mapping points in the world coordinate system to corresponding points on the image plane of a virtual camera.

FIGS. 5A-D graphically illustrate the treatment-monitoring method to which the current document is, in part, directed.

FIGS. 13A-C illustrate computation of a gradient-based cost.

FIGS. 17A-B illustrate computation of the comparison value or correlation coefficient.

DETAILED DESCRIPTION

Figure 1:
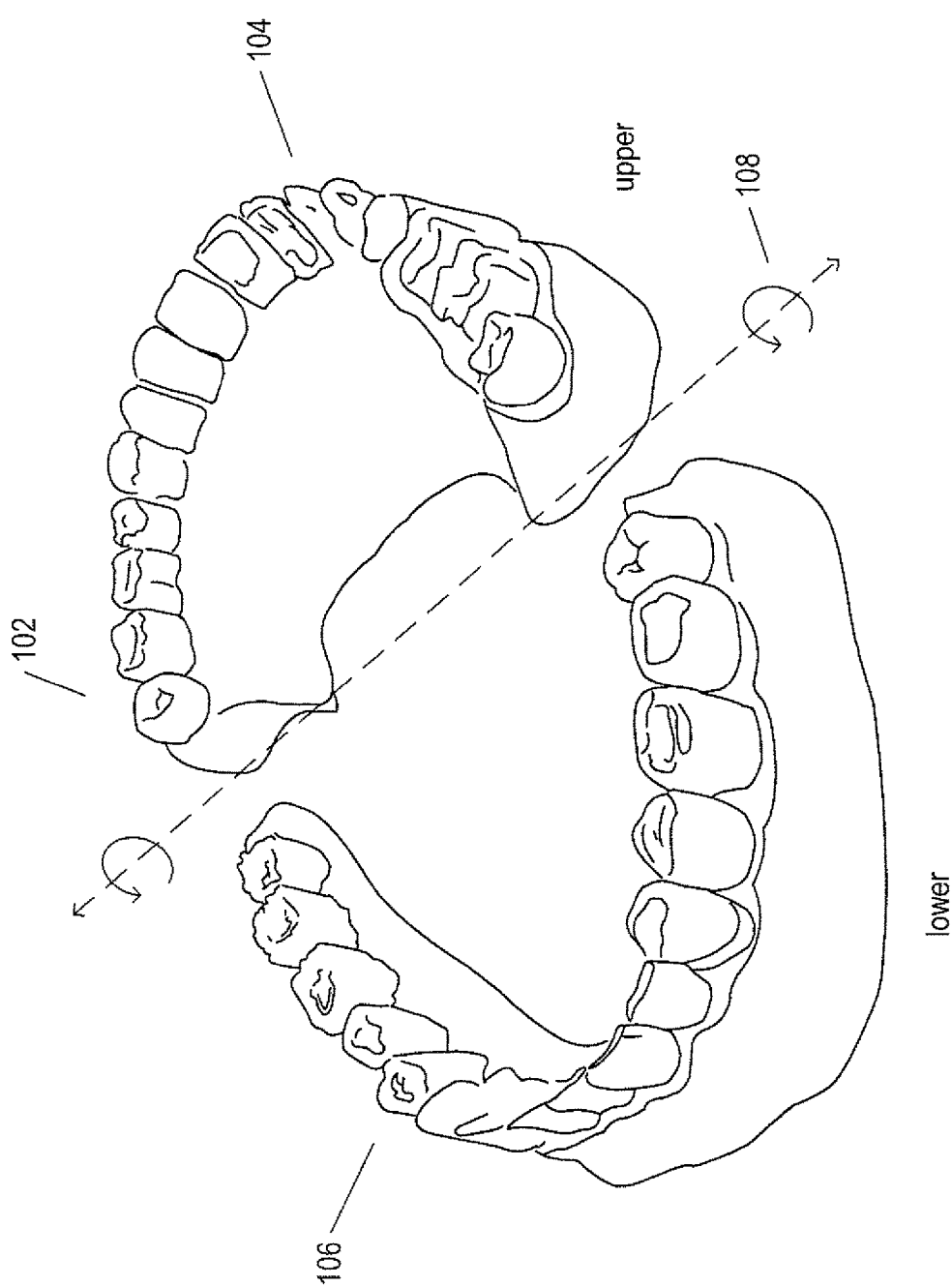
FIG. 1 illustrates a three-dimensional model of a dental patient's teeth.

FIG. 1 illustrates a three-dimensional model of a dental patient's teeth. The three-dimensional model 102 includes a three-dimensional model of the teeth associated with the dental patient's upper jaw 104 and a three-dimensional model of the dental patient's teeth associated with the lower jaw 106. The three-dimensional model is generally prepared, using sophisticated imaging and reconstruction hardware and software, based on optical scans of the dental patient's oral cavity. The three-dimensional model may be electronically represented in many different ways, similar to the many different ways in which three-dimensional objects may be represented in various different types of CAD/CAM and various imaging and solid-modeling systems. The model may be electronically presented in a variety of different orientations and configurations. For example, the two jaws 104 and 106 may be rotated about rotation axis 108 so that the teeth associated with the two jaws close together and assume a configuration similar to that in patient with a closed mouth. Each jaw and associated teeth may be, alternatively presented as a separate three-dimensional model.

Figure 2A:
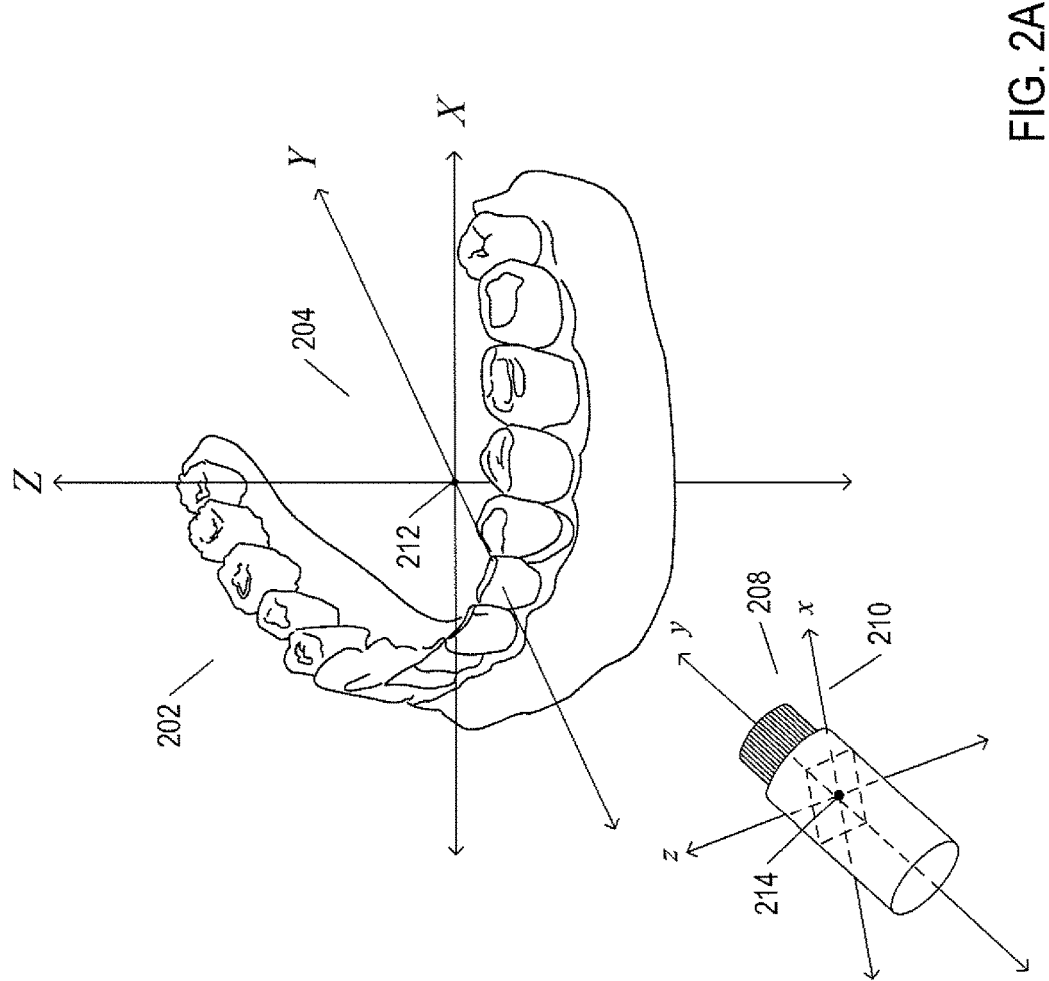
FIGS. 2A-B illustrate the relationship between a virtual-camera position and a three-dimensional model of a patient's teeth.
Figure 2B:
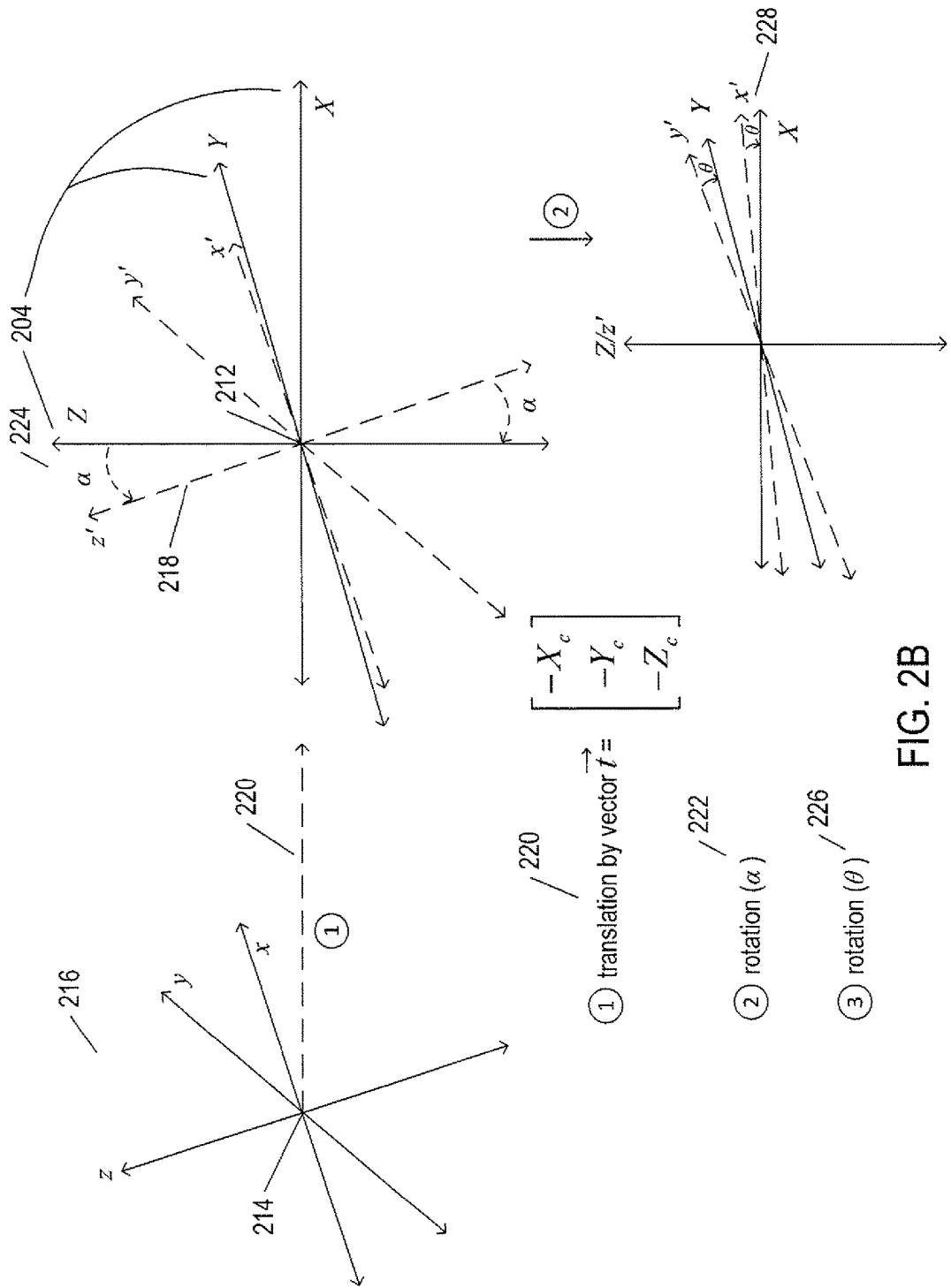

FIGS. 2A-B illustrate the relationship between a virtual-camera position and a three-dimensional model of a patient's teeth. As shown in FIG. 2A, the three-dimensional model of the dental patient's teeth 202 is translationally and rotationally positioned within a three-dimensional world coordinate system 204 having three mutually orthogonal axes X, Y, and Z. A two-dimensional view of the three-dimensional model can be obtained, from any position within the world coordinate system external to the three-dimensional model, by simulated image capture using a virtual camera 208. The virtual camera 208 is associated with its own three-dimensional coordinate system 210 having three mutually orthogonal axes x, y, and z. The world coordinate system and the camera coordinate system are, of course, mathematically related by a translation of the origin of the camera x, y, z coordinate system from the origin 212 of the world coordinate system and by three rotation angles that, when applied to the camera, rotate the camera x, y, and z coordinate system with respect to the world X, Y, Z coordinate system. The origin 214 of the camera x, y, z coordinate system has the coordinates (0, 0, 0) in the camera coordinate system and the coordinates ($X_c$, $Y_c$, and $Z_c$) in the world coordinate system. The two-dimensional image captured by the virtual camera 216 can be thought of as lying in the x, z plane of the camera coordinate system and centered at the origin of the camera coordinate system, as shown in FIG. 2.

FIG. 2B illustrates operations involved with orienting and positioning the camera x, y, z coordinate system to be coincident with the world X, Y, Z coordinate system. In FIG. 2B, the camera coordinate system 216 and world coordinate system 204 are centered at two different origins, 214 and 212, respectively, and the camera coordinate system is oriented differently than the world coordinate system. In order to orient and position the camera x, y, z coordinate system to be coincident with the world X, Y, Z coordinate system, three operations are undertaken. A first operation 220 involves translation of the camera-coordinate system, by a displacement represented by a vector t, so that the origins 214 and 212 of the two coordinate systems are coincident. The position of the camera coordinate system with respect to the world coordinate system is shown with dashed lines, including dashed line 218, with respect to the world coordinate system following the translation operation 220. A second operation 222 involves rotating the camera coordinate system by an angle α (224) so that the z axis of the camera coordinate system, referred to as the z' axis following the translation operation, is coincident with the Z axis of the world coordinate system. In a third operation 226, the camera coordinate system is rotated about the Z/i axis by an angle θ (228) so that all of the camera-coordinate-system axes are coincident with their corresponding world-coordinate-system axes.

Figure 3A:
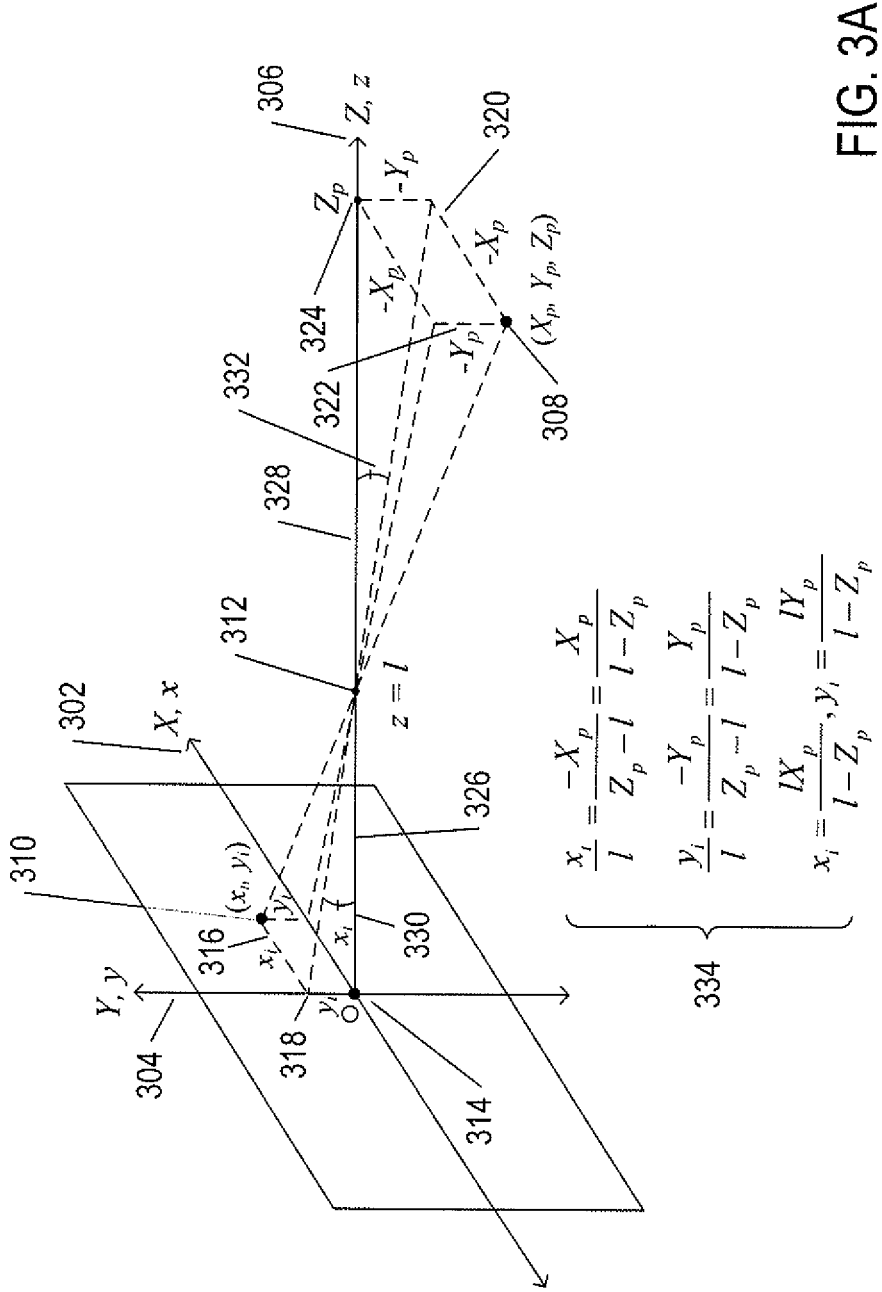

FIGS. 3A-D illustrate one approach to mapping points in the world coordinate system to corresponding points on the image plane of a virtual camera. This process allows virtual cameras to be positioned anywhere within space with respect to a computational three-dimensional model of a patient's teeth and used to generate a two-dimensional image that corresponds to the two-dimensional image that would be captured from a real camera having the same position and orientation with respect to an equivalent solid-model three-dimensional representation of a patient's teeth. FIG. 3A illustrates the image plane of a virtual camera, an aligned camera coordinate system and world coordinate system, and a point in three-dimensional space that is imaged on the image plane of the virtual camera. In FIG. 3A, and in FIGS. 3B-D that follow, the camera coordinate system, comprising the x, y, and z axes, is aligned and coincident with the world-coordinate system X, Y, and Z. This is indicated, in FIG. 3A, by dual labeling of the x and X axis 302, the y and Y axis 304, and the z and Z axis 306. The point that is imaged 308 is shown to have the coordinates ($X_p$, $Y_p$, and $Z_p$). The image of this point on the virtual-camera image plane 310 has the coordinates ($x_i$, $y_i$). The virtual lens of the virtual camera is centered at the point 312, which has the camera coordinates (0, 0, 1) and the world coordinates (0, 0, 1). When the point 308 is in focus, the distance l between the origin 314 and point 312 is the focal length of the virtual camera. Note that, in FIG. 3A, the z axis is used as the axis of symmetry for the virtual camera rather than the y axis, as in FIG. 2A. A small rectangle is shown, on the image plane, with the corners along one diagonal coincident with the origin 314 and the point 310 with coordinates ($x_i$, $y_i$). The rectangle has horizontal sides, including horizontal side 316, of length $x_i$, and vertical sides, including vertical side 318, with lengths $y_i$. A corresponding rectangle with horizontal sides of length $-X_p$, including horizontal side 320, and vertical sides of length $-Y_p$, including vertical side 322. The point 308 with world coordinates $X_p, Y_p,$ and $Z_p$) and the point 324 with world coordinates (0, 0, $Z_p$) are located at the corners of one diagonal of the corresponding rectangle. Note that the positions of the two rectangles are inverted through point 312. The length of the line segment 328 between point 312 and point 324 is $Z_p-1$. The angles at which each of the lines passing through point 312 intersects the z, Z axis 326 are equal on both sides of point 312. For example, angle 330 and angle 332 are identical. As a result, the principal of the correspondence between the lengths of similar sides of similar triangles can be used to derive expressions for the image-plane coordinates $(x_i, y_i)$ for an imaged point in three-dimensional space with world coordinates $(X_p, Y_p,$ and $Z_p)$ 334:

$$\frac{x_i}{l} = \frac{-X_p}{Z_p - l} = \frac{X_p}{l - Z_p}$$

$$\frac{y_i}{l} = \frac{-Y_p}{Z_p - l} = \frac{Y_p}{l - Z_p}$$

$$x_i = \frac{lX_p}{l - Z_p}, y_i = \frac{lY_p}{l - Z_p}$$

Figure 3B:
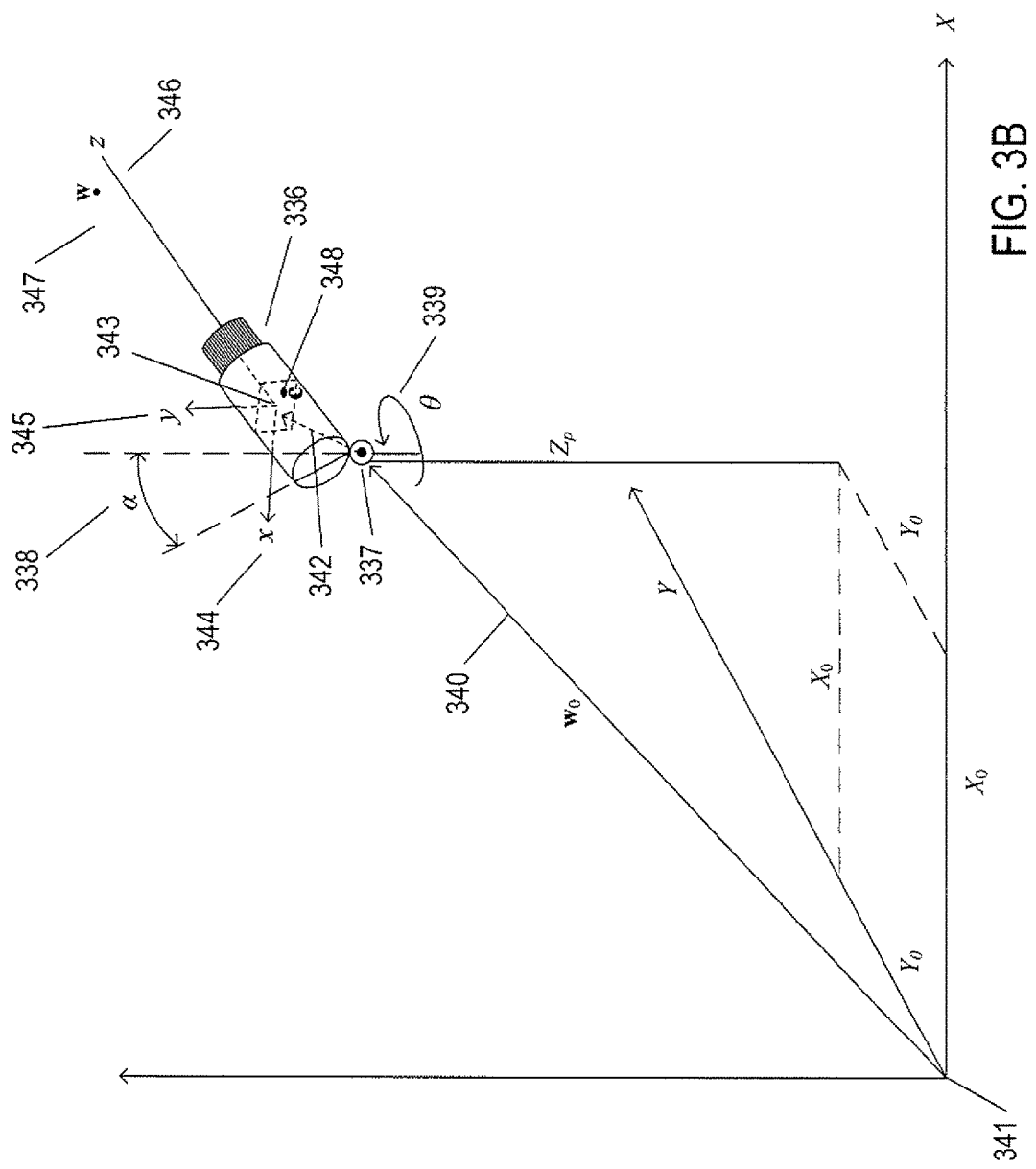

Of course, virtual-camera coordinate systems are not, in general, aligned with the world coordinate system, as discussed above with reference to FIG. 2A. Therefore, a slightly more complex analysis is required to develop the functions, or processes, that map points in three-dimensional space to points on the image plane of a virtual camera. FIGS. 3B-D illustrate the process for computing the image of points in a three-dimensional space on the image plane of an arbitrarily oriented and positioned virtual camera. FIG. 3B shows the arbitrarily positioned and oriented virtual camera. The virtual camera 336 is mounted to a mount 337 that allows the virtual camera to be tilted by an angle α 338 with respect to the vertical Z axis and to be rotated by an angle θ 339 about a vertical axis. The mount 337 can be positioned anywhere in three-dimensional space, with the position represented by a position vector $w_0$ 340 from the origin of the world coordinate system 341 to the mount 337. A second vector r 342 represents the relative position of the center of the image plane 343 within the virtual camera 336 with respect to the mount 337. The orientation and position of the origin of the camera coordinate system coincides with the center of the image plane 343 within the virtual camera 336. The image plane 343 lies within the x, y plane of the camera coordinate axes 344-346. The camera is shown, in FIG. 3B, imaging a point w 347, with the image of the point w appearing as image point c 348 on the image plane 343 within the virtual camera. The vector $w_0$ that defines the position of the camera mount 337 is shown, in FIG. 3B, to be the vector $$w_0 = \begin{bmatrix} X_0 \\ Y_0 \\ Z_0 \end{bmatrix}$$

FIGS. 3C-D show the process by which the coordinates of a point in three-dimensional space, such as the point corresponding to vector w in world-coordinate-system coordinates, is mapped to the image plane of an arbitrarily positioned and oriented virtual camera. First, a transformation between world coordinates and homogeneous coordinates h and the inverse transformation $h^{-1}$ is shown in FIG. 3C by the expressions 350 and 351. The forward transformation from world coordinates 352 to homogeneous coordinates 353 involves multiplying each of the coordinate components by an arbitrary constant k and adding a fourth coordinate component k. The vector w corresponding to the point 347 in three-dimensional space imaged by the virtual camera is expressed as a column vector, as shown in expression 354 in FIG. 3C. The corresponding column vector $w_h$ in homogeneous coordinates is shown in expression 355. The matrix P is the perspective transformation matrix is used to carry out the world-to-camera coordinate transformations (334 in FIG. 3A) discussed above with reference to FIG. 3A. The homogeneous-coordinate-form of the vector c corresponding to the image 348 of point 347, $c_h$, is computed by the left-hand multiplication of $w_h$ by the perspective transformation matrix, as shown in expression 357 in FIG. 3C. Thus, the expression for $c_h$ in homogeneous camera coordinates 358 corresponds to the homogeneous expression for $c_h$ in world coordinates 359. The inverse homogeneous-coordinate transformation 360 is used to transform the latter into a vector expression in world coordinates 361 for the vector c 362. Comparing the camera-coordinate expression 363 for vector c with the world-coordinate expression for the same vector 361 reveals that the camera coordinates are related to the world coordinates by the transformations (334 in FIG. 3A) discussed above with reference to FIG. 3A. The inverse of the perspective transformation matrix, $P^{-1}$, is shown in expression 364 in FIG. 3C. The inverse perspective transformation matrix can be used to compute the world-coordinate point in three-dimensional space corresponding to an image point expressed in camera coordinates, as indicated by expression 366 in FIG. 3C. Note that, in general, the Z coordinate for the three-dimensional point imaged by the virtual camera is not recovered by the perspective transformation. This is because all of the points in front of the virtual camera along the line from the image point to the imaged point are mapped to the image point. Additional information is needed to determine the Z coordinate for three-dimensional points imaged by the virtual camera, such as depth information obtained from a set of stereo images or depth information obtained by a separate depth sensor.

Three additional matrices are shown in FIG. 3D that represent the position and orientation of the virtual camera in the world coordinate system. The translation matrix $T_{w_u}$ 370 represents the translation of the camera mount (337 in FIG. 3B) from its position in three-dimensional space to the origin (341 in FIG. 3B) of the world coordinate system. The matrix R represents the α and θ rotations needed to align the camera coordinate system with the world coordinate system 372. The translation matrix C 374 represents translation of the image plane of the virtual camera from the camera mount (337 in FIG. 3B) to the image plane's position within the virtual camera represented by vector r (342 in FIG. 3B). The full expression for transforming the vector for a point in three-dimensional space $w_h$ into a vector that represents the position of the image point on the virtual-camera image plane $c_h$ is provided as expression 376 in FIG. 3D. The vector $w_h$ is multiplied, from the left, first by the translation matrix 370 to produce a first intermediate result, the first intermediate result is multiplied, from the left, by the matrix R to produce a second intermediate result, the second intermediate result is multiplied, from the left, by the matrix C to produce a third intermediate result, and the third intermediate result is multiplied, from the left, by the perspective transformation matrix P to produce the vector $c_h$. Expression 378 shows the inverse transformation. Thus, in general, there is a forward transformation from world-coordinate points to image points 380 and, when sufficient information is available, an inverse transformation 381. It is the forward transformation 380 that is used to generate two-dimensional images from a three-dimensional model or object corresponding to arbitrarily oriented and positioned virtual cameras. Each point on the surface of the three-dimensional object or model is transformed by forward transformation 380 to points on the image plane of the virtual camera.

Figure 4:
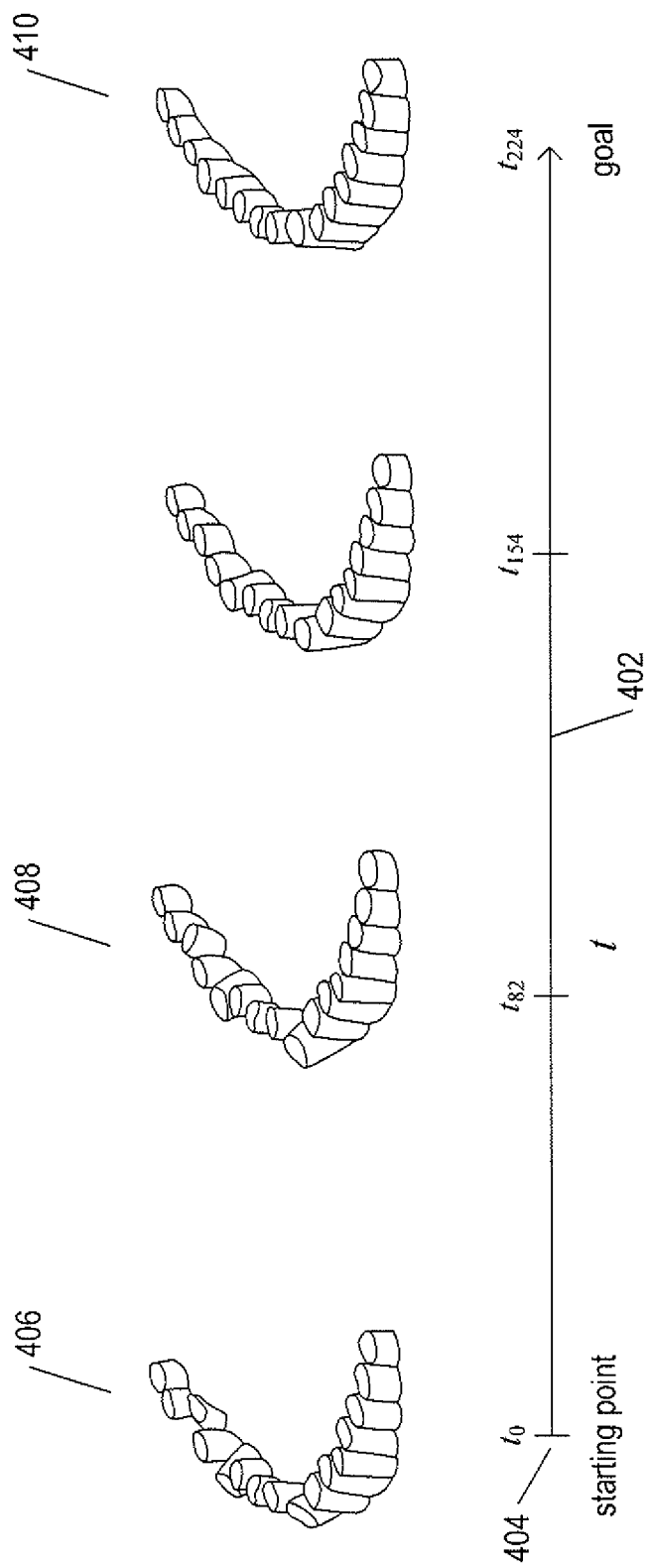
FIG. 4 illustrates a continuum of three-dimensional models of a dental patient's teeth that can be electronically prepared to reflect the expected arrangements of the dental patient's teeth during the course of a proposed treatment plan.

FIG. 4 illustrates a continuum of three-dimensional models of a dental patient's teeth that can be electronically prepared to reflect the expected arrangements of the dental patient's teeth during the course of a proposed treatment plan. In FIG. 4, lower horizontal arrow 402 represents the timeline of the treatment plan. At an initial starting point 404, specified in FIG. 4 as time $t_0$, the arrangement of the dental patient's teeth is captured in an initial three-dimensional model 406 of the patient's teeth. A time-projected three-dimensional model, such as three-dimensional model 408, can be electronically prepared as an estimate of how the dental patient's teeth are expected to be arranged at a future point in time $t_{82}$ or $t_{154}$ during the course of the treatment or procedure. As shown in FIG. 4, the final time-projected three-dimensional model 410 in the continuous series of three-dimensional models represents the goal for the treatment or procedure that is expected to be obtained at time $t_{224}$. Although only four three-dimensional models are shown in both the treatment or procedure timeline 402 in FIG. 4, a time-projected three-dimensional model for any point along the timeline can be electronically prepared using extrapolation and simulation-based methodologies.

Figure 5A:
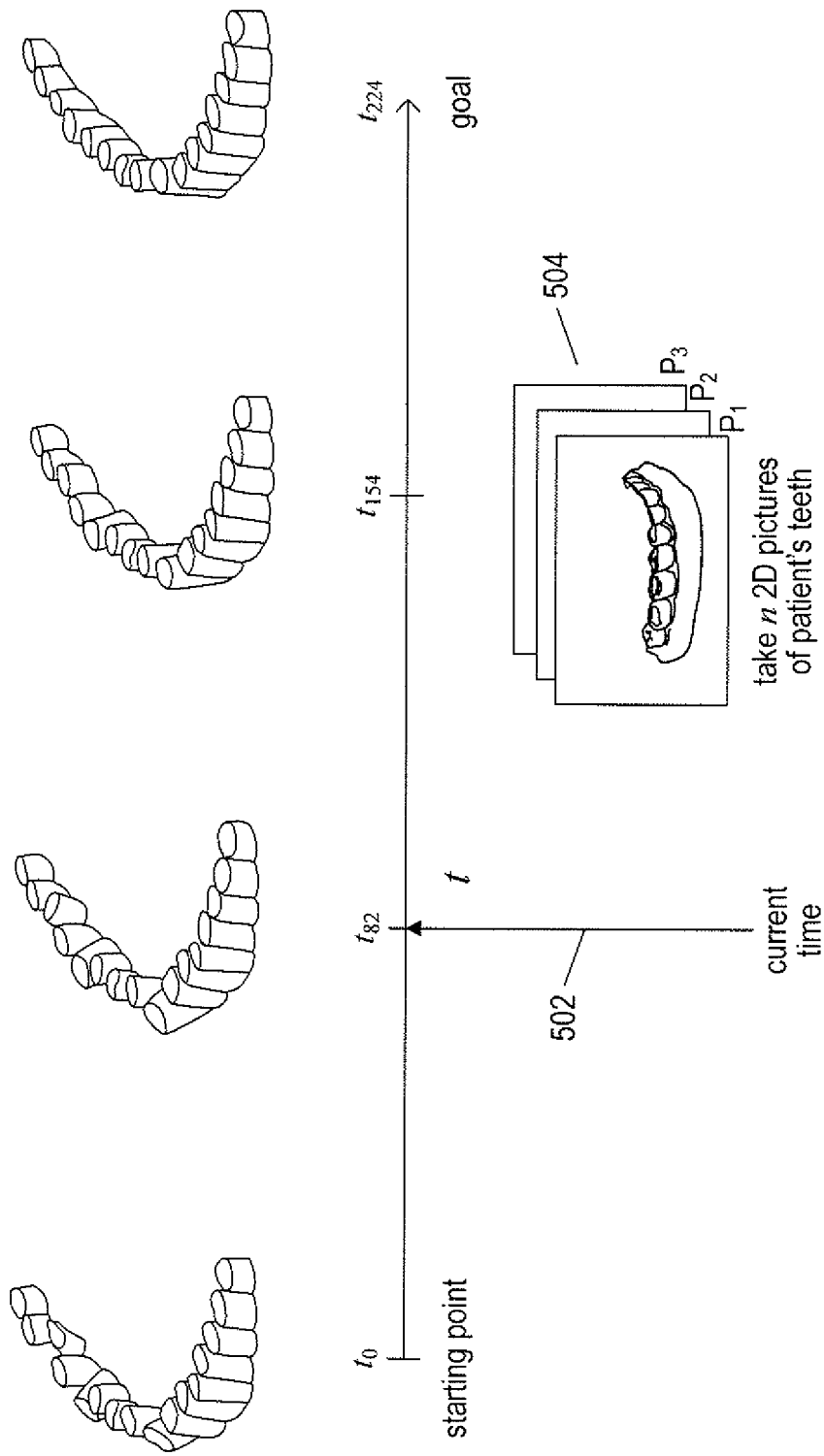

FIGS. 5A-D graphically illustrate the treatment-monitoring method to which the current document is, in part, directed. As shown in FIG. 5A, at a particular current point in time, $t_{82}$, during a dental patient's treatment or procedure, represented in FIG. 5A by vertical arrow 502, a dental practitioner examines the patient and takes a number n of two-dimensional pictures of the patient's teeth 504 ($P_1$, $P_2$, $P_3$). Alternatively, in certain implementations, the two-dimensional pictures may be taken by a patient's friend or relative, or even the patient, using a camera timer or smartphone features that facilitate acquisition of images of a user. In the current example, n is equal to 3. In general, each photograph or subset of the photographs represents a certain, standard view or image type. A dental practitioner or other person is provided with instructions for capturing an image of a particular standard view or type. As shown in FIG. 5B, once the practitioner has submitted these two-dimensional images, along with patient information, an indication of the time that the two-dimensional images were captured, and other such information, the treatment-monitoring system, to which the current document is, in part, directed, determines camera parameters for virtual cameras 506-508, the orientations and positions of which most likely correspond to the camera parameters of the dental practitioner's camera at the points in time at which each of the corresponding n two-dimensional pictures, 510-512, respectively, were captured by the dental practitioner or other person.

Figure 5C:
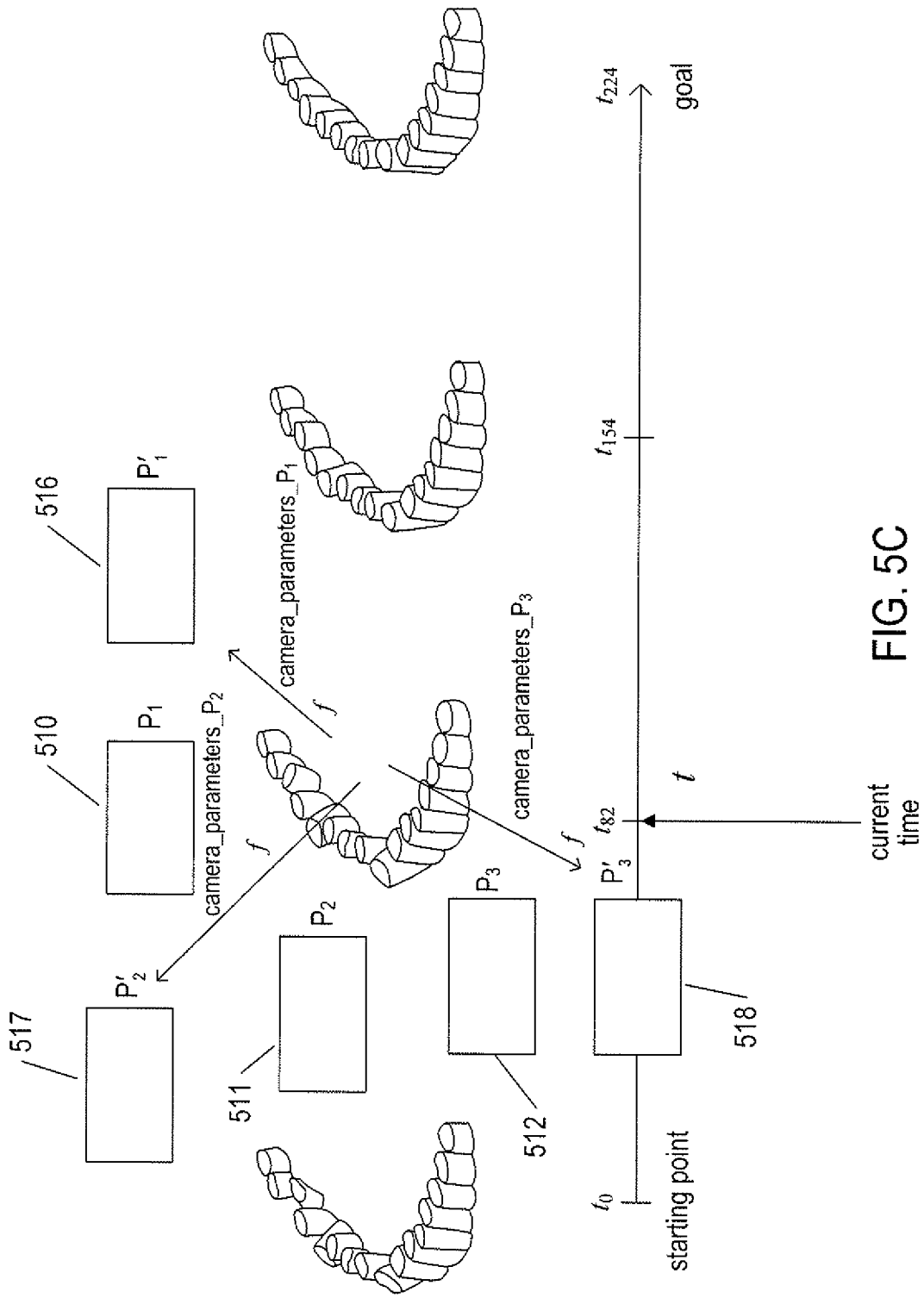
Figure 5D:
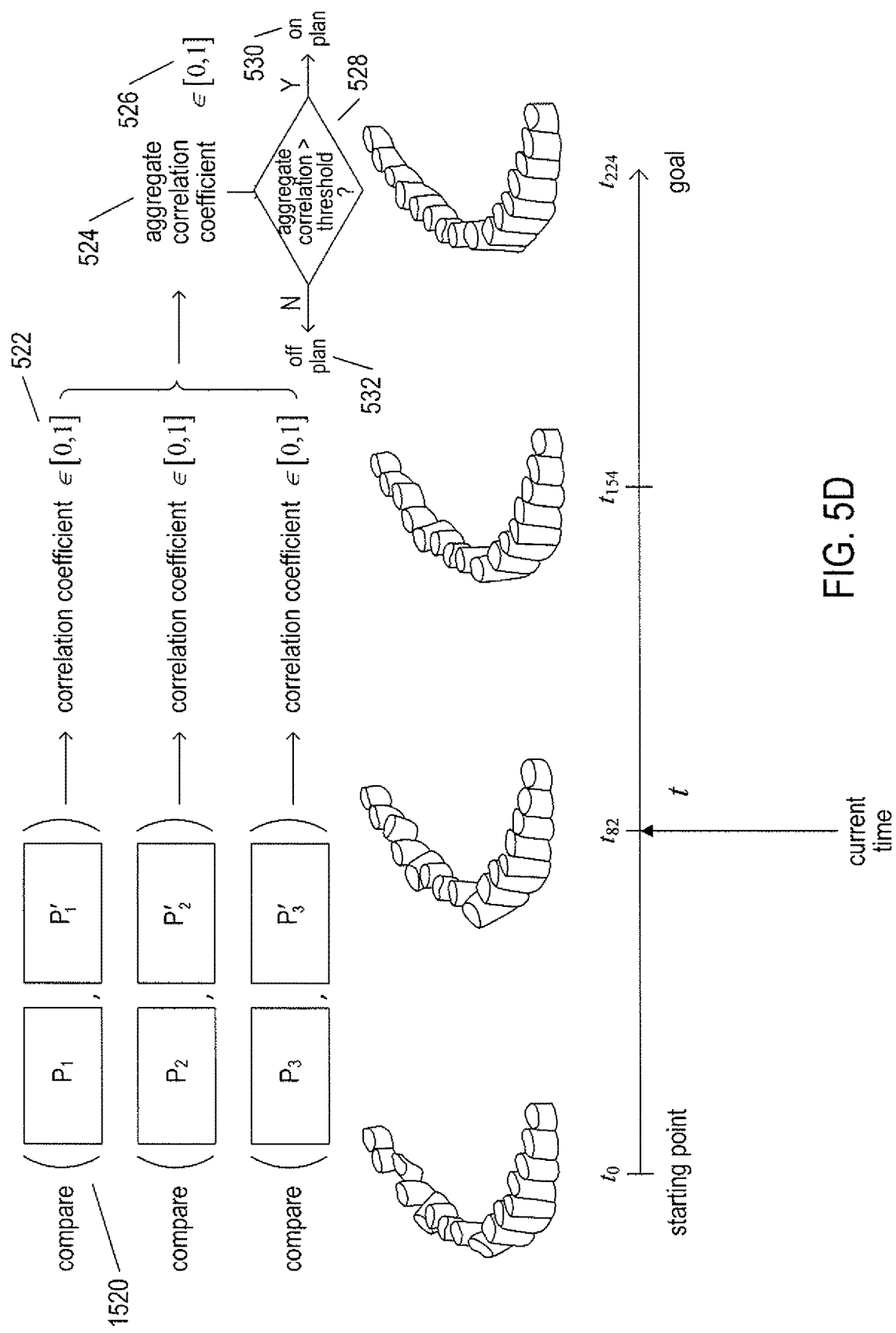

Next, as shown in FIG. 5C, the determined camera parameters for the virtual cameras are used to generate corresponding two-dimensional images 516-518 corresponding to the n two-dimensional images 510-512 taken by the dental practitioner or other person. Finally, as shown in FIG. 5D, a comparison operation, such as comparison operation 1520, is applied to each pair of a dental-practitioner-submitted image and a corresponding image generated from the three-dimensional model in order to produce a correlation coefficient. In one implementation, the correlation coefficients are expressed as floating point values between 0 and 1 (522 in FIG. 5D). The correlation coefficients for the individual images are used to generate a single aggregate correlation value 524, in one implementation of the currently described method and system, which is also a floating-point value between 0 and 1 (526 in FIG. 5D). When the aggregate correlation value computed from the submitted two-dimensional images and the projected three-dimensional model is greater than a threshold value, as determined in step 528, then the treatment-monitoring system stores, in memory, and returns an indication that the treatment is proceeding according to plan 530. Otherwise, the treatment-monitoring system stores, in memory, and returns an indication that the treatment is not going according to plan 532. It should be noted that, in certain implementations, multiple images for a given standard view may be used for generating correlation coefficients and an aggregate correlation coefficient. In other implementations, including an implementation discussed below, a best representative image for each standard view is selected for processing.

Figure 6:
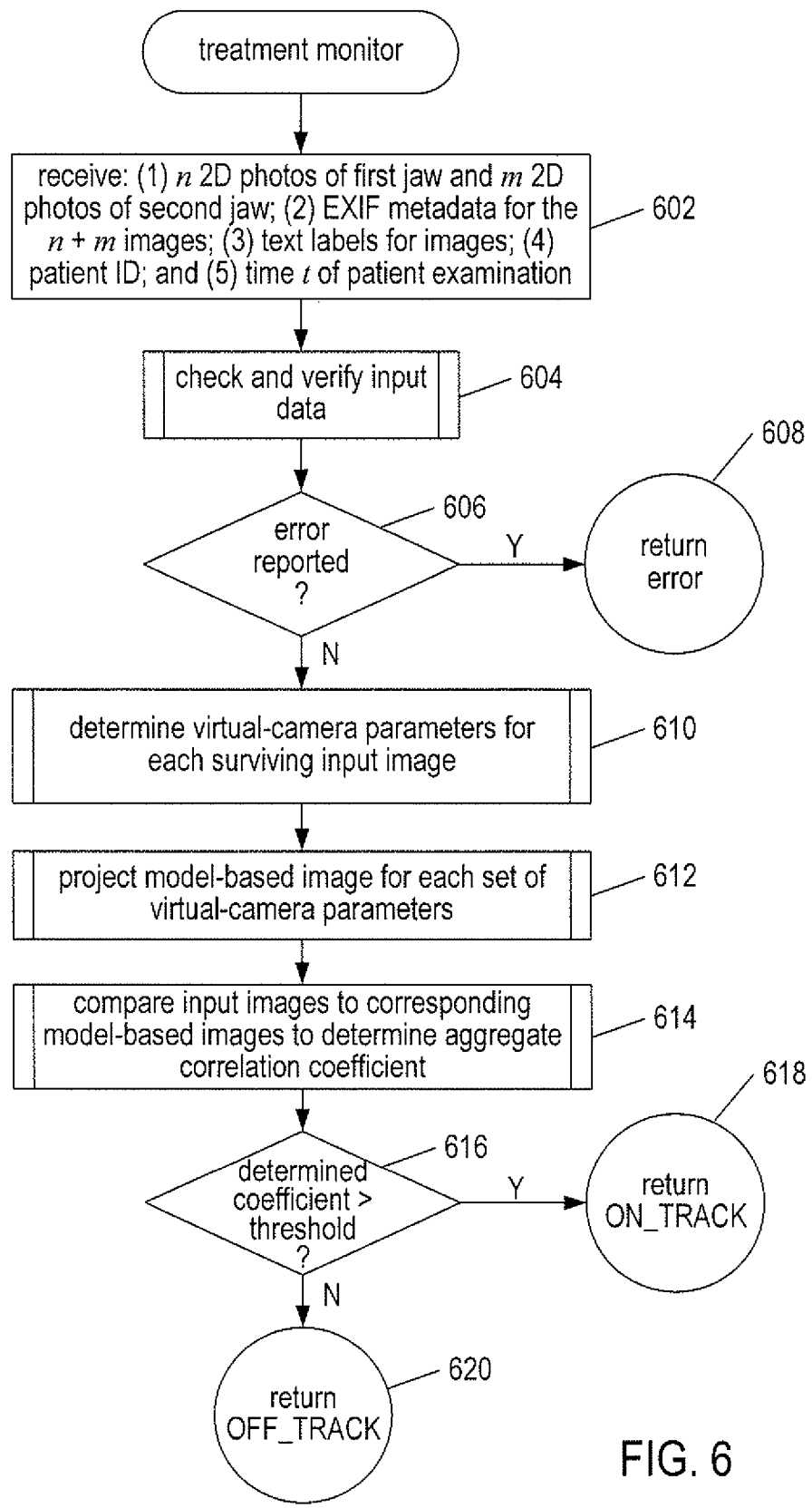
FIG. 6 provides a control-flow-diagram illustration of the operation of the treatment-monitoring system and treatment-monitoring method to which the current document is directed.

FIG. 6 provides a control-flow-diagram illustration of the operation of the treatment-monitoring system and treatment-monitoring method to which the current document is directed. Additional control-flow diagrams, discussed below, provide greater detail for various steps in the highest-level control-flow diagram shown in FIG. 6. In step 602, the treatment-monitoring method and/or system ("treatment monitor") receives: (1) n two-dimensional photographs of a first jaw and m two-dimensional photographs of a second jaw of a dental patient examined during the course of a treatment or procedure; (2) exchangeable-image-file-format ("EXIF") metadata for each of the n+m two-dimensional images; (3) text labels for the two-dimensional images, which include, among other things, an indication of a standard type of view represented by each image and characterizations and parameters for the digitally encoded image, including the size of the image, date and time information, and camera settings, including one or more of the camera model and make and camera orientation, aperture, shutter speed, focal length, metering mode, and International Organization for Standardization ("ISO") speed information; (4) a patient ID and other information; and (5) the time and date, t, of the patient examination which produced the two-dimensional photos. In step 604, the treatment monitor checks and verifies the input data. When there are any errors detected, as determined in step 606, an error is returned, in step 608, to allow various types of amelioration procedures to be undertaken, including requesting additional or substitute input information. Otherwise, in step 610, the treatment monitor determines the virtual-camera parameters for each of the input images that have survived the initial check and verification step 604. In step 612, a two-dimensional image corresponding to each of the input images is generated from the time-projected three-dimensional model using the determined set of virtual-camera parameters for the corresponding input image. In step 614, each input image and corresponding model-based projected image is compared to determine a correlation coefficient, and the set of correlation coefficients are used to determine an aggregate correlation coefficient. When the determined aggregate correlation coefficient is greater than a threshold value, as determined in step 616, an indication that the treatment or procedure is on track, ON_TRACK, is returned in step 618. Otherwise, an indication that the treatment or procedure is off track, OFF_TRACK, is returned in step 620.

Figure 7A:
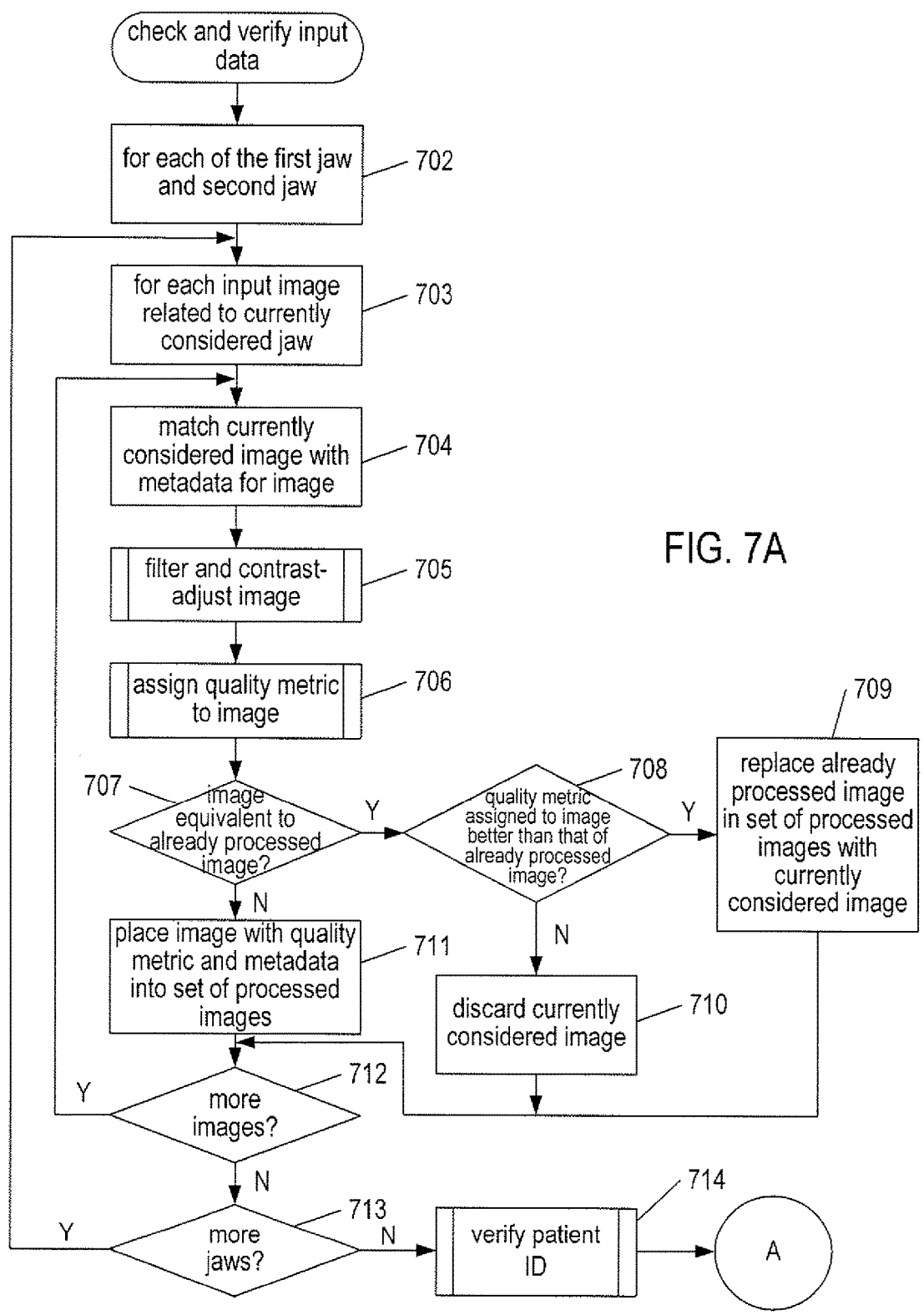
FIGS. 7A-B illustrate, using control-flow diagrams, step 604 of FIG. 6.
Figure 7B:
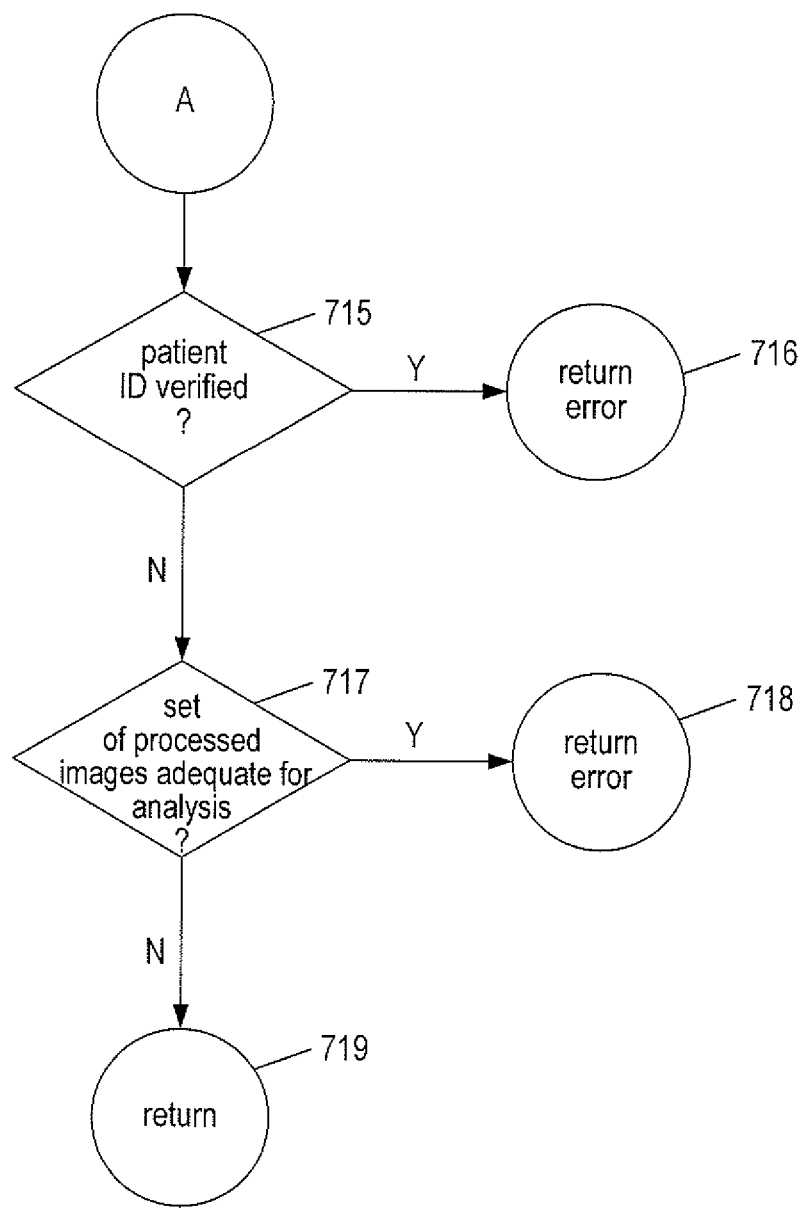

FIGS. 7A-B illustrate, using control-flow diagrams, step 604 of FIG. 6. In the nested for-loops of steps 702-713, each input image related to each of the first and second jaws of the dental patient is considered (for each input image related to currently considered jaw 703). In step 704, the check-and-verification method matches the currently considered image within the nested for-loops with the metadata extracted and collected for that image from the input data. In step 705, the check-and-verify method filters the image to remove inconsistencies and defects and, in certain cases, may expand or contract the contrast within the image, or alter the color balance, in order to adjust the image for further analysis. In step 706, the check-and-verify method carries out a qualitative analysis of the image and assigns a quality metric to the image. This quality metric reflects how well the image corresponds to the image type specified in the metadata, as well as the sharpness, clarity, and completeness of the image. When the currently considered image is equivalent to an image already processed within the nested for-loops, as determined in step 707, and when the quality of metric assigned to the currently considered image is better than that of the already-processed image, as determined in step 708, the already-processed image is replaced by the currently considered image in a set of processed images prepared by the check-and-verify method, in step 709. Otherwise, when the quality metric assigned to the currently considered image is not better than that of the already-processed image, as determined in step 708, the currently considered image is discarded, in step 710. When the currently considered image is not equivalent to an already-processed image, as determined in step 707, the currently considered image is placed, along with the computed quality metric and various metadata, into the set of processed images, in step 711 and steps 704-711 repeated if there are more images 712 or more jaws 713. In step 714, the check-and-verify method verifies the patient ID included in the input information. Turning to FIG. 7B, when the patient ID is verified, as determined in step 715, and when the set of processed images prepared in the nested for-loops of step 702-713 are deemed adequate for further analysis, as determined in step 717, the check-and-verify method returns, in step 719, without reporting an error condition. In this case, the set of processed images contains a single, best image of each type, and the set of images contains sufficient information to proceed with analyzing progress of the treatment. Otherwise, error conditions are reported in steps 716 and 718. Of course, the check-and-verify method may, in various implementations, carry out additional types of verification and checking of the input data, and may return addition types of error conditions when the additional checks and verifications fail.

Figure 8:
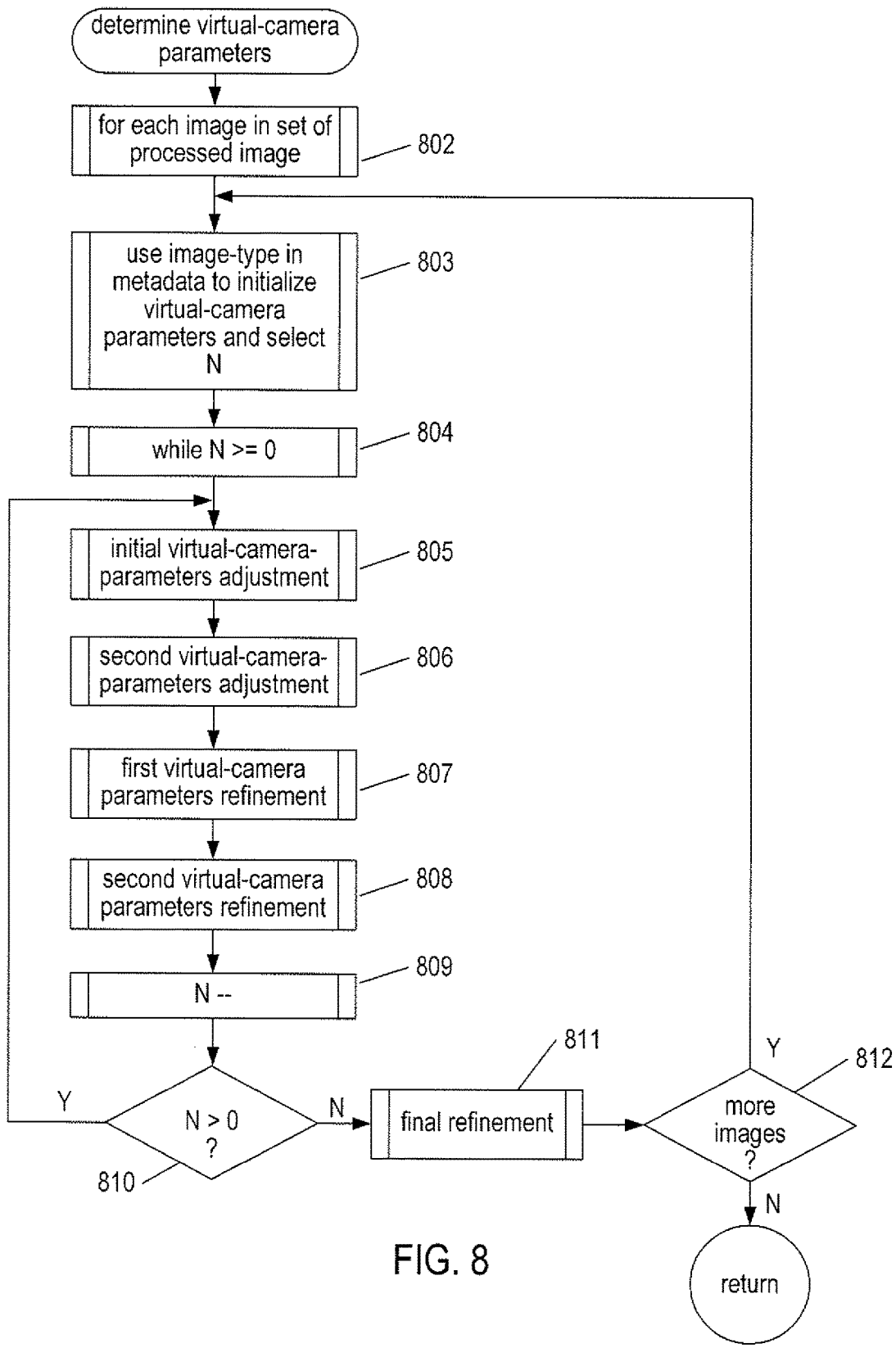
FIG. 8 provides a control-flow diagram for step 610 of FIG. 6, a virtual-camera-parameters determination method.

FIG. 8 provides a control-flow diagram for step 610 of FIG. 6, a virtual-camera-parameters determination method. In the for-loop of steps 802-812, each image in the set of processed images produced by the check-and-verify method, discussed above with reference to FIGS. 7A-B, is considered. In step 803, the method uses the metadata associated with the image, including the image type, to initialize a set of virtual-camera parameters associated with the image and to select an iteration count N. Different types of images and images with different characteristics and qualities may require a different number of adjustments and refinements. Then, in the while-loop of steps 804-810, the initial virtual-camera parameters for the image are adjusted and refined, with the while-loop iterating for N iterations. The adjustment and refinement process is non-convex, as a result of which the process does not necessarily converge. In step 805, a first virtual-camera-parameters adjustment method is invoked to make relatively coarse adjustments to the initial virtual-camera parameters. In step 806, a second virtual-camera-parameters adjustment method is invoked to more finely adjust the virtual-camera parameters for the image. In step 807, a first virtual-camera-parameters refinement method is invoked to refine the virtual-camera parameters associated with the image and, in step 808, a second virtual-camera-parameters refinement procedure is invoked to refine the virtual-camera-parameters associated with the image. In step 809, the iteration variable N is decremented. When N is greater than 0, as determined in step 810, then the while-loop of steps 804-810 continues to iterate. Otherwise, in step 811, a final refinement method is called to adjust the virtual-camera parameters for the image. Note that, through the various steps and iterations, the virtual-camera parameters associated with an image are generally continuously adjusted and refined towards a set of virtual-camera parameters that best estimates the position, orientation, and focal length of the dental practitioner's camera, with respect to the patients teeth, used to initially capture the input image.

Figure 9:
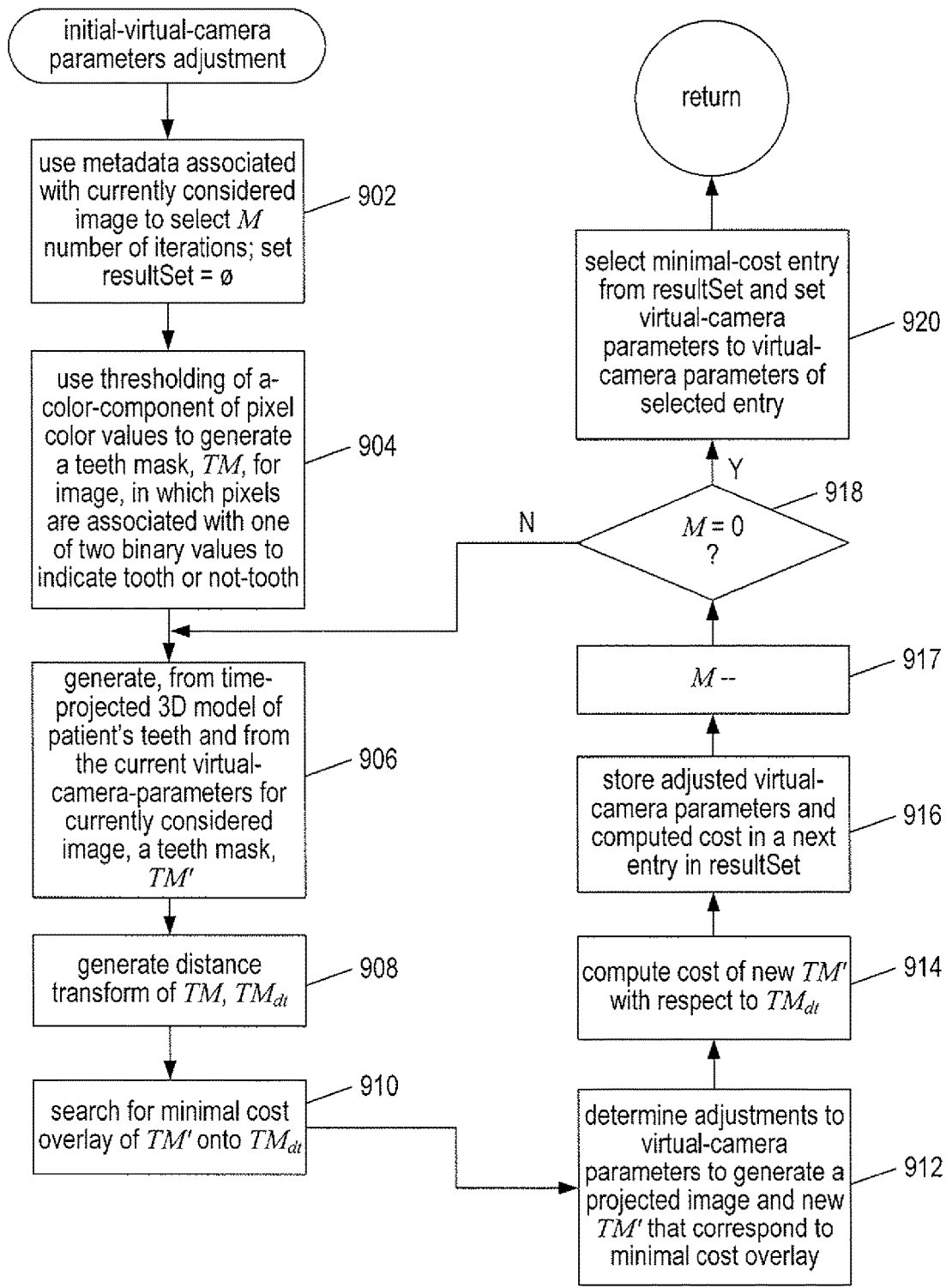
FIG. 9 provides a control-flow diagram for the initial virtual-camera-parameters adjustment method invoked in step 805 of FIG. 8.

FIG. 9 provides a control-flow diagram for the initial virtual-camera-parameters-adjustment method invoked in step 805 of FIG. 8. In step 902, the method uses metadata associated with the image to select a value of an iteration variable M, in similar fashion to the selection of a value for the iteration variable N in step 803 in FIG. 8, and a set of entries resultSet is initialized to be empty. In step 904, the initial virtual-camera-parameters-adjustment method applies thresholding to each pixel color/intensity value within the image to generate a teeth mask, TM, for the image. When the pixels are encoded in the Lab color model, the a color component of the pixel color/intensity value is thresholded. The Lab color model is a color-opponent space with dimension L for lightness and color-opponent dimensions a and b, based on nonlinearly compressed color space coordinates, such as International Commission on Illumination ("CIE") XYZ color space coordinates. When other color-model encodings are used for pixel colors and intensities, other components or values derived from one or more components of the pixel color/intensity values are thresholded. The elements corresponding to image pixels in the teeth mask TM are associated with one of two binary values to indicate whether the pixel or element corresponds to a tooth region or a non-tooth region within the image. In step 906, a similar teeth mask, TM', is generated from the time-projected three-dimensional using the current virtual-camera parameters for the two-dimensional input image from which teeth mask TM was produced. In step 908, a distance transform of teeth mask TM, $TM_{dt}$, is generated. In step 910, the method searches for a minimal-cost overlay of teeth mask TM' onto the distance transform of TM, $TM_{dt}$, with the search carried out over various rotations and scale factors of the teeth mask TM' with respect to the distance transform $TM_{dt}$. In step 912, adjustments to the virtual-camera parameters for the currently considered two-dimensional image are computed in order to generate a new two-dimensional image from the three-dimensional model and a new teeth mask TM' that correspond to the minimal-cost overlay of the previously computed TM' onto $TM_{dt}$. In step 914, a cost of the new TM' teeth mask with respect to $TM_{dt}$ is computed. The adjusted virtual-camera parameters and computed cost, obtained in steps 912 and 914, are stored as a next entry in the set variable resultSet, in step 916. In step 917, iteration variable M is decremented. When M is still greater than 0, as determined in step 918, control returns to step 906 for an additional iteration of the virtual-camera-parameters adjustment. Otherwise, in step 920, the minimal-cost entry in resultSet is selected and the virtual-camera parameters associated with the two-dimensional image are set to the virtual-camera parameters in the selected entry.

Figure 10A:
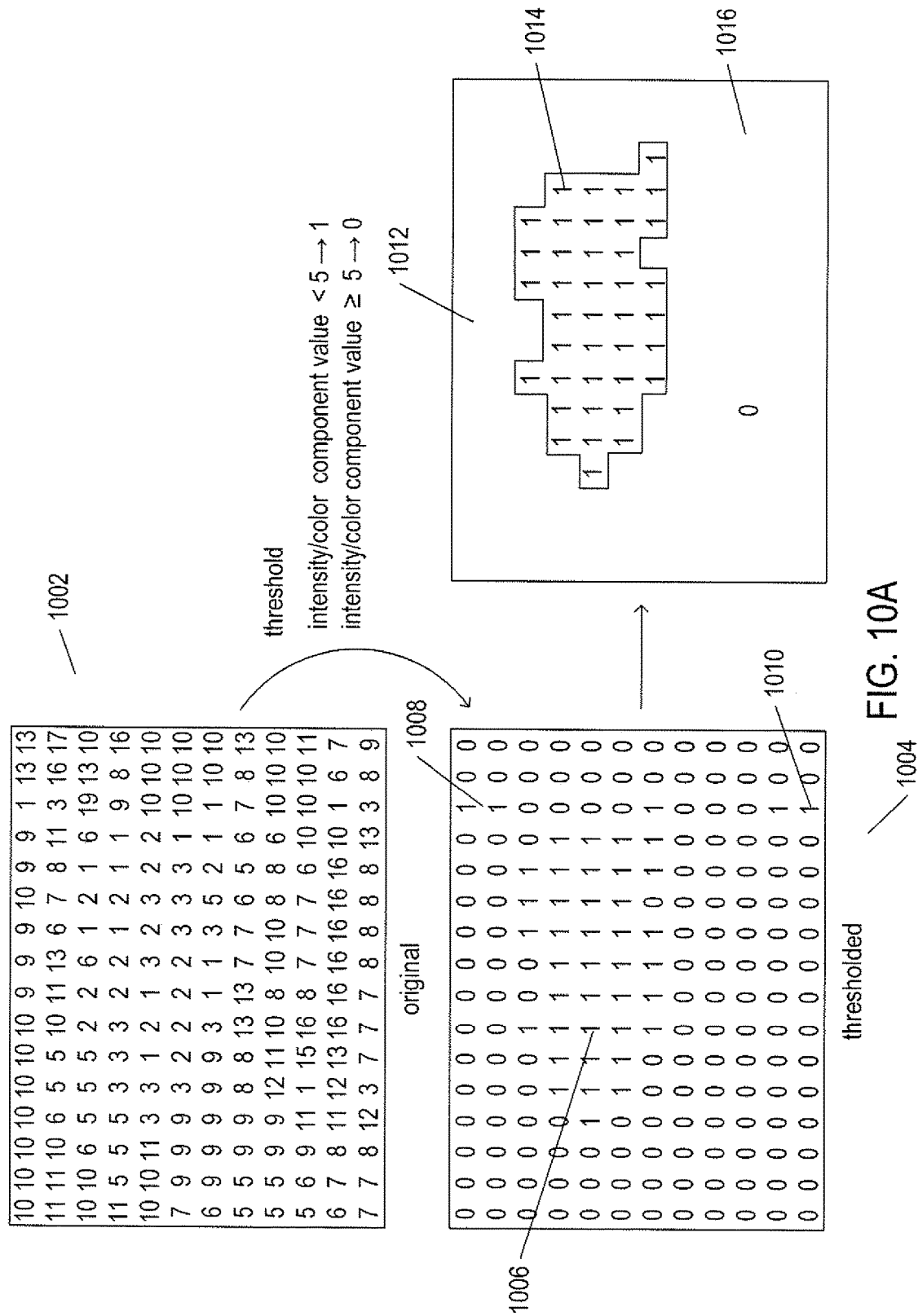
FIGS. 10A-C provide additional details with regard to steps 904, 908, and 912 of FIG. 9.
Figure 10B:
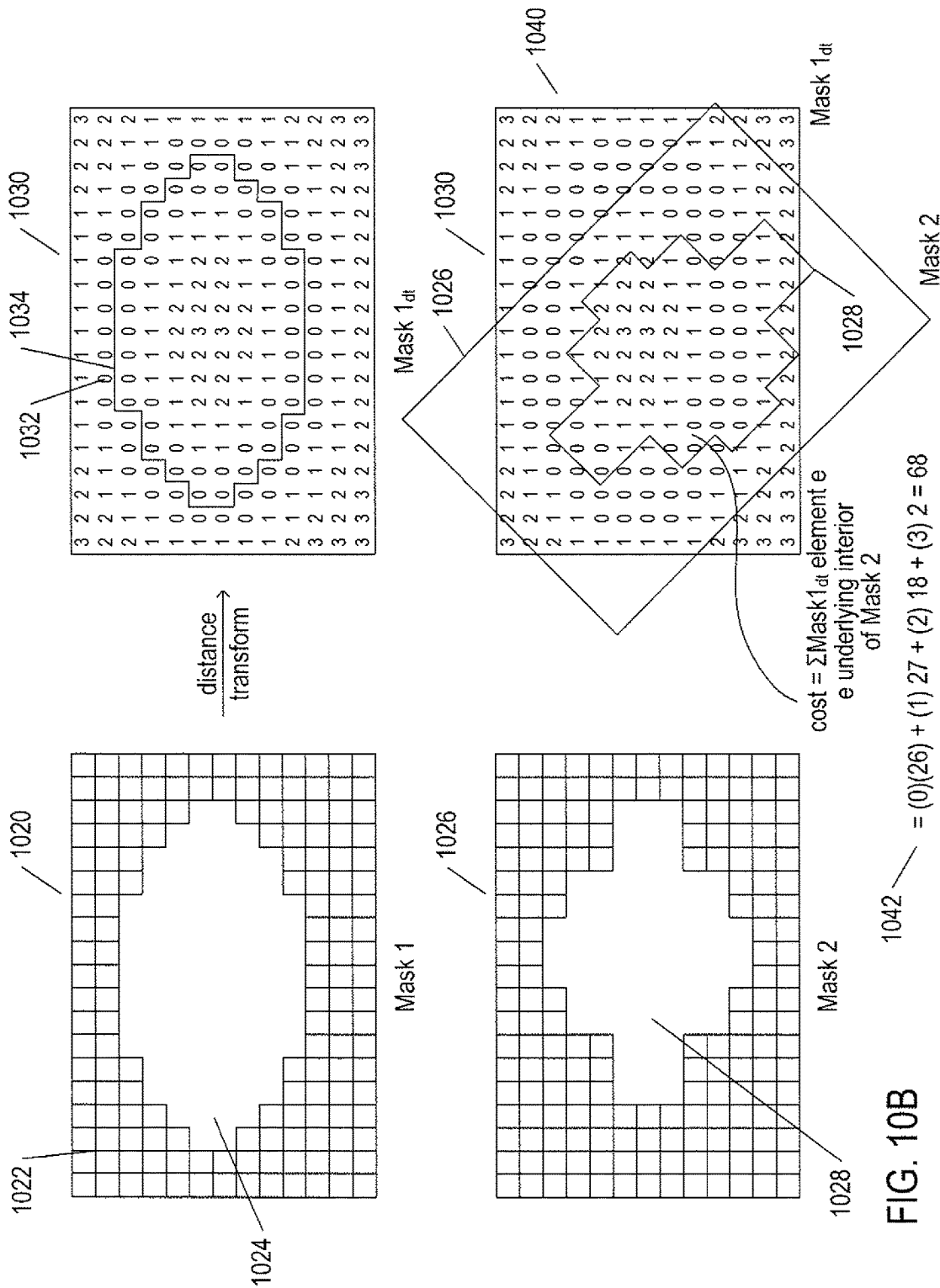
Figure 10C:
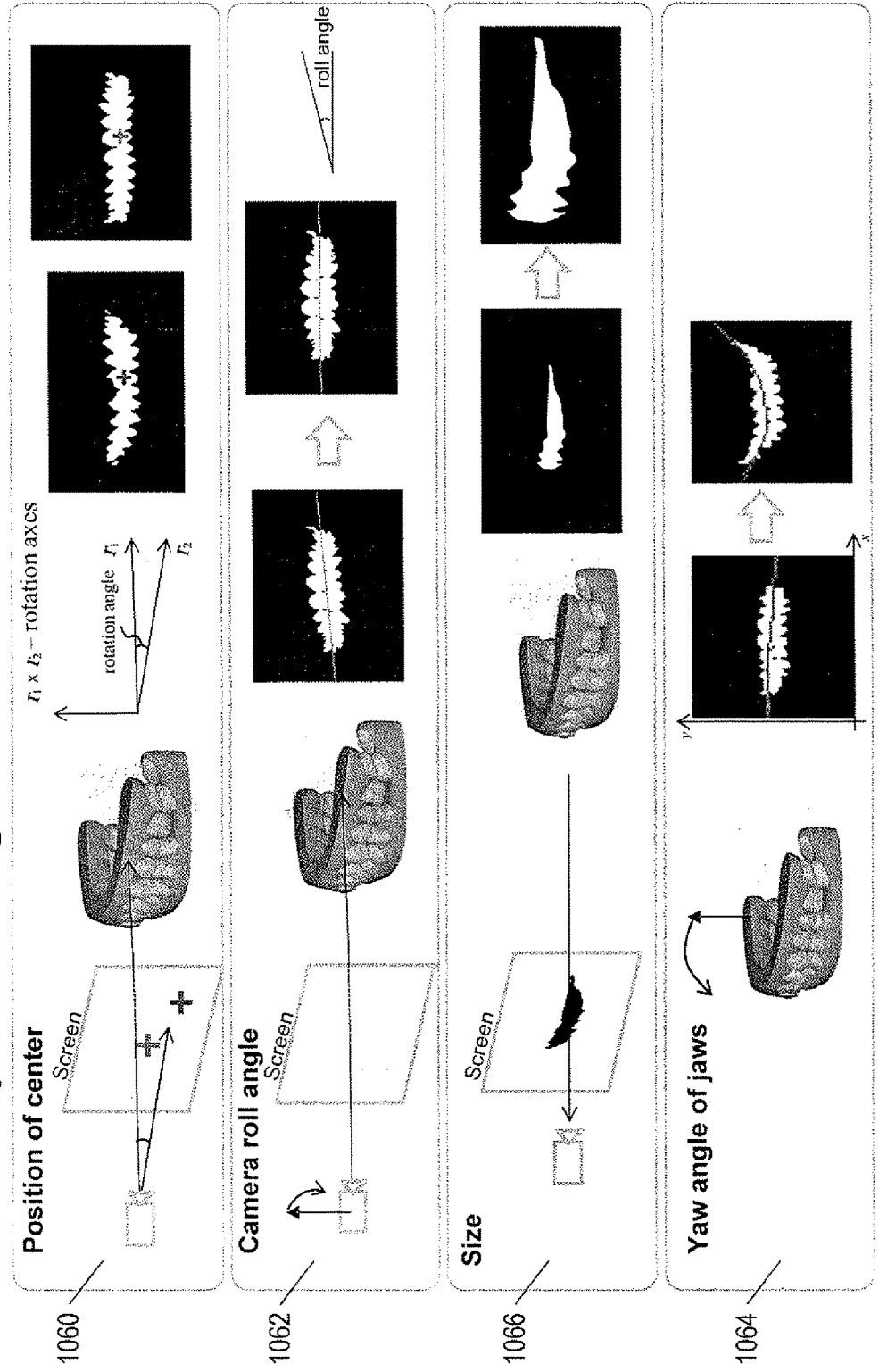

FIGS. 10A-C provide additional details with regard to steps 904, 908, and 912 of FIG. 9. FIG. 10A illustrates the thresholding step 904 in FIG. 9. A small hypothetical portion of an image 1002 is shown as the original image in FIG. 10A. Each pixel in the original image is shown to have an intensity/color-component value. In the thresholding operation, those pixels with intensity/color-component values less than a threshold value, in the current hypothetical case 5, are assigned to the value 1 and all other pixels are assigned to the value 0. In one implementation, the threshold value is determined using well-known Otsu's well-known thresholding method, in which image pixels are partitioned into two classes on the assumption that the intensity-value distribution of the pixels can be modeled as a bi-modal distribution. Otsu's method seeks a threshold that minimizes the intra-class variance, which is the weighted sum of the intensity-value variances of the two classes. Pixels assigned the value 1 are considered to be tooth-region pixels and the other pixels are considered to be non-tooth-region pixels. Thus, in the thresholded image 1004, a small interior region 1006 corresponds to teeth. In addition, there are two small, teeth-like regions 1008 and 1010 adjacent to the edge of the image. In a next step, any of the teeth regions adjacent to the edge are backfilled with 0 values, since the teeth should not be at the borders of the photographs according to the procedures and protocols for taking photographs by the dental practitioner. A final step, not shown in FIG. 10A, reconsiders 0-backfilled regions to ensure that teeth-like regions have not been inadvertently back filled. The result of the next step is a tooth mask 1012 with an interior tooth-corresponding region 1014 with 1-valued pixels and an outer region with 0 value corresponding to non-tooth regions 1016.

FIG. 10B illustrates the computation of a distance transform of one mask in computing the cost of an overlay of a second mask onto this distance transform. A first mask 1020 is shown in FIG. 10B. The outer portion of the mask 1022 is shown in grid lines and has one of two binary values and an interior portion of the mask 1024 is shown without grid lines and each element or pixel in the interior portion has the other of the two binary values. A second mask 1026 is shown below the first mask. Note that the interior region of the second mask 1028 is differently shaped in size than the interior region 1024 of the first mask 1020. A distance transformation transforms the first mask 1020 into a first-mask distance transform 1030. In this transformation, the value of the elements or pixels in the first mask are replaced by the distance, in elements or pixels, that needs to be traversed from the element to the boundary between the outer and inner portions of the first mask. For example, from pixel 1032, no other pixels or elements need to be traversed in order to reach the boundary 1034 of the inner and outer mask regions, and therefore pixel or element 1032 has value 0 in the distance transform. Many different types of distance metrics can be used, including Euclidian distance, city-block distance, and other such distances. In the right-hand corner of FIG. 10B, the second mask 1026 is rotated with respect to the distance transform of the first mask 1030 and overlaid on top of the distance transform of the first mask to produce an overlay 1040. In the search for the minimal cost or best overlay of TM' with respect to $TM_{dt}$, in step 910 of FIG. 9, a state space search is carried out in which various possible rotations and translations of the second mask are considered with respect to the distance transform of the first mask for various different scales, or sizings, of the second mask. The cost for a particular overlay, such as overlay 1040, is computed as the sum of the values of the elements in the distance transform underlying the interior region 1028 of the second mask, as indicated 1042 in FIG. 10B below the overlay 1040.

FIG. 10C illustrates certain of the adjustments of the virtual-camera parameters in order to create a projected image from which a new TM' that corresponds to a minimal-cost overlay of the TM' over the distance transform can be prepared. The adjustments include adjusting the position or center of the virtual camera 1060, adjusting the roll and yaw angles of the virtual camera 1062 and 1064, and adjusting the focal length or distance of the virtual camera from the surface of the 3D model 1066. The adjustments alter one or more of the shape, size, and orientation of the inner teeth region of the previous TM' so that a minimal-cost overlay of the new TM' is obtained. First, the camera is rotated 1060 so that the center of mass of the two masks, TM and TM', coincide. For this purpose, two vectors are constructed in a coordinate system with an origin coincident with the camera position. The two vectors include a first vector that describes the position of the TM center of mass and a second vector that describes the position of the TM' center of mass. The camera is rotated about a rotation axis coincident with the vector obtained as the cross-product of the first and second vectors. The camera roll angle is adjusted 1062, for front or side views only, by fitting straight lines through both teeth masks and rotating camera around the z axis (346 in FIG. 3B) so that the lines are parallel. To modify the area of mask TM' 1066, the camera is moved closer or further from the three-dimensional model. A coefficient K controls this movement. When K>1, the camera is moved away from the three-dimensional model. Otherwise, the camera is moved closer to the three-dimensional model. Coefficient K is found using an empirical formula $$K = 1 + \frac{1}{2}\left(\sqrt[4]{\frac{|TM'|}{|TM|}} - 1\right),$$

where |TM| and |TM'| are the areas, in pixels, of the two masks TM and TM', respectively. Adjustment of the yaw angle 1064 is carried for front or side views, but not for occlusal views. The yaw angle is computed using parameters of parabolas that are fitted through masks and an empirical formula for computing of the yaw angle in radians, provided below:

$$y = a_1 x^2 + b_1 x + c_1, \text{ where } x,y \in TM,$$

$$y = a_2 x^2 + b_2 x + c_2, \text{ where } x,y \in TM',$$

$$\text{yaw angle} = \frac{1}{2}\sqrt{|a_1 - a_2|} * \text{sign}(a_1 - a_2).$$

Figure 11:
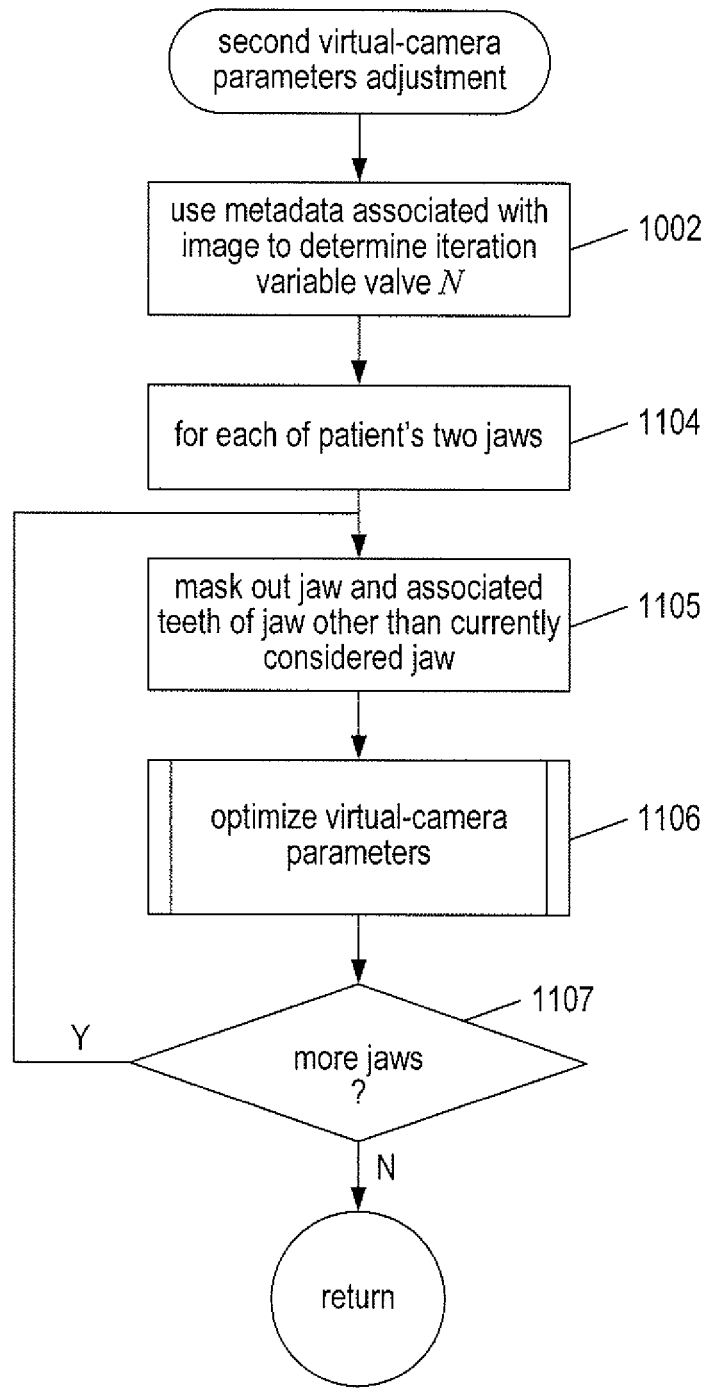
FIG. 11 shows the second virtual-camera-parameter's adjustment method invoked in step 806 of FIG. 8.

FIG. 11 shows the second virtual-camera-parameters adjustment method invoked in step 806 of FIG. 8. In step 1102, the metadata associated with the image is used to determine a value for an iteration variable N. Then, in the for-loop of steps 1104-1107, each of the two jaws of the dental patient, and their associated teeth, are considered. In step 1105, the jaw and associated teeth that are not currently considered are removed from the image and from current consideration. Then, in step 1106, the virtual-camera parameters associated with the image are optimized for that portion of the image corresponding to the currently considered jaw and associated teeth.

Figure 12:
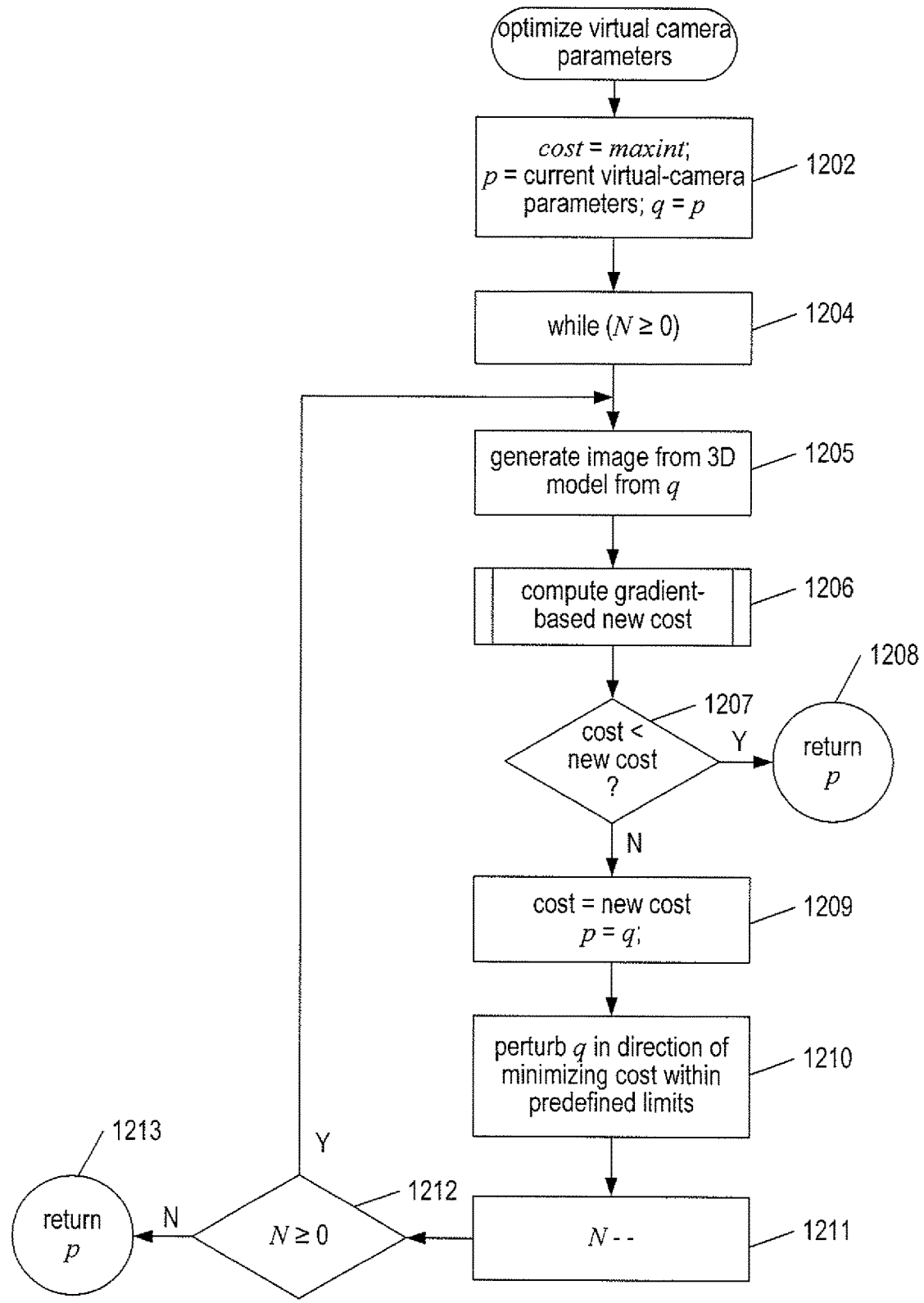
FIG. 12 provides a control-flow diagram for the optimization step 1106 in FIG. 11.

FIG. 12 provides a control-flow diagram for the optimization step 1106 in FIG. 11. In step 1202, an initial value of a variable cost is set to a large number and the variables p and q are both set to the current virtual-camera parameters. Then, in the while-loop of steps 1204-1212, an optimization method is used to find an optimized set of virtual-camera parameters for the currently considered image. The while-loop iterates over a number of iterations indicated by the iteration variable N, determined in step 1102 of FIG. 11. In step 1205, a two-dimensional image is generated from the three-dimensional model using the virtual-camera parameters q. In step 1206, a gradient-based cost is computed for this generated two-dimensional image with respect to the currently considered input image. When the new gradient-based cost is greater than the value stored in the variable cost 1207, the virtual-camera parameters p are returned, in step 1208, since these parameters correspond at least to a local minimum discovered in the previous iteration of the while-loop. Otherwise, the value of the variable cost is set to the new cost computed in step 1206 and the virtual-camera parameters p are set to q, in step 1209. In step 1210, the virtual-camera parameters q are perturbed in the direction of minimizing the cost within certain predefined limits. In step 1211, the iteration variable N is decremented. When the iteration variable N is greater than or equal to 0, as determined in step 1212, control returns to step 1205 for another iteration of the while-loop. Otherwise, the current virtual-camera parameters p are returned, in step 1213. The optimization approach illustrated in FIG. 12 is used subsequently for numerous steps, described below.

In one implementation, a Nelder-Mead downhill simplex optimization method is employed, with seven dimensions, including three rotations, three translations, and the virtual-camera view angle. In this method, a simplex with n+1 vertices in n dimensions, for a problem in n variables, is used, with test points corresponding to the vertices. The test points are replaced in a way that conserves the volume of the simplex but moves and deforms the simplex toward a local optimum. There are many variations of the Nelder-Mead downhill simplex optimization method, and many additional optimization methods that may be employed to optimize the virtual-camera parameters.

Figure 13A:
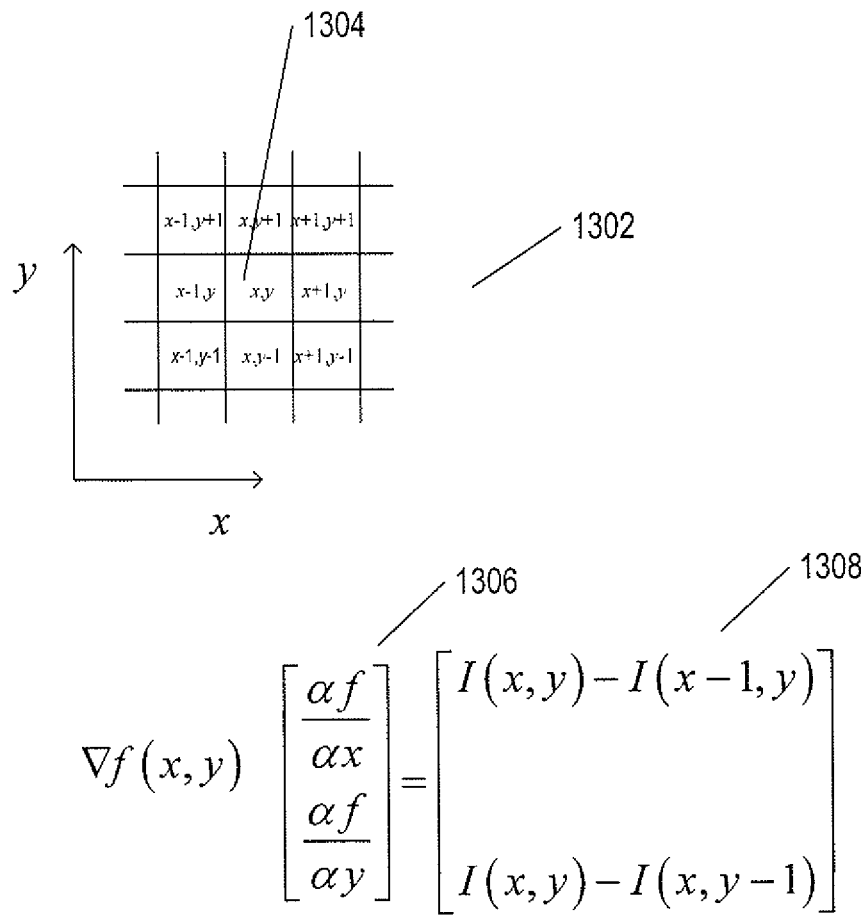
Figure 13A:
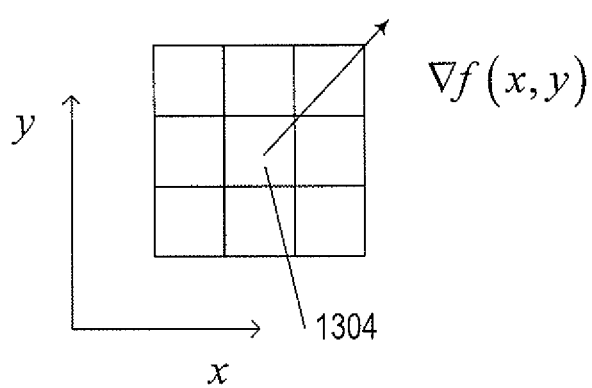
Figure 13B:
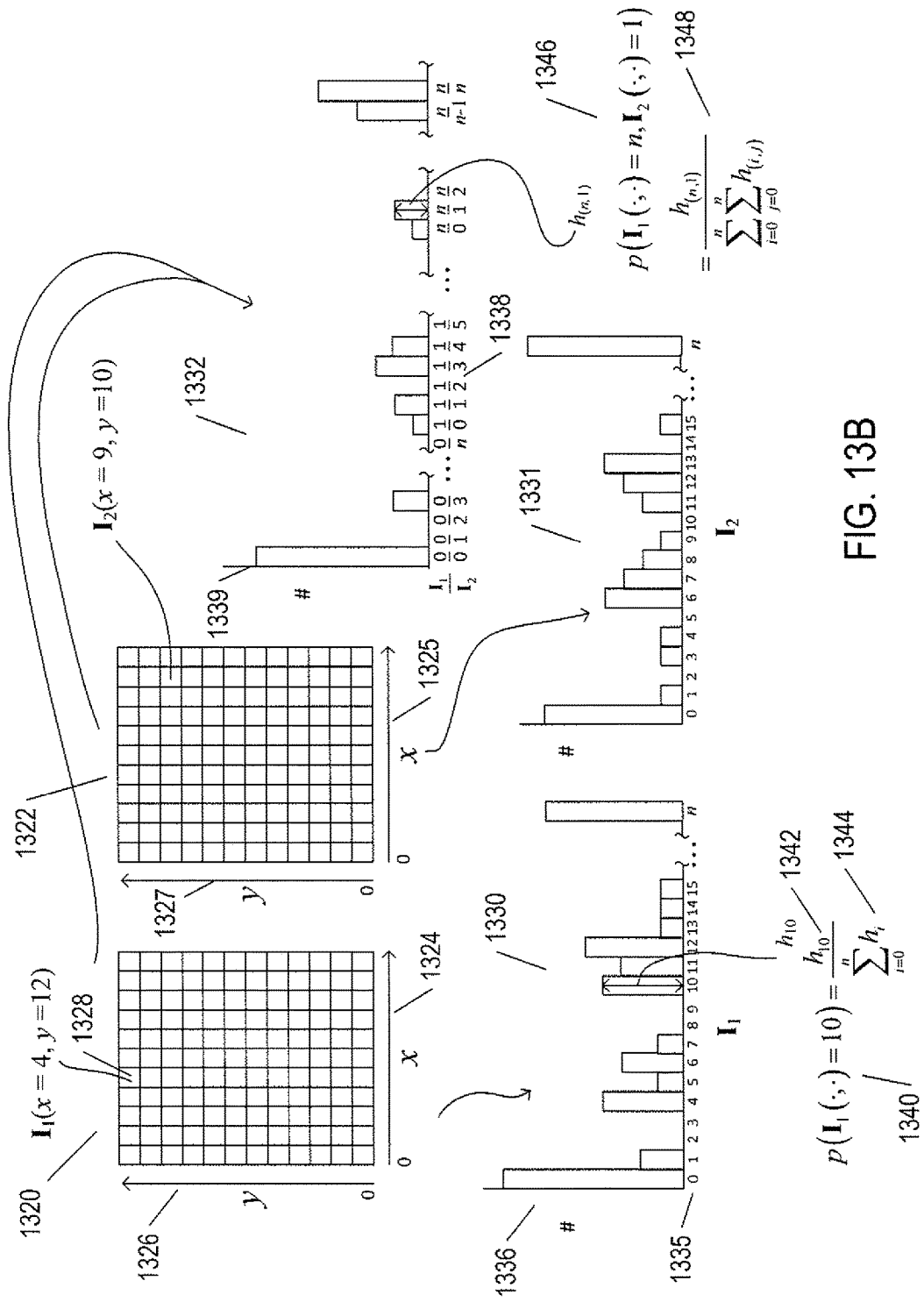

FIGS. 13A-C illustrate computation of a gradient-based cost. A small portion of the pixels in image 1302 are shown at the top of FIG. 13. The pixels are cells within a grid, such as the cell 1304 with grid coordinates (x,y). The gradient at the location of a pixel (x,y) in an image $f$ is a vector 1306 that can be estimated from a discrete pixel-intensity computation 1308. Thus, the gradient vector $\nabla f(x,y)$ can be computed for each pixel or element of an image. The gradient vector 1310 for the pixel $f(x,y)$ 1304 is shown as an example of a gradient associated with a pixel element. By computing the gradient at each pixel in an image, with different methods used to compute certain of the boundary-pixel gradient vectors, an image can be transformed into a vector field. Two images can be compared by computing a comparison value based, in part, on a comparison of the gradient-vector fields of the two images.

FIG. 13B illustrates generation of histograms for the intensity values of two images that are to be compared. The probability that a randomly selected pixel from the images has a particular intensity value can be computed from pixel-intensity histograms. In FIG. 13B, two images 1320 and 1322 are shown. Image 1320 is referred to as image $I_1$ and image 1322 is referred to as image $I_2$. As usual, the pixels within the images are shown as rectangular or square cells and the cells are associated with coordinates with respect to x 1324-1325 and y 1326 and 1327 axes. Each pixel is associated with an intensity value. The intensity value may have different components, depending on the color model used to encode the colors and intensities of the pixel, or may be associated with a single intensity derived from the multiple color/intensity components associated with a pixel. In one implementation, each pixel is associated with an averaged intensity that represents the average of three color-channel intensities. The intensity for a pixel with coordinates (x, y) of image $I_1$ is denoted as $I_1(x, y)$. For example, the intensity of cell 1328 is $I_1(4, 12)$. Histograms 1330-1332 are be prepared from the intensity values of the pixels of the individual images $I_1$ and $I_2$ and for the combination of the two images. For example, histogram 1330 is prepared from image $I_1$. The horizontal axis 1335 of the histogram is incremented in increasing intensity values and the vertical axis 1336 represents the number of pixels in the image having a particular intensity value. Of course, the histograms may be computationally represented by arrays of pixel counts indexed by intensity values. Histogram 1331 is prepared, in similar fashion, from image $I_2$ 1322. The joint histogram 1332 is a histogram showing the number of matching or aligned pixels, in the two images $I_1$ and $I_2$, having a particular ordered pair of intensity values. The horizontal axis 1338 of the joint-image histogram 1332 is incremented in pairs of intensity values and the vertical axis 1339 represents the number of equivalent, aligned pixel pairs having a particular ordered pair of intensities. One pixel of each pair of pixels is selected from the first of the two images and the other pixel of each pair of pixels is selected from the second of the two images, with both pixels of each pair having the same (x, y) coordinates. The histograms can be thought of as discrete probability distributions. For example, the probability that a randomly selected pixel from image $I_1$ has the intensity value 10 1340 can be computed as the number of pixels in image $I_1$ with intensity value 10 1342 divided by the number of pixels in image $I_1$ 1344. In similar fashion, the probability that two aligned and matching pixels and images $I_1$ and $I_2$ have a particular ordered pair of intensity values 1346 is computed as the ratio of the number of pixels of the two images having the ordered pair of intensity values divided by the total number of the pixels in each of the two images 1348.

As shown in FIG. 13C, the intensity probabilities computed for randomly selected pixels of the two images $I_1$ and $I_2$ and joint intensity probabilities for pairs of matching pixels selected from the two images can be represented by alternative, simpler notation 1350. Using this notation, the expressions 1352 show calculation of the Shannon entropy $H_1$, $H_2$, and $H_{1,2}$ for image $I_1$, image $I_2$, and the combination of images $I_1$ and $I_2$, respectively. The mutual information for the two images $I_1$ and $I_2$, $MI(I_1, I_2)$ is then computed, as shown in FIG. 13 1354 from the entropies computed in expressions 1352. A variety of alternative expressions for $MI(I_1, I_2)$ in terms of entropies, joint entropies, and conditional entropies can instead be used to compute $MI(I_1, I_2)$. A cost function that represents a comparison value for two images $I_1$ and $I_2$ is then computed as the negative of the mutual information of the two images multiplied by a computed value $G(I_1, I_2)$, as shown in expression 1356. The computed value $G(I_1, I_2)$ is, as shown in expression 1358, computed as the sum of a function $f()$ computed over all of the pixels of the images. The function $f()$ takes, as arguments, the gradients computed for each pixel (x, y) for the two images and the value in the teeth mask computed for the first of the two images. As shown in expression 1360, the function $f(\ )$ has the value $\cos(a,b)*\sqrt{\text{square root over }(\min(|a|,|b|))}$ when the pixel to which the function is applied is a member of a teeth region in the mask and is otherwise 0. The cost-function value is minimized, by optimization methods discussed above with reference to FIG. 12.

Figure 14:
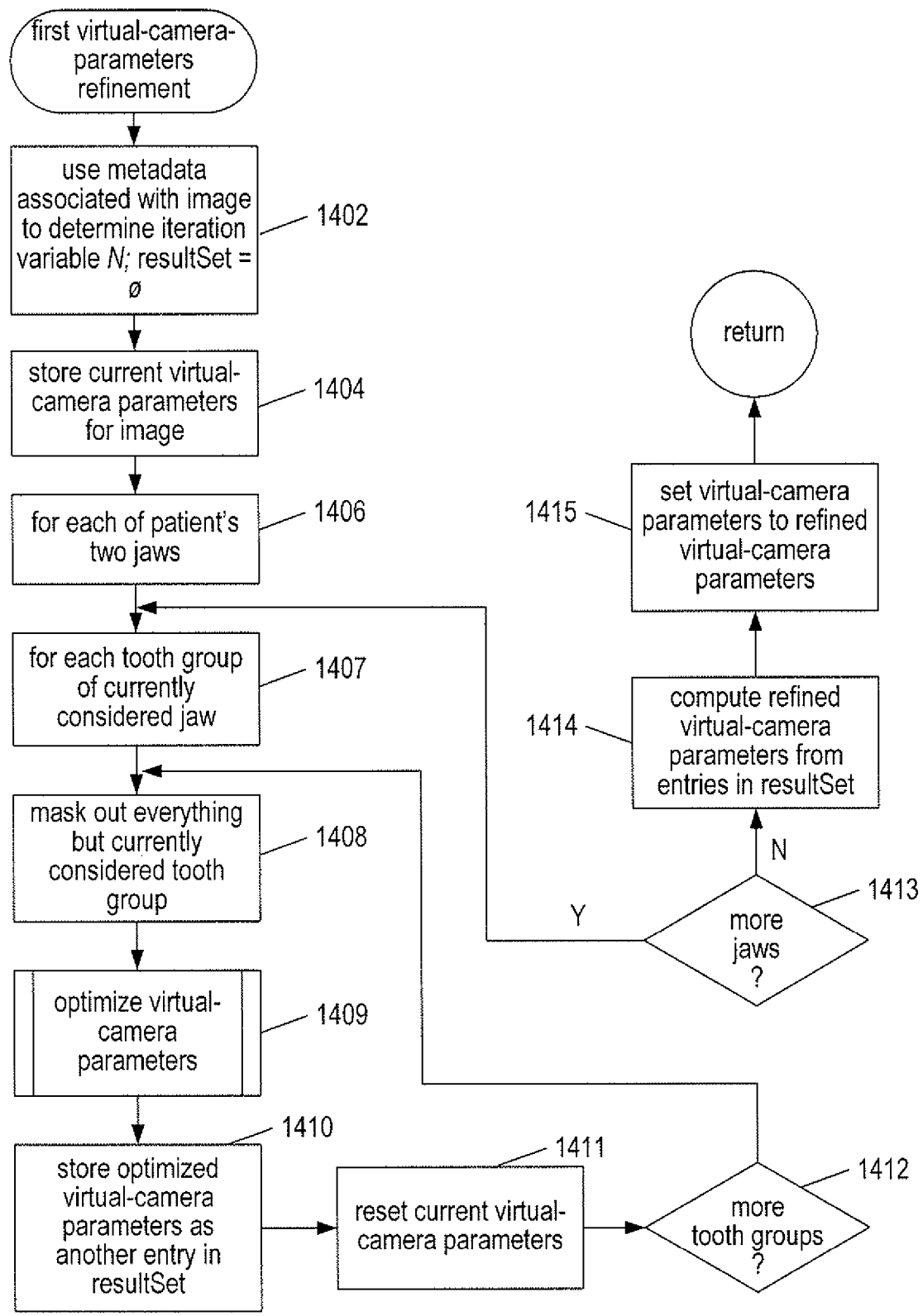
FIG. 14 provides a control-flow diagram for the first virtual-camera-parameters refinement method called in step 807 of FIG. 8.

FIG. 14 provides a control-flow diagram for the first virtual-camera-parameters refinement method called in step 807 of FIG. 8. In step 1402, the metadata associated with the currently considered input image is used to determine the value for an iteration variable N and a set variable resultSet is initialized to be empty. In step 1404, the current virtual-camera parameters for the image are stored. In an outer for-loop of steps 1406, each of the patient's two jaws and associated teeth are separately considered in two iterations. In the inner for-loop of steps 1407-1411, each tooth group of the currently considered jaw is considered 1407. The rest of the image other than the currently considered tooth group is masked out of the image, in step 1408. Then, in step 1409, an optimization procedure equivalent to the optimization procedure discussed above with reference to FIG. 12 is used to optimize the virtual-camera parameters for the currently considered input image. In step 1410, the optimized virtual-camera parameters are stored as a next entry in the set resultSet produced by the inner and outer for-loops of steps 1406-1413. Finally, in step 1411, the current virtual-camera parameters are reset to the stored virtual-camera parameters, stored in step 1404 and repeated for more tooth groups 1412. Following termination of the two nested loops in steps 1406-1413, a refined virtual-camera parameter is computed from the entries stored in the set resultSet by the two nested loops, in step 1414. This computation may involve illuminating outlying results from the results set and then averaging or using a weighted average on the remaining results of the results set. Then, in step 1415, the virtual-camera parameters for the currently considered input image are set to the refined virtual-camera parameters determined in step 1414.

Figure 15:
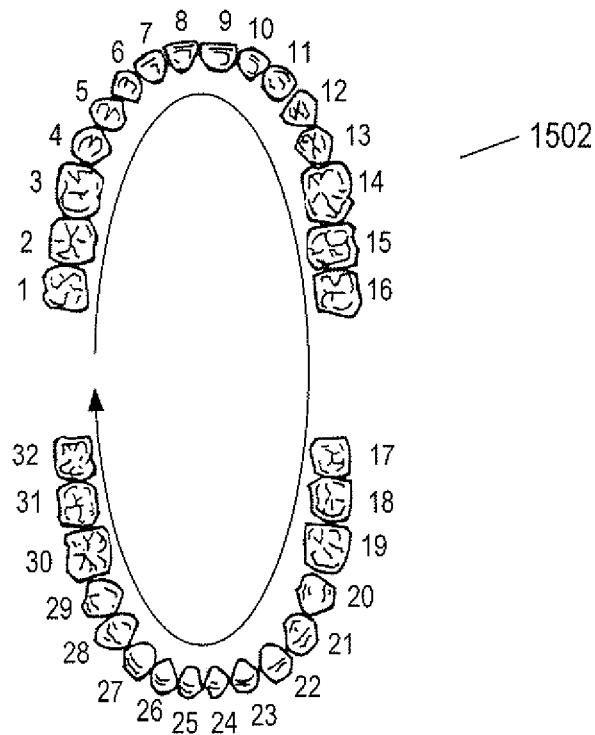
FIG. 15 illustrates examples of the tooth groups over which the inner loop of the method illustrated in FIG. 14 iterates.

FIG. 15 illustrates examples of the tooth groups over which the inner loop of the method illustrated in FIG. 14 iterates. At the top of FIG. 15, a chart indicating the universal numeric code for human teeth is provided 1502. Example tooth groups are shown below the chart, such as example tooth group 1504 consisting of the four teeth 7, 8, 9, and 10. Various different partitionings of teeth into tooth groups can be employed for deriving the multiple iterations of the inner loop of the nested for-loops discussed above with reference to FIG. 14.

Figure 16:
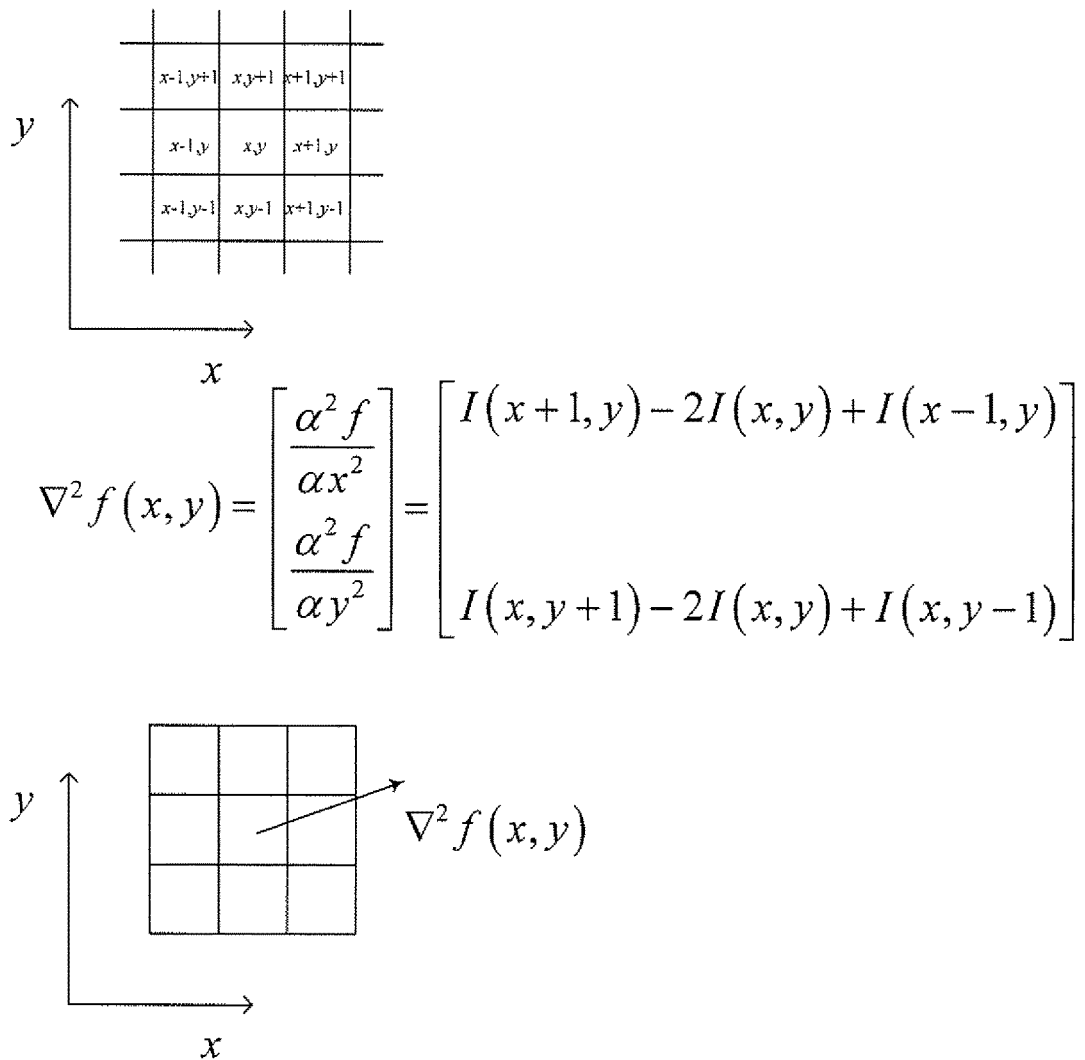
FIG. 16 illustrates, using the same illustration conventions as used in FIG. 13, computation of the Laplacian vectors for image elements and generation of a Laplacian-vector field.

The current discussion has been proceeding through the steps shown in FIG. 8. The second virtual-camera-parameters refinement method, invoked in step 808, uses an optimization method similar to that discussed above with reference to FIG. 12 on the full complement of teeth. The final refinement method, invoked in step 811 of FIG. 8, is similar to the method invoked in step 808, with the exception that the cost is computed from a consideration of the second derivatives of the images at the image elements, or Laplacian vectors, rather than the first derivatives, or gradient vectors. FIG. 16 illustrates, using the same illustration conventions as used in FIG. 13, computation of the Laplacian vectors for image elements and generation of a Laplacian-vector field.

Figure 17A:
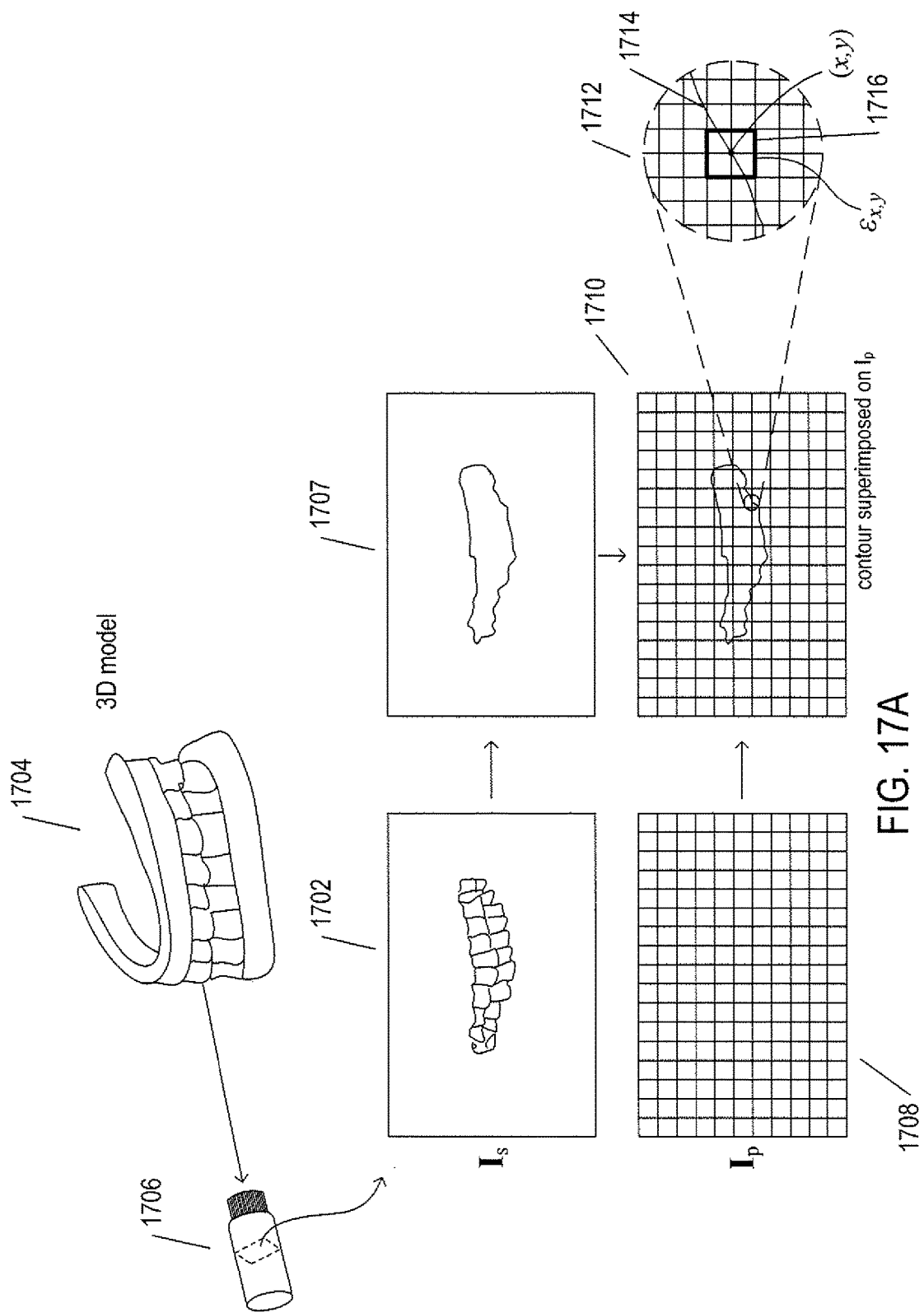

As discussed above with reference to FIGS. 5D and 9, once all the input images are associated with finally refined virtual-camera parameters, a comparison is made between each input image and a corresponding image generated from the three-dimensional model in order to generate a comparison value or correlation coefficient. FIGS. 17A-B illustrate computation of the comparison value or correlation coefficient. As shown in FIG. 17A, a two-dimensional image 1702 $I_\varepsilon$ is generated 1706 from the three-dimensional model 1704 using the virtual-camera parameters determined, as discussed above with reference to FIG. 8, for a corresponding input image $I_p$ 1708. Next, a contour line that encloses the teeth in the image is generated 1707. This contour line is then overlaid or superimposed over the original input image 1708 to produce an overlaid image 1710. As shown in FIG. 17A in inset 1712, for each pixel (x, y) lying along the contour line 1714, a small square, rectangular, or other compact region 1716, $\varepsilon_x$ can be constructed. The comparison values generated from the overlaid image 1710 involve computing the cost of the pixels that lie along the contour in both the input image $I_p$ and the image generated from the three-dimensional model $I_s$. The cost for a contour-overlapping pixel (x, y) is computed as shown in expression 1720 in FIG. 17B. When the absolute values or magnitudes of the gradients for pixel (x, y) in both images is greater than a threshold T, which has the value 3 in one implementation, the cost for the pixel is the dot product of the gradients for the pixel in the two images divided by the product of the magnitudes of the two gradients. Otherwise, the cost is 0. A fitness or similarity metric can be computed, as shown in equation 1722, as the sum of the costs of the pixels lying along the contour divided by the length of the contour, in pixels. An alternative fitness or similarity metric is shown in expression 1724. In the alternative fitness value, the cost for the two images is computed as the sum of the cost of the pixels along the contour divided by the sum of the maximum cost of any pixel in the region $\varepsilon_{x,y}$ for each of the pixels in the two images (x, y). This alternative metric has greater reliability when input images are slightly blurred by applying a Gaussian filter. Either fitness value or a linear combination of the two fitness values may be used as the computed similarity metric or correlation coefficient for the comparison of the two images.

It should be noted that, in general, color images are processed by the monitoring method. When gradients and Laplacian vectors are computed, they are computed based on an overall luminance or intensity computed from the three different color values of whatever color scheme is used to encode the images.

Figure 18:
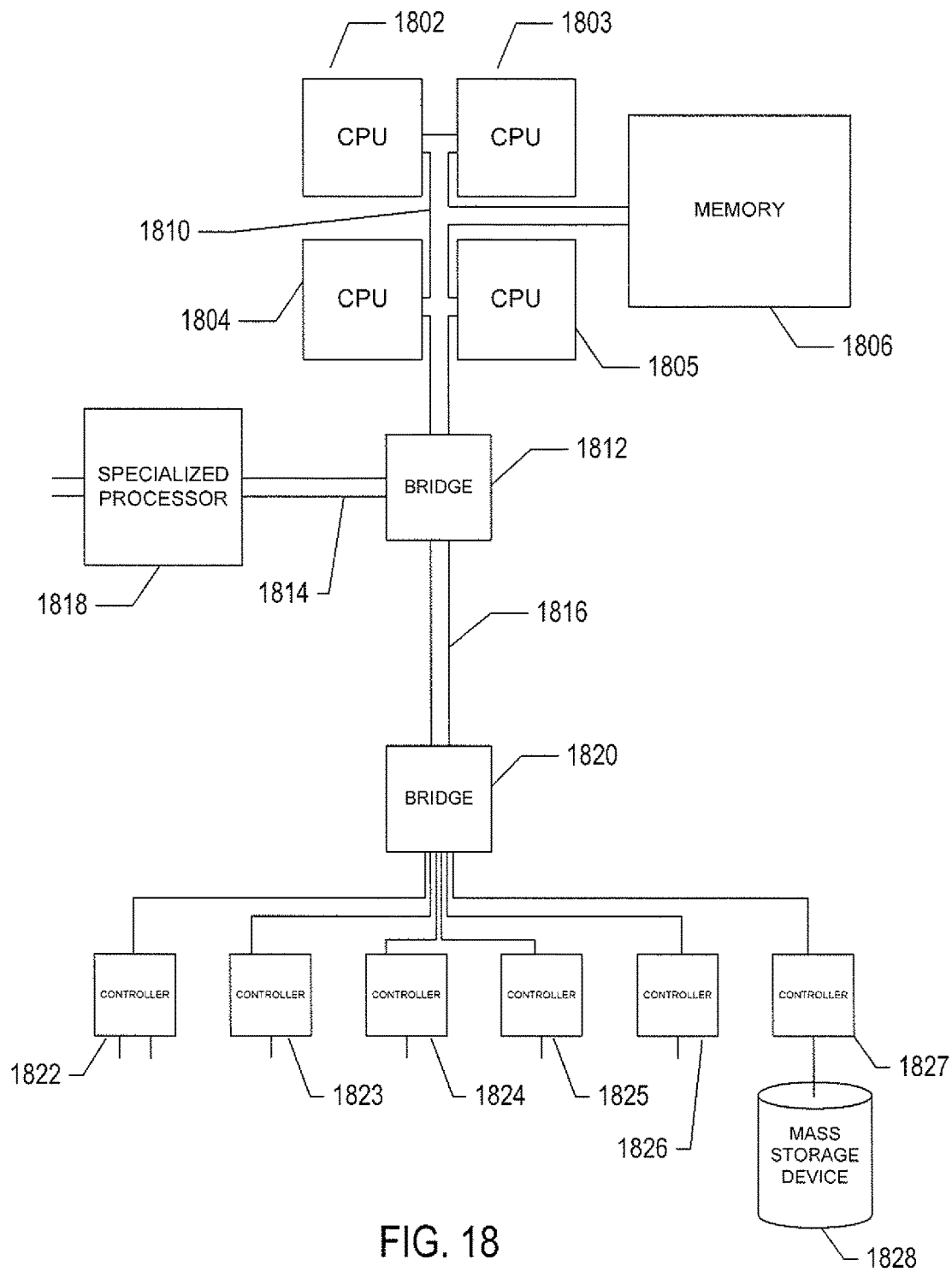
FIG. 18 provides a general architectural diagram for various types of computers, including computers used to implement dental-treatment monitoring systems.

FIG. 18 provides a general architectural diagram for various types of computers, including computers used to implement dental-treatment monitoring systems. The computer system contains one or multiple central processing units ("CPUs") 1802-1805, one or more electronic memories 1806 interconnected with the CPUs by a CPU/memory-subsystem bus 1810 or multiple busses, a first bridge 1812 that interconnects the CPU/memory-subsystem bus 1810 with additional busses 1814 and 1816, or other types of high-speed interconnection media, including multiple, high-speed serial interconnects. These busses or serial interconnections, in turn, connect the CPUs and memory with specialized processors, such as a graphics processor 1818, and with one or more additional bridges 1820, which are interconnected with high-speed serial links or with multiple controllers 1822-1827, such as controller 1827, that provide access to various different types of mass-storage devices 1828, electronic displays, input devices, and other such components, subcomponents, and computational resources. It should be noted that computer-readable data-storage devices include optical and electromagnetic disks, electronic memories, and other physical data-storage devices. Those familiar with modern science and technology appreciate that electromagnetic radiation and propagating signals do not store data for subsequent retrieval, and can transiently "store" only a byte or less of information per mile, far less information than needed to encode even the simplest of routines.

Of course, there are many different types of computer-system architectures that differ from one another in the number of different memories, including different types of hierarchical cache memories, the number of processors and the connectivity of the processors with other system components, the number of internal communications busses and serial links, and in many other ways. However, computer systems generally execute stored programs by fetching instructions from memory and executing the instructions in one or more processors.

Figure 19:
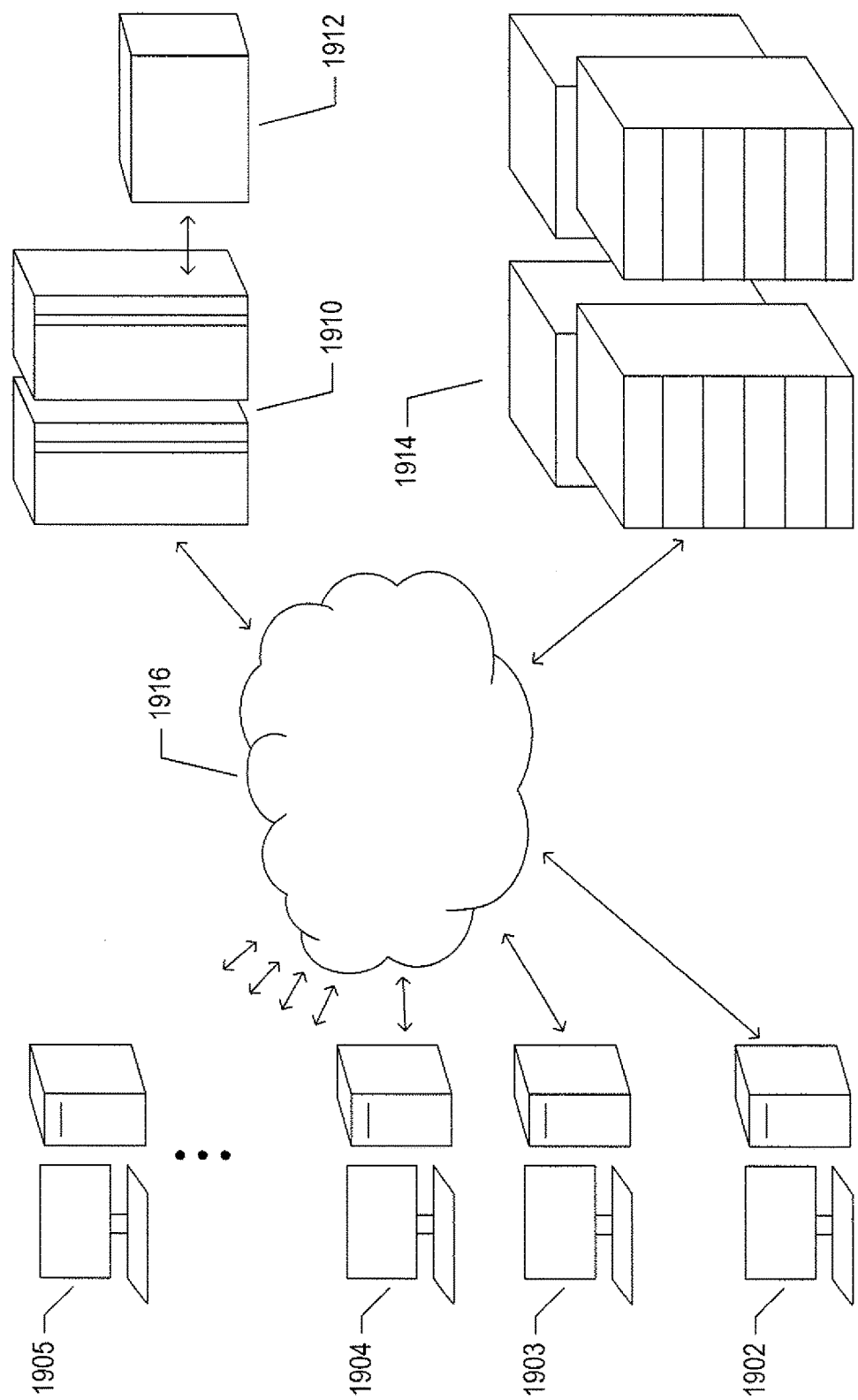
FIG. 19 illustrates an Internet-connected distributed computer system.

FIG. 19 illustrates an Internet-connected distributed computer system. As communications and networking technologies have evolved in capability and accessibility, and as the computational bandwidths, data-storage capacities, and other capabilities and capacities of various types of computer systems have steadily and rapidly increased, much of modern computing now generally involves large distributed systems and computers interconnected by local networks, wide-area networks, wireless communications, and the Internet. FIG. 19 shows a typical distributed system in which a large number of PCs 1902-1905, a high-end distributed mainframe system 1910 with a large data-storage system 1912, and a large computer center 1914 with large numbers of rack-mounted servers or blade servers all interconnected through various communications and networking systems that together comprise the Internet 1916. Such distributed computing systems provide diverse arrays of functionalities. For example, a PC user sitting in a home office may access hundreds of millions of different web sites provided by hundreds of thousands of different web servers throughout the world and may access high-computational-bandwidth computing services from remote computer facilities for running complex computational tasks.

Until recently, computational services were generally provided by computer systems and data centers purchased, configured, managed, and maintained by service-provider organizations. For example, an e-commerce retailer generally purchased, configured, managed, and maintained a data center including numerous web servers, back-end computer systems, and data-storage systems for serving web pages to remote customers, receiving orders through the web-page interface, processing the orders, tracking completed orders, and other myriad different tasks associated with an e-commerce enterprise.

Figure 20:
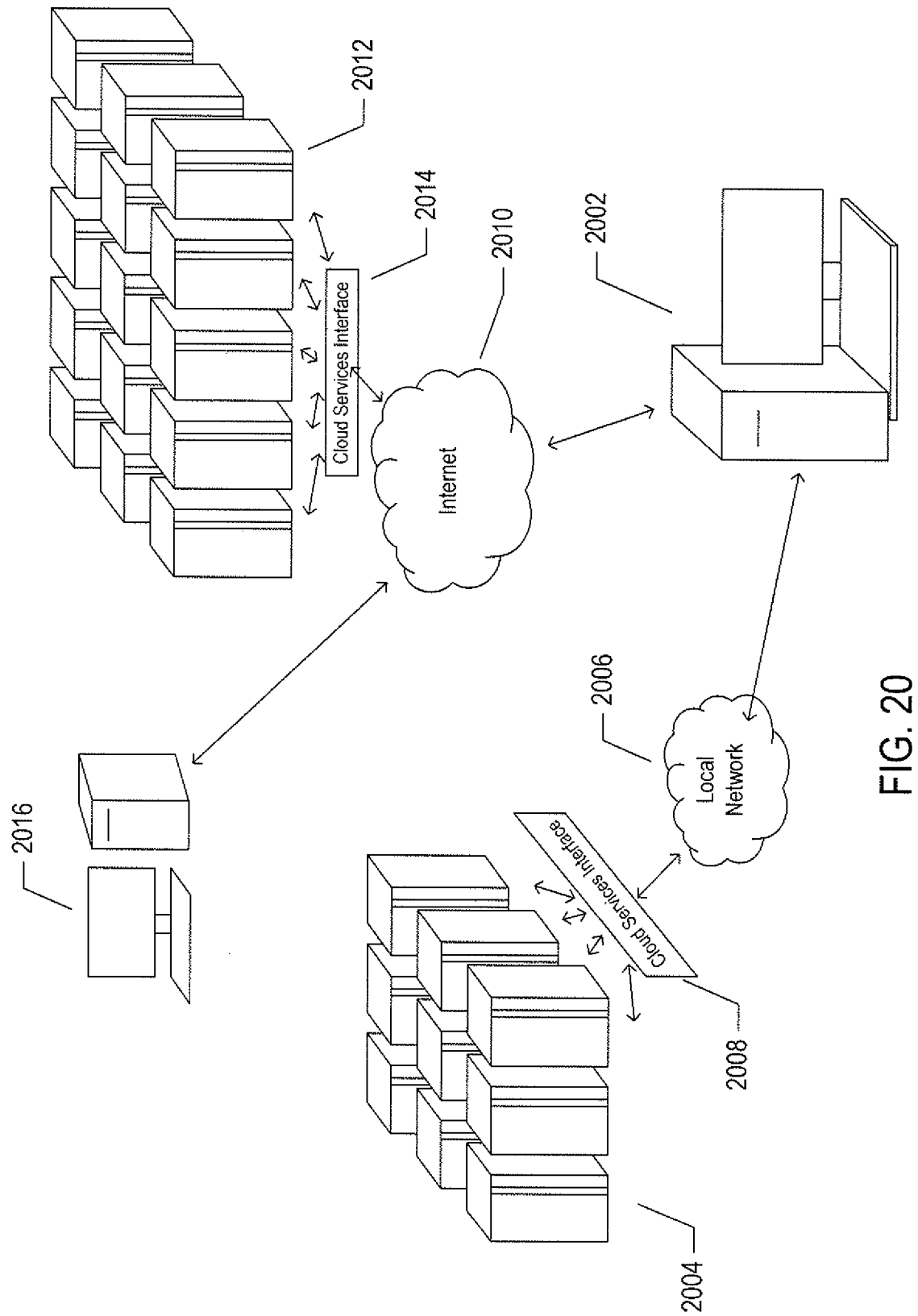
FIG. 20 illustrates cloud computing.

FIG. 20 illustrates cloud computing. In the recently developed cloud-computing paradigm, computing cycles and data-storage facilities are provided to organizations and individuals by cloud-computing providers. In addition, larger organizations may elect to establish private cloud-computing facilities in addition to, or instead of, subscribing to computing services provided by public cloud-computing service providers. In FIG. 20, a system administrator for an organization, using a PC 2002, accesses the organization's private cloud 2004 through a local network 2006 and private-cloud interface 2008 and also accesses, through the Internet 2010, a public cloud 2012 through a public-cloud services interface 2014. The administrator can, in either the case of the private cloud 2004 or public cloud 2012, configure virtual computer systems and even entire virtual data centers and launch execution of application programs on the virtual computer systems and virtual data centers in order to carry out any of many different types of computational tasks. As one example, a small organization may configure and run a virtual data center within a public cloud that executes web servers to provide an e-commerce interface through the public cloud to remote customers of the organization, such as a user viewing the organization's e-commerce web pages on a remote user system 2016.

Cloud-computing facilities are intended to provide computational bandwidth and data-storage services much as utility companies provide electrical power and water to consumers. Cloud computing provides enormous advantages to small organizations without the resources to purchase, manage, and maintain in-house data centers. Such organizations can dynamically add and delete virtual computer systems from their virtual data centers within public clouds in order to track computational-bandwidth and data-storage needs, rather than purchasing sufficient computer systems within a physical data center to handle peak computational-bandwidth and data-storage demands. Moreover, small organizations can completely avoid the overhead of maintaining and managing physical computer systems, including hiring and periodically retraining information-technology specialists and continuously paying for operating-system and database-management-system upgrades. Furthermore, cloud-computing interfaces allow for easy and straightforward configuration of virtual computing facilities, flexibility in the types of applications and operating systems that can be configured, and other functionalities that are useful even for owners and administrators of private cloud-computing facilities used by a single organization.

Figure 21:
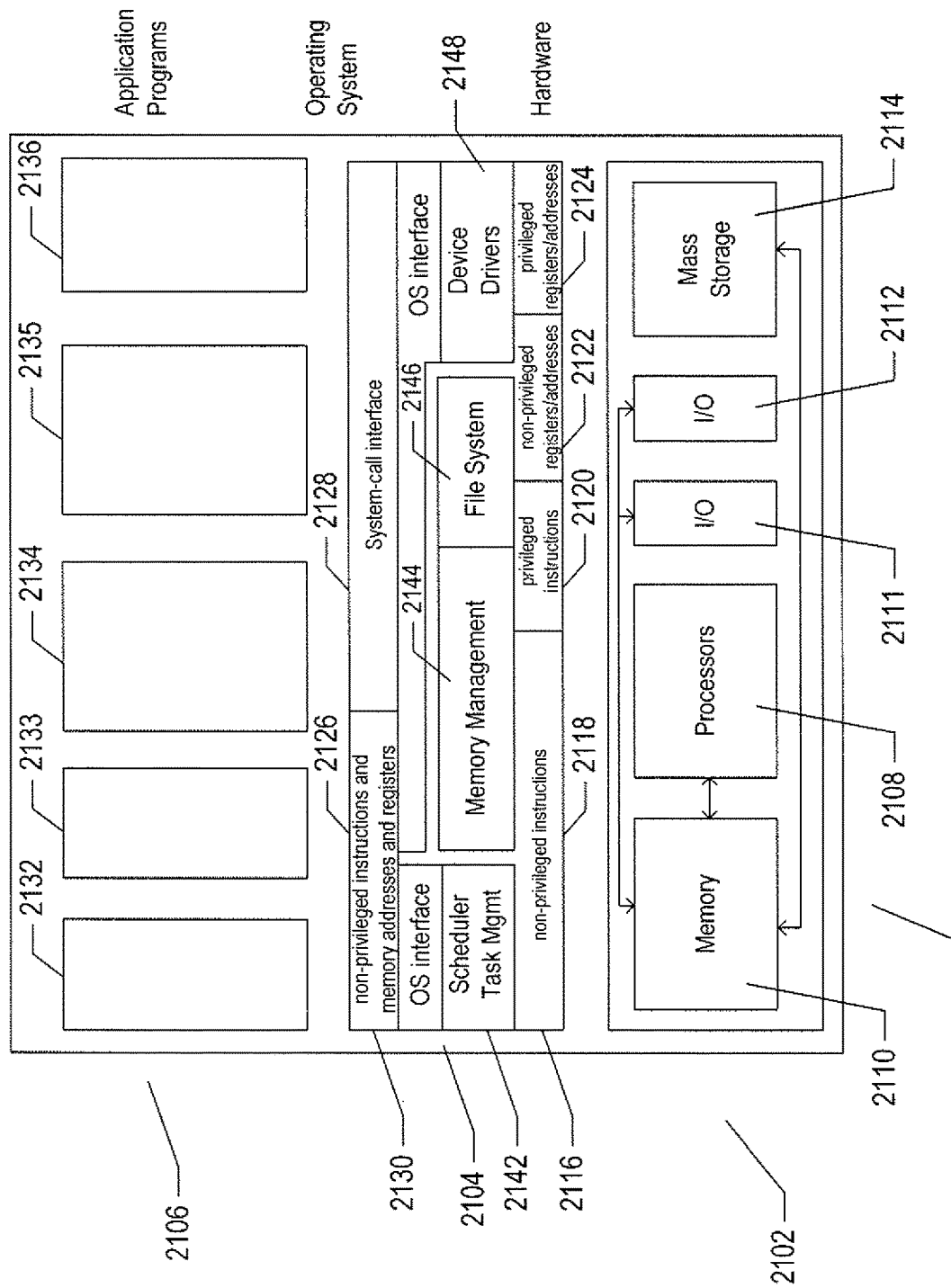
FIG. 21 illustrates generalized hardware and software components of a general-purpose computer system, such as a general-purpose computer system having an architecture similar to that shown in FIG. 1.

FIG. 21 illustrates generalized hardware and software components of a general-purpose computer system, such as a general-purpose computer system having an architecture similar to that shown in FIG. 1. The computer system 2100 is often considered to include three fundamental layers: (1) a hardware layer or level 2102; (2) an operating-system layer or level 2104; and (3) an application-program layer or level 2106. The hardware layer 2102 includes one or more processors 2108, system memory 2110, various different types of input-output ("I/O") devices 2111 and 2112, and mass-storage devices 2114. Of course, the hardware level also includes many other components, including power supplies, internal communications links and busses, specialized integrated circuits, many different types of processor-controlled or microprocessor-controlled peripheral devices and controllers, and many other components. The operating system 2104 interfaces to the hardware level 2102 through a low-level operating system and hardware interface 2116 generally comprising a set of non-privileged computer instructions 2118, a set of privileged computer instructions 2120, a set of non-privileged registers and memory addresses 2122, and a set of privileged registers and memory addresses 2124. In general, the operating system exposes non-privileged instructions, non-privileged registers, and non-privileged memory addresses 2126 and a system-call interface 2128 as an operating-system interface 2130 to application programs 2132-2136 that execute within an execution environment provided to the application programs by the operating system. The operating system, alone, accesses the privileged instructions, privileged registers, and privileged memory addresses. By reserving access to privileged instructions, privileged registers, and privileged memory addresses, the operating system can ensure that application programs and other higher-level computational entities cannot interfere with one another's execution and cannot change the overall state of the computer system in ways that could deleteriously impact system operation. The operating system includes many internal components and modules, including a scheduler 2142, memory management 2144, a file system 2146, device drivers 2148, and many other components and modules. To a certain degree, modern operating systems provide numerous levels of abstraction above the hardware level, including virtual memory, which provides to each application program and other computational entities a separate, large, linear memory-address space that is mapped by the operating system to various electronic memories and mass-storage devices. The scheduler orchestrates interleaved execution of various different application programs and higher-level computational entities, providing to each application program a virtual, stand-alone system devoted entirely to the application program. From the application program's standpoint, the application program executes continuously without concern for the need to share processor resources and other system resources with other application programs and higher-level computational entities. The device drivers abstract details of hardware-component operation, allowing application programs to employ the system-call interface for transmitting and receiving data to and from communications networks, mass-storage devices, and other I/O devices and subsystems. The file system 2136 facilitates abstraction of mass-storage-device and memory resources as a high-level, easy-to-access, file-system interface. Thus, the development and evolution of the operating system has resulted in the generation of a type of multi-faceted virtual execution environment for application programs and other higher-level computational entities.

While the execution environments provided by operating systems have proved to be an enormously successful level of abstraction within computer systems, the operating-system-provided level of abstraction is nonetheless associated with difficulties and challenges for developers and users of application programs and other higher-level computational entities. One difficulty arises from the fact that there are many different operating systems that run within various different types of computer hardware. In many cases, popular application programs and computational systems are developed to run on only a subset of the available operating systems, and can therefore be executed within only a subset of the various different types of computer systems on which the operating systems are designed to run. Often, even when an application program or other computational system is ported to additional operating systems, the application program or other computational system can nonetheless run more efficiently on the operating systems for which the application program or other computational system was originally targeted. Another difficulty arises from the increasingly distributed nature of computer systems. Although distributed operating systems are the subject of considerable research and development efforts, many of the popular operating systems are designed primarily for execution on a single computer system. In many cases, it is difficult to move application programs, in real time, between the different computer systems of a distributed computer system for high-availability, fault-tolerance, and load-balancing purposes. The problems are even greater in heterogeneous distributed computer systems which include different types of hardware and devices running different types of operating systems. Operating systems continue to evolve, as a result of which certain older application programs and other computational entities may be incompatible with more recent versions of operating systems for which they are targeted, creating compatibility issues that are particularly difficult to manage in large distributed systems.

Figure 22A:
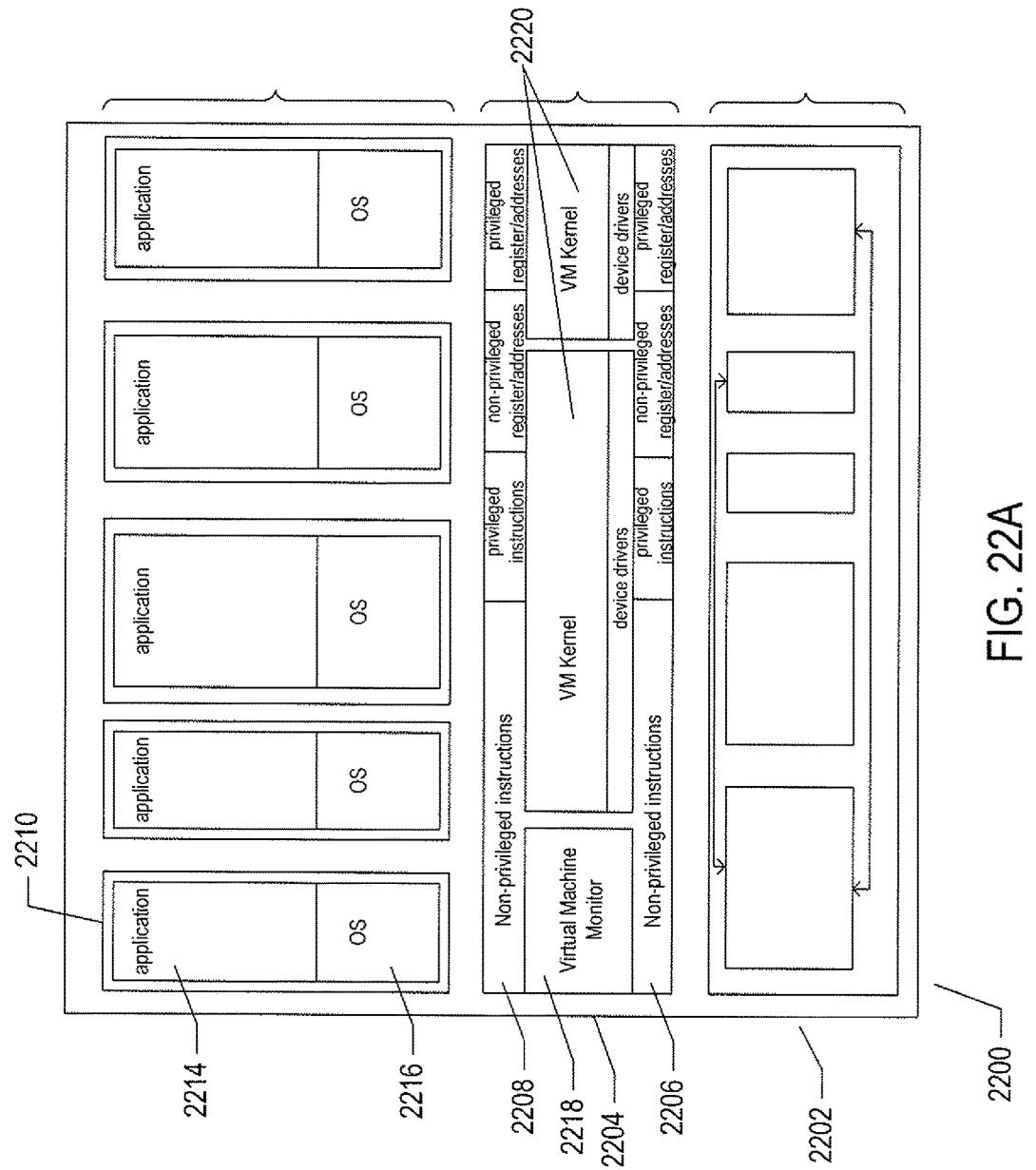
FIGS. 22A-B illustrate two types of virtual machine and virtual-machine execution environments.
Figure 22B:
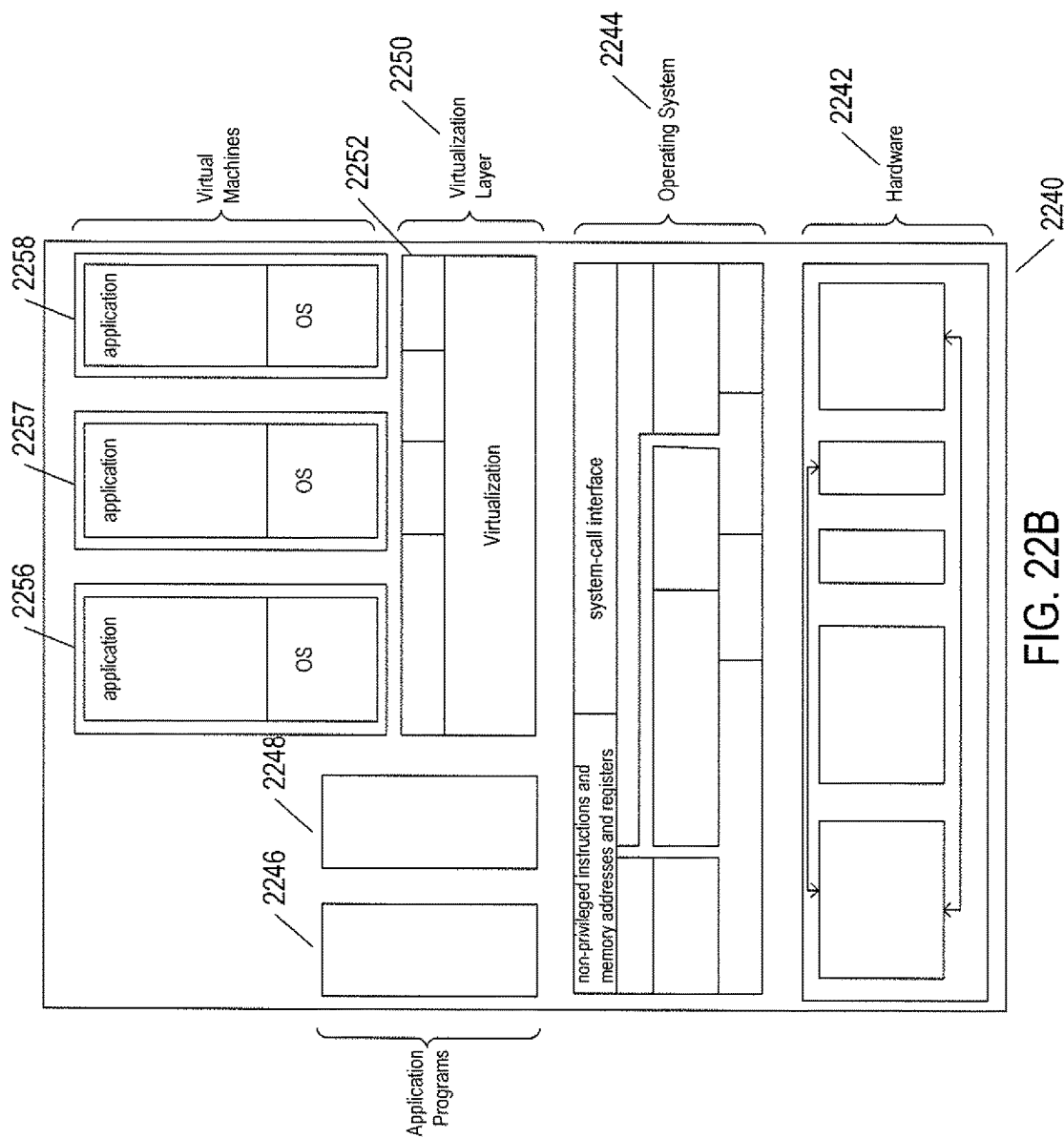

For all of these reasons, a higher level of abstraction, referred to as the "virtual machine," has been developed and evolved to further abstract computer hardware in order to address many difficulties and challenges associated with traditional computing systems, including the compatibility issues discussed above. FIGS. 22A-B illustrate two types of virtual machine and virtual-machine execution environments. FIGS. 22A-B use the same illustration conventions as used in FIG. 21. FIG. 22A shows a first type of virtualization. The computer system 2200 in FIG. 22A includes the same hardware layer 2202 as the hardware layer 2102 shown in FIG. 21. However, rather than providing an operating system layer directly above the hardware layer, as in FIG. 21, the virtualized computing environment illustrated in FIG. 22A features a virtualization layer 2204 that interfaces through a virtualization-layer/hardware-layer interface 2206, equivalent to interface 2116 in FIG. 21, to the hardware. The virtualization layer provides a hardware-like interface 2208 to a number of virtual machines, such as virtual machine 2210, executing above the virtualization layer in a virtual-machine layer 2212. Each virtual machine includes one or more application programs or other higher-level computational entities packaged together with an operating system, referred to as a "guest operating system," such as application 2214 and guest operating system 2216 packaged together within virtual machine 2210. Each virtual machine is thus equivalent to the operating-system layer 2104 and application-program layer 2106 in the general-purpose computer system shown in FIG. 21. Each guest operating system within a virtual machine interfaces to the virtualization-layer interface 2208 rather than to the actual hardware interface 2206. The virtualization layer partitions hardware resources into abstract virtual-hardware layers to which each guest operating system within a virtual machine interfaces. The guest operating systems within the virtual machines, in general, are unaware of the virtualization layer and operate as if they were directly accessing a true hardware interface. The virtualization layer ensures that each of the virtual machines currently executing within the virtual environment receive a fair allocation of underlying hardware resources and that all virtual machines receive sufficient resources to progress in execution. The virtualization-layer interface 2208 may differ for different guest operating systems. For example, the virtualization layer is generally able to provide virtual hardware interfaces for a variety of different types of computer hardware. This allows, as one example, a virtual machine that includes a guest operating system designed for a particular computer architecture to run on hardware of a different architecture. The number of virtual machines need not be equal to the number of physical processors or even a multiple of the number of processors.

The virtualization layer includes a virtual-machine-monitor module 2218 ("VMM") that virtualizes physical processors in the hardware layer to create virtual processors on which each of the virtual machines executes. For execution efficiency, the virtualization layer attempts to allow virtual machines to directly execute non-privileged instructions and to directly access non-privileged registers and memory. However, when the guest operating system within a virtual machine accesses virtual privileged instructions, virtual privileged registers, and virtual privileged memory through the virtualization-layer interface 2208, the accesses result in execution of virtualization-layer code to simulate or emulate the privileged resources. The virtualization layer additionally includes a kernel module 2220 that manages memory, communications, and data-storage machine resources on behalf of executing virtual machines ("VM kernel"). The VM kernel, for example, maintains shadow page tables on each virtual machine so that hardware-level virtual-memory facilities can be used to process memory accesses. The VM kernel additionally includes routines that implement virtual communications and data-storage devices as well as device drivers that directly control the operation of underlying hardware communications and data-storage devices. Similarly, the VM kernel virtualizes various other types of I/O devices, including keyboards, optical-disk drives, and other such devices. The virtualization layer essentially schedules execution of virtual machines much like an operating system schedules execution of application programs, so that the virtual machines each execute within a complete and fully functional virtual hardware layer.

FIG. 22B illustrates a second type of virtualization. In FIG. 22B, the computer system 2240 includes the same hardware layer 2242 and software layer 2244 as the hardware layer 2102 shown in FIG. 21. Several application programs 2246 and 2248 are shown running in the execution environment provided by the operating system. In addition, a virtualization layer 2250 is also provided, in computer 2240, but, unlike the virtualization layer 2204 discussed with reference to FIG. 22A, virtualization layer 2250 is layered above the operating system 2244, referred to as the "host OS," and uses the operating system interface to access operating-system-provided functionality as well as the hardware. The virtualization layer 2250 comprises primarily a VMM and a hardware-like interface 2252, similar to hardware-like interface 2208 in FIG. 22A. The virtualization-layer/hardware-layer interface 2252, equivalent to interface 2116 in FIG. 21, provides an execution environment for a number of virtual machines 2256-2258, each including one or more application programs or other higher-level computational entities packaged together with a guest operating system.

Dental-monitoring systems may be implemented using single PCs or servers, may be implemented in distributed computing systems, or may be implemented using cloud-computing facilities. Similarly, practitioners may communicate with a dental-monitoring system using a PC, server, or many other processor-controlled devices, including tablets, lap tops, and smart phones.

Although the present invention has been described in terms of particular embodiments, it is not intended that the invention be limited to these embodiments. Modifications within the spirit of the invention will be apparent to those skilled in the art. For example, any of many different design and implementation parameters, including operating system, hardware platform, programming language, modular organization, control structures, data structures, and other such parameters may be varied to produce various alternative implementations. As another example, the two-dimensional images acquired from patients during treatments can be obtained by using any of a wide variety of different imaging devices, including two-dimensional digital cameras, three-dimensional digital cameras, film-based cameras with digital-conversion devices, and even non-optical imaging devices.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A dental-treatment monitoring system comprising:
one or more processors;
one or more electronic memories that store instructions and data;
one or more mass-storage devices that store encoded images and patient information;
a communications subsystem through which the dental-treatment monitoring system receives images and information from remote computer systems; and
computer instructions, encoded in one or more of the one or more electronic memories, that control the dental-treatment monitoring system to store, in one or more data-storage devices selected from among the one or more electronic memories and one or more mass-storage devices, a three-dimensional model of a patient's teeth, receive, through the communications subsystem, one or more two-dimensional digital photographs of the patient's teeth taken at a time t during the course of a dental treatment, project, in time, the three-dimensional model of the patient's teeth to the time t to generate and store a time-projected three-dimensional model of the patient's teeth representing an expected configuration of the patient's teeth, compare one or more of the one or more two-dimensional digital photographs to corresponding two-dimensional digital images generated from the time-projected three-dimensional model of the patient's teeth to generate one or more comparison values and generate, from the received one or more two-dimensional digital photographs, a set of one or more processed images with associated metadata for analysis, determine, for each image in the set of one or more processed images, a set of virtual-camera parameters that describe the position, and orientation for a virtual camera that produces a generated image from the time-projected three-dimensional model of the patient's teeth equivalent to the image in the set of one or more processed images, use, for each image in the set of one or more processed images, the standard type of view and additional metadata to generate an initial set of virtual-camera parameters for the image in the set of one or more processed images, use the standard type of view and additional metadata to determine a value for an iteration variable; carry out a number of optimization iterations equal to the value of the iteration variable; and finally refine the virtual-camera parameters for the image in the set of one or more processed images, generate, for each image in the set of one or more processed images, a generated image corresponding to the image from the time-projected three-dimensional model of the patient's teeth and the virtual-camera parameters determined for the image in the set of one or more processed images, and compare each image in the set of one or more processed images with the corresponding generated image to generate the one or more comparison values for the image in the set of one or more processed images, determine, from the one or more comparison values, whether or not a configuration of the patient's teeth is within a threshold level of correspondence to the expected configuration of the patient's teeth, and store an indication of the determination in one of the one or more electronic memories.

2. The dental-treatment monitoring system of claim 1 wherein the received two-dimensional digital photographs are associated with a patient identifier; and wherein each of the received two-dimensional digital photographs are associated with metadata that includes one or more of: one or more text labels for the two-dimensional image, including an indication of a standard type of view represented by the image, and characterizations and parameters for the digitally encoded image, including an image size, date and time information, an indication of a camera model and make, an indication of a camera orientation, an indication of an aperture, an indication of a shutter speed, an indication of a focal length, an indication of a metering mode, and an indication of a speed.

3. The dental-treatment monitoring system of claim 2 further comprises verifying and filtering, by the dental-treatment monitoring system, the patient ID and the received two-dimensional digital photographs and associated metadata to produce a set of one or more processed images for analysis by: accessing stored information to verify that the patient ID corresponds to a patient record; for each input image, determining that the image corresponds to the standard type of view indicated by the one or more text labels, applying filters and contrast adjustment to enhance the image for subsequent processing, when the image is the first image of a standard type of view, adding the image and associated metadata to the set of one or more processed images, and when the image has the same standard type of view as an image already added to the set of one or more processed images, replacing the image already added to the set of one or more processed images with the image and associated metadata; and determining whether the set of one or more processed images can be used for dental-treatment-progress analysis.

4. The dental-treatment monitoring system of claim 1 wherein each optimization iteration includes: a first adjustment of the current virtual-camera parameters for the image in the set of one or more processed images; a second adjustment of the current virtual-camera parameters for the image; a first refinement of the current virtual-camera parameters for the image; and a second refinement of the current virtual-camera parameters for the image.

5. The dental-treatment monitoring system of claim 4, further comprising, for each optimization iteration, thresholding the image to generate a first teeth mask for the image; thresholding a next corresponding image generated from the time-projected three-dimensional model of the patient's teeth using the current virtual-camera parameters for the image to generate a next second corresponding teeth mask, generating a distance transform of the first teeth mask, searching over scalings, rotations, and translations of the next second corresponding teeth mask to identify a next minimum-cost overlay of the next second corresponding teeth mask over the distance transform of the first teeth mask, and adjusting the virtual-camera parameters for the image corresponding to the next minimum-cost overlay; and selecting, as the adjusted virtual-camera parameters for the image, the virtual-camera parameters associated with lowest-cost overlay of any of the generated next second corresponding teeth mask over the distance transform of the first teeth mask.

6. The dental-treatment monitoring system of claim 5 wherein the cost of an overlay of a next second corresponding teeth mask over the distance transform of the first teeth mask is the sum of the distances associated with pixels in the distance transform of the first teeth underlying a tooth region within the next second corresponding teeth mask.

7. The dental-treatment monitoring system of claim 5 wherein adjusting the virtual-camera parameters for the image corresponding to the next minimum-cost overlay includes: adjusting the virtual-camera parameters to move the position of the center of the next corresponding image generated from the time-projected three-dimensional model of the patient's teeth; adjusting the virtual-camera parameters to rotate the next corresponding image generated from the time-projected three-dimensional model of the patient's teeth in the image plane; adjusting the virtual-camera parameters to rotate the next corresponding image generated from the time-projected three-dimensional model of the patient's teeth about an axis parallel to the image plane; adjusting the virtual-camera parameters to rescale the next corresponding image generated from the time-projected three-dimensional model of the patient's teeth.

8. The dental-treatment monitoring system of claim 4 wherein the second adjustment of the current virtual-camera parameters for the image comprises: for each of the patient's two jaws, masking out the other of the two jaws and associated teeth from the image, and optimizing the virtual-camera parameters for the image with respect to a pixel-associated cost for the image and a next corresponding image.

9. The dental-treatment monitoring system of claim 8 wherein the cost for the image and a next corresponding image is computed as a linear combination of the mutual information for the image and the next corresponding image and the sum of pixel-associated costs for the image and the next corresponding image based on a dot-product result for gradient vectors for the image and the next corresponding image computed for each pixel.

10. The dental-treatment monitoring system of claim 8 wherein optimizing the virtual-camera parameters for the image comprises: for each optimization iteration, generating a next corresponding image generated from the time-projected three-dimensional model of the patient's teeth using the current virtual-camera parameters for the image, computing a cost for the image and next corresponding image, and perturbing the virtual-camera parameters for the image in a direction that minimizes the cost for the image and next corresponding image.

11. The dental-treatment monitoring system of claim 8 wherein optimizing the virtual-camera parameters for the image comprises application of a Nelder-Mead downhill simplex optimization method, with seven dimensions, including three rotations, three translations, and the virtual-camera view angle.

12. The dental-treatment monitoring system of claim 4 wherein the first refinement of the current virtual-camera parameters for the image comprises: for each of the patient's two jaws, for each tooth group of the currently considered jaw, masking the image to leave the currently considered tooth group, and optimizing the virtual-camera parameters for the image with respect to a gradient-vector-based cost for the image and a next corresponding image.

13. The dental-treatment monitoring system of claim 4 wherein the second refinement of the current virtual-camera parameters for the image comprises: for each of the patient's two jaws, for each tooth group of the currently considered jaw, masking the image to leave the currently considered tooth group, and optimizing the virtual-camera parameters for the image with respect to a Laplacian-vector-based cost for the image and a next corresponding image.

14. The dental-treatment monitoring system of claim 1 wherein comparing each image in the set of one or more processed images with the corresponding generated image to generate a comparison value for the image further comprises: for each image, preparing a teeth contour from the corresponding generated image; overlaying the teeth contour onto the image; and generating a fitness metric for the image, corresponding image, and overlaid contour.

15. The dental-treatment monitoring system of claim 14 wherein the fitness metric is based on a per-pixel cost equal to the normalized dot product of gradient vectors for the image and corresponding image computed for a pixel.

16. The dental-treatment monitoring system of claim 15 wherein the fitness metric is the sum of the per-pixel costs for pixels overlying the contour divided by the length of the contour.

17. The dental-treatment monitoring system of claim 15 wherein the fitness metric is the sum of the per-pixel costs for pixels overlying the contour divided by the sum of maximum costs of pixels within a compact neighborhood that includes each pixel overlying the contour.

18. A method carried out within a dental-treatment monitoring system having one or more processors, one or more electronic memories that store instructions and data, one or more mass-storage devices that store encoded images and patient information, and a communications subsystem through which the dental-treatment monitoring system receives images and information from remote computer systems, the method comprising: storing, in one or more data-storage devices selected from among the one or more electronic memories and one or more mass-storage devices, a three-dimensional model of a patient's teeth; receiving, through the communications subsystem, one or more two-dimensional digital photographs of the patient's teeth taken at a time t during the course of a dental treatment, projecting, in time, the three-dimensional model of the patient's teeth to the time t to generate and store a time-projected three-dimensional model of the patient's teeth representing an expected configuration of the patient's teeth; comparing one or more of the one or more two-dimensional digital photographs to corresponding two-dimensional digital images generated from the time-projected three-dimensional model of the patient's teeth to generate one or more comparison values; generating, from the received one or more two-dimensional digital photographs, a set of one or more processed images with associated metadata for analysis, determining, for each image in the set of one or more processed images, a set of virtual-camera parameters that describe the position and orientation for a virtual camera that produces a generated image from the time-projected three-dimensional model of the patient's teeth equivalent to the image in the set of one or more processed images, using, for each image in the set of one or more processed images, the standard type of view and additional metadata to generate an initial set of virtual-camera parameters for the image, using the standard type of view and additional metadata to determine a value for an iteration variable; carrying out a number of optimization iterations equal to the value of the iteration variable; and finally refining the virtual-camera parameters for the image, generating, for each image in the set of one or more processed images, a generated image corresponding to the image from the time-projected three-dimensional model of the patient's teeth and the virtual-camera parameters determined for the image, and comparing each image in the set of one or more processed images with the corresponding generated image to generate a comparison value for the image; determining, using the one or more comparison values, whether or not a configuration of the patient's teeth is within a threshold level of correspondence to the expected configuration of the patient's teeth; and storing an indication of the determination in one of the one or more electronic memories.

19. A dental-treatment monitoring system comprising:
one or more processors;
one or more electronic memories that store instructions and data;
one or more mass-storage devices that store encoded images and patient information;
a communications subsystem through which the dental-treatment monitoring system receives images and information from remote computer systems; and
computer instructions, encoded in one or more of the one or more electronic memories, that control the dental-treatment monitoring system to store, in one or more data-storage devices selected from among the one or more electronic memories and one or more mass-storage devices, a three-dimensional model of a patient's teeth, receive, through the communications subsystem, one or more two-dimensional digital photographs of the patient's teeth taken at a time t during the course of a dental treatment, project, in time, the three-dimensional model of the patients teeth to the time t to generate and store a time-projected three-dimensional model of the patient's teeth representing an expected configuration of the patients teeth, compare one or more of the one or more two-dimensional digital photographs to corresponding two-dimensional digital images generated from the time-projected three-dimensional model of the patients teeth to generate one or more comparison values and generate, from the received one or more two-dimensional digital photographs, a set of one or more processed images with associated metadata for analysis, determine, for each image in the set of one or more processed images, a set of virtual-camera parameters that describe the position and orientation for a virtual camera that produces a generated image from the time-projected three-dimensional model of the patient's teeth equivalent to the image in the set of one or more processed images, generate, for each image in the set of one or more processed images, a generated image corresponding to the image from the time-projected three-dimensional model of the patients teeth and the virtual-camera parameters determined for the image, and compare each image in the set of one or more processed images with the corresponding generated image to generate a comparison value for the image and preparing, for each image, a teeth contour from the corresponding generated image; overlaying the teeth contour onto the image, generating a fitness metric for the image, corresponding image, and overlaid contour, wherein the fitness metric is based on a per-pixel cost equal to the normalized dot product of gradient vectors for the image and corresponding image computed for each pixel, determine, from the one or more comparison values, whether or not a configuration of the patient's teeth is within a threshold level of correspondence to the expected configuration of the patients teeth, and store an indication of the determination in one of the one or more electronic memories.

* * * * *